US012758528B2

(12) United States Patent
Givskov et al.

(10) Patent No.: US 12,758,528 B2
(45) Date of Patent: Oct. 13, 2026

(54) COMPOUNDS HAVING PSEUDOMONAS ANTI-BIOFILM PROPERTIES

(71) Applicants: Københavns Universitet, Copenhagen K (DK); Danmarks Tekniske Universitet, Kgs. Lyngby (DK)

(72) Inventors: Michael Givskov, Copenhagen K (DK); Tim Tolker-Nielsen, Copenhagen K (DK); Jens Bo Andersen, Copenhagen K (DK); Tim Holm-Jakobsen, Copenhagen K (DK); Louise Dahl Hultqvist, Copenhagen K (DK); Carl Martin Peter Nilsson, Copenhagen K (DK); Thomas Eiland Nielsen, Copenhagen K (DK); Katrine Qvortrup, Kgs. Lyngby (DK)

(73) Assignees: Københavns Universitet, Copenhagen (DK); Danmarks Tekniske Universitet, Kgs. Lyngby (DK)

( * ) Notice: Subject to any disclaimer, the term of this patent is extended or adjusted under 35 U.S.C. 154(b) by 675 days.

(21) Appl. No.: 18/042,755

(22) PCT Filed: Aug. 27, 2021

(86) PCT No.: PCT/EP2021/073753

§ 371 (c)(1),
(2) Date: Feb. 23, 2023

(87) PCT Pub. No.: WO2022/043503

PCT Pub. Date: Mar. 3, 2022

(65) Prior Publication Data

US 2023/0321043 A1 Oct. 12, 2023

(30) Foreign Application Priority Data

Aug. 27, 2020 (EP) .................................... 20193050

(51) Int. Cl.

| | |
|---|---|
| ***A61K 31/415*** | (2006.01) |
| ***A01N 43/56*** | (2006.01) |
| ***A01N 43/80*** | (2006.01) |
| ***A01P 1/00*** | (2006.01) |
| ***A61K 9/00*** | (2006.01) |
| ***A61K 31/42*** | (2006.01) |
| ***A61K 31/4439*** | (2006.01) |
| ***A61K 31/4709*** | (2006.01) |
| ***A61K 31/496*** | (2006.01) |
| ***A61K 31/635*** | (2006.01) |
| ***A61K 31/702*** | (2006.01) |
| ***A61P 13/02*** | (2006.01) |
| ***A61P 31/04*** | (2006.01) |
| ***C02F 1/50*** | (2023.01) |

(52) U.S. Cl.

CPC ............ *A61K 31/415* (2013.01); *A01N 43/56* (2013.01); *A01N 43/80* (2013.01); *A01P 1/00* (2021.08); *A61K 9/0053* (2013.01); *A61K 31/42* (2013.01); *A61K 31/4439* (2013.01); *A61K 31/4709* (2013.01); *A61K 31/496* (2013.01); *A61K 31/635* (2013.01); *A61K 31/702* (2013.01); *A61P 13/02* (2018.01); *A61P 31/04* (2018.01); *C02F 1/50* (2013.01); *C02F 2303/04* (2013.01)

(58) Field of Classification Search

None

See application file for complete search history.

(56) References Cited

U.S. PATENT DOCUMENTS

| | | | | |
|---|---|---|---|---|
| 6,214,813 | B1 * | 4/2001 | Zhang ................. | C07D 231/38 514/404 |
| 2011/0015137 | A1 * | 1/2011 | Cottarel ................ | A61K 45/06 514/285 |

FOREIGN PATENT DOCUMENTS

| | | | |
|---|---|---|---|
| EP | 2712863 | A1 | 4/2014 |
| WO | WO 01/77080 | A2 | 10/2001 |
| WO | WO 2006/024858 | A1 | 3/2006 |
| WO | WO 2006/045041 | A2 | 4/2006 |
| WO | WO 2006/125262 | A1 | 11/2006 |
| WO | WO 2014/011663 | A1 | 1/2014 |
| WO | WO 2017/044091 | A1 | 3/2017 |

OTHER PUBLICATIONS

Patel P, Wermuth HR, Calhoun C, et al. Antibiotics. [Updated May 26, 2023]. In: StatPearls [Internet]. Treasure Island (FL): StatPearls Publishing; Jan. 2025. Available from: https://www.ncbi.nlm.nih.gov/books/NBK535443/ (Year: 2025).*

Sharma et al. icrobial Biofilm: A Review on Formation, Infection, Antibiotic Resistance, Control Measures, and Innovative Treatment. Microorganisms. Jun. 19, 2023;11(6):1614. doi: 10.3390/microorganisms11061614. (Year: 2023).*

(Continued)

*Primary Examiner* — Lauren Wells

(74) *Attorney, Agent, or Firm* — Knobbe, Martens, Olson & Bear, LLP

(57) ABSTRACT

The present invention relates to c-di-GMP lowering chemical compounds having anti-biofilm properties. In particular, the present invention relates to anti-biofilm compounds or salts or tautomers thereof for use in treatment and/or prevention of bacterial biofilm infection in human subjects caused by biofilm-forming bacteria of the genus *Pseudomonas*, in particular *Pseudomonas* spp. including *P. aeruginosa*. Methods of treating such infections in human subjects are contemplated as well. The present inventions further relates to the use of an anti-biofilm compound or a salt or tautomer thereof for dispersing biofilms in industrial water systems.

11 Claims, 20 Drawing Sheets

(56) References Cited

OTHER PUBLICATIONS

Alsaedi, Amani M.R. et al., “Synthesis and Antimicrobial Evaluation of Novel Pyrazolopyrimidines Incorporated with Mono- and Diphenylsulfonyl Groups” Molecules, 2019, pp. 1-19, vol. 24, No. 4009.
An, Shuwen et al., “Modulation of Pseudomonas aeruginosa Biofilm Dispersal by a Cyclic-Di-GMP Phosphodiesterase with a Putative Hypoxia-Sensing Domain” Applied and Environmental Microbiology, Dec. 2010, pp. 8160-8173, vol. 76, No. 24.
Baraquet, Claudine et al., “FleQ DNA Binding Consensus Sequence Revealed by Studies of FleQ-Dependent Regulation of Biofilm Gene Expression in Pseudomonas aeruginosa” Journal of Bacteriology, Jan. 2016, pp. 178-186, vol. 198, No. 1.
Bernard, Christophe S. et al., “Organization and PprB-Dependent Control of the Pseudomonas aeruginosa tad Locus, Involved in Flp Pilus Biology” Journal of Bacteriology, Mar. 2009, pp. 1961-1973, vol. 191, No. 6.
Borlee, Bradley R. et al., “Pseudomonas aeruginosa uses a cyclic-di-GMP-regulated adhesin to reinforce the biofilm extracellular matrix” Molecular Microbiology, 2010, pp. 827-842, vol. 75, No. 4.
Bryers, James D. “Medical Biofilms” Biotechnol Bioeng., May 2008, pp. 1-31, vol. 100, No. 1.
Ciofu, Oana et al., “Tolerance and Resistance of Pseudomonas aeruginosa Biofilms to Antimicrobial Agents—How P. aeruginosa Can Escape Antibiotics” Frontiers in Microbiology, May 2019, pp. 1-15, vol. 10, Article 913.
Crusz, Shanika A. et al., “Bursting the bubble on bacterial biofilms: a flow cell methodology” Biofouling, Sep. 2012, pp. 835-842, vol. 28, No. 8.
Donlan, Rodney M. “Biofilms: Microbial Life on Surfaces” Emerging Infectious Diseases, Sep. 2002, pp. 881-890, vol. 8, No. 9.
Fazli, Mustafa et al., “Regulation of biofilm formation in *Pseudomonas* and *Burkholderia* species” Environmental Microbiology, 2014, pp. 1961-1981, vol. 16, No. 7.
Friedman, Lisa et al., “Genes involved in matrix formation in Pseudomonas aeruginosa PA14 biofilms” Molecular Microbiology, 2004, pp. 675-690, vol. 51, No. 3.
Groizeleau, Julie et al., “The anti-cancerous drug doxorubicin decreases the c-di-GMP content in Pseudomonas aeruginosa but promotes biofilm formation” Microbiology, 2016, pp. 1797-1807, vol. 162.
Hall, Clayton W. et al., “Molecular mechanisms of biofilm-based antibiotic resistance and tolerance in pathogenic bacteria” FEMS Microbiology Reviews, 2017, pp. 276-301, vol. 41, No. 3.
Hickman, Jason W. et al., “A chemosensory system that regulates biofilm formation through modulation of cyclic diguanylate levels” PNAS, Oct. 2005, pp. 14422-14427, vol. 102, No. 40.
Jakobsen, Tim Holm et al., “Bacterial Biofilm Control by Perturbation of Bacterial Signaling Processes” International Journal of Molecular Sciences, 2017, pp. 1-27, vol. 18, No. 1970.
Jenal, Urs et al., “Cyclic di-GMP: second messenger extraordinaire” Nature Reviews Microbiology, May 2017, pp. 271-284, vol. 15.
Kuchma, Sherry L. et al., “BifA, a Cyclic-Di-GMP Phosphodiesterase, Inversely Regulates Biofilm Formation and Swarming Motility by Pseudomonas aeruginosa PA14” Journal of Bacteriology, Nov. 2007, pp. 8165-8178, vol. 189, No. 22.
Kulasakara, Hemantha et al., “Analysis of Pseudomonas aeruginosa diguanylate cyclases and phosphodiesterases reveals a role for bis-(3'-5')-cyclic-GMP in virulence” PNAS, Feb. 2006, pp. 2839-2844, vol. 103, No. 8.
Kulasekara, Hemantha D. “Transposon Mutagenesis” Methods in Molecular Biology, 2014, pp. 501-519, vol. 1149.
Pamp, Sünje Johanna et al., “Multiple Roles of Biosurfactants in Structural Biofilm Development by Pseudomonas aeruginosa” Journal of Bacteriology, Mar. 2007, pp. 2531-2539, vol. 189, No. 6.
Parrino, Barbara et al., “Synthetic small molecules as anti-biofilm agents in the struggle against antibiotic resistance” European Journal of Medicinal Chemistry, 2019, pp. 154-178, vol. 161.
Pendleton, Jack Norman et al., “The antimicrobial potential of ionic liquids: A source of chemical diversity for infection and biofilm control” International Journal of Antimicrobial Agents, 2015, pp. 131-139, vol. 46.
Rybtke, Morten T. et al., “Fluorescence-Based Reporter for Gauging Cyclic Di-GMP Levels in Pseudomonas aeruginosa” Applied and Environmental Microbiology, Aug. 2012, pp. 5060-5069, vol. 78, No. 15.
Savjani, Ketan T. et al., “Drug Solubility: Importance and Enhancement Techniques” ISRN Pharmaceutics, May 2012, pp. 1-10, vol. 2012, Article 195727.
Sayed, G.H. et al., “Synthesis, Characterization and Biological Activity of Some Pyrazole-Pyrazolone Derivatives” Egypt. J. Chem, 2016, pp. 663-672, vol. 59, No. 4.
Sorci, Leonardo et al., “Targeting NAD Biosynthesis in Bacterial Pathogens: Structure-Based Development of Inhibitors of Nicotinate Mononucleotide Adenylyltransferase NadD” Chemistry & Biology, Aug. 2009, pp. 849-861, vol. 16.
Starkey, Melissa et al., “Pseudomonas aeruginosa Rugose Small-Colony Variants Have Adaptations That Likely Promote Persistence in the Cystic Fibrosis Lung” Journal of Bacteriology, Jun. 2009, pp. 3492-3503, vol. 191, No. 11.
Yu, Shan et al., “PslG, a self-produced glycosyl hydrolase, triggers biofilm disassembly by disrupting exopolysaccharide matrix” Cell Research, 2015, pp. 1352-1367, vol. 25.
ChEBI “4-[(4-fluorophenyl)hydrazinylidene]pyrazole-3,5-diamine” ID:112675.
International Search Report for PCT/EP2021/073753 dated Nov. 24, 2021.

* cited by examiner

H6-335-P1

H6-335-P1

H6-335-P1-HCl

COMPOUNDS HAVING PSEUDOMONAS ANTI-BIOFILM PROPERTIES

CROSS REFERENCE TO RELATED APPLICATIONS

This application is a U.S. National Phase Application of PCT International Application Number PCT/EP2021/073753, filed on Aug. 27, 2021, designating the United States of America and published in the English language, which is an International Application of and claims the benefit of priority to European Patent Application No. 20193050.0, filed on Aug. 27, 2020. The disclosures of the above-referenced applications are hereby expressly incorporated by reference in their entireties.

FIELD OF THE INVENTION

The present invention relates to cyclic di-GMP (cyclic diguanylate, hereinafter "c-di-GMP")-reducing chemical compounds exhibiting anti-biofilm properties.

BACKGROUND OF THE INVENTION

Biofilms consist of densely packed bacteria concealed in shielding biopolymers, and are often attached to surfaces. For billions of years, environmental bacteria have escaped annihilation by forming biofilms. It has become clear that this capacity also plays a key role for the development of chronic, and in particular antibiotic-resistant infections. In the biofilm mode, bacteria attain the highest levels of multiple resistances to the present assortment of antibiotics and antimicrobials, and an almost unlimited capacity to evade the immune system and survive in the infected host.

The increasing population of elderly, hospitalized citizens has sparked a multitude of healthcare acquired infections that have become a major cause of death, disability, and social and economic upheaval for millions of people. Evidence is accumulating that such infections are caused by bacteria in the form of biofilms (Bryers, 2008; Hall and Mah, 2017; Ciofu and Tolker-Nielsen, 2019). A major shortcoming of the current assortment of antibiotics is that it target bacteria present in an unshielded planktonic state. This renders the majority of conventional antibiotics less efficient on biofilms bacteria because the cells are shielded and predominantly exist in a non-growing state.

Compelling evidence suggests that the so-called "c-di-GMP signaling" is a general and key bacterial process that controls the biofilm lifecycle (Fazli et al., 2014; Jenal et al., 2017): A high internal level of c-di-GMP drives planktonic bacteria to form biofilms, whereas reduced c-di-GMP levels promote dispersal of biofilm bacteria, leading to the bacteria assuming the planktonic mode of life.

WO2006125262A1 discloses a method for promoting dispersal of, or preventing formation of a microbial (e.g. *P. aeruginosa*) biofilm, the method comprising: exposing said biofilm to an effective amount of nitric oxide.

EP2712863A1 discloses compositions and compounds useful for reducing or inhibiting the formation of a biofilm and for controlling or treating a chronic bacterial infection involving biofilms. EP2712863A1 also discloses various different compounds useful for inhibiting biofilms of *P. aeruginosa.*

WO06045041A2 discloses methods for microbial biofilm destruction and mentions *P. aeruginosa* as such biofilm forming bacteria. WO06045041A2 also states that the formation and maintenance of such biofilms is dependent on signaling pathways responsive to the internal level of cyclic di-GMP and emphasizes that in response to a sudden drop in the cyclic di-GMP level, microbes detach from the biofilm, and thereby become more readily treatable with conventional antibiotics.

WO17044091A1 discloses various methods of reducing or killing *P. aeruginosa* biofilm by various known antibiotics and by the use of combinations of aminoglycoside and triclosan.

WO2014011663A1 discloses agents (various unspecified compounds capable of inhibiting the activity of diguanylate cyclase (DGC) enzymes) for use in inhibiting *Pseudomonas aeruginosa* biofilm formation.

Many of today's problematic infections are caused by bacterial biofilms. Bacteria in the biofilm mode are hard to kill with the current assortment of antimicrobials. Neglecting this life-form has been a significant flaw in previous antimicrobial discovery where the concentration dependent inhibition of planktonic bacterial growth in a test tube (MIC value) has been the hallmark of antimicrobial efficacy.

In addition, diguanylate cyclase (DGC) enzymes catalyze formation of c-di-GMP, whereas phosphodiesterase (PDE) enzymes catalyze degradation of c-di-GMP. In other words, this is the decision maker for bacteria to be or not to be organized in a biofilm. In response to a variety of environmental and chemical signals, a number of different DGC and PDE enzymes modulate the internal c-di-GMP content either by catalyzing the synthesis or the breakdown of c-di-GMP. The hunt is therefore set to pursue c-di-GMP signaling as a novel target for antimicrobial intervention principles.

Hence, the hypothesis of the present invention is that biofilms can be prevented from establishing and/or be dismantled by chemical compounds that activate PDEs or inactivate DGCs. The inventors have applied a high throughput screening (HTS) approach, testing around 50,000 chemical compounds for their ability to reduce the bacterial c-di-GMP level in the ESKAPEE pathogen *Pseudomonas aeruginosa* (hereinafter "*P. aeruginosa*") and have identified small molecule entities that modulate the c-di-GMP system to drive *P. aeruginosa* to assume its planktonic life form.

SUMMARY OF THE INVENTION

The inventors have previously found that biofilm bacteria of the ESKAPEE pathogen *P. aeruginosa* can be dispersed by overexpression of a single gene encoding a native c-di-GMP degrading phosphodiesterase.

The H6-range of compounds (H6-compounds) are narrow range anti-biofilm compounds in the sense that H6-compounds do not induce dispersal of biofilm of the other members of the ESKAPEE bacteria, *Enterococcus facieum, Staphylococcus aureus, Klebsiella pneumoniae, Acinetobacter baumanii*, and *Enterobacter cloacae* (data not shown).

In addition, the H6-compounds do not induce dispersal of biofilm of other important pathogens such as *Escherichia coli, Burkholderia cenocepacia*, and *Stenotrophomonas maltophilia* (data not shown).

Taken together with the highly restricted structural freedom to maintain biological activity (SAR "structure-activity relationship" analysis), the effects are likely to be restricted to bacteria of the genus *Pseudomonas*, in particular *Pseudomonas* spp. including *P. aeruginosa.*

Hence, the present invention relates to a c-di-GMP-reducing chemical scaffold denoted H6, several compounds of which activate the c-di-GMP degrading activity of the BifA phosphodiesterase (c-di-GMP phosphodiesterase BifA). By doing so, compounds of this scaffold can inhibit formation of biofilms formed by bacteria of the genus *Pseudomonas*, in particular *Pseudomonas* spp. including *P. aeruginosa*, and they are capable of dispersing bacteria from already formed biofilms. Those liberated bacteria show increased sensitivity to conventional antibiotics as compared with their biofilm counterparts. Importantly; H6 compounds are not to be considered antibiotic per se (do neither kill, prevent growth nor inhibit bacterial cell division). Their antibiofilm properties arise because they provoke an enzymatic down-regulation of the internal c-di-GMP level thereby forcing the exposed bacteria to assume the planktonic life mode instead of the sessile biofilm mode.

Consequently, for medical applications, it is possible to combine H6 induced biofilm dispersal with synergistic antibiotic treatments. As a result, biofilm infections can be dismantled and subsequently eradicated by combinatorial treatments with clinically relevant antibiotics (FIG. 11).

The present invention also comprises industrial applications including water sanitation procedures against biofilm formed by bacteria of the genus *Pseudomonas*, in particular *Pseudomonas* spp. including *P. aeruginosa.*

Thus, an object of the present invention relates to an anti-biofilm compound according to chemical formula (1):

Formula (1)

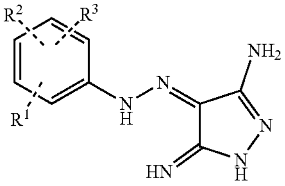

wherein $R^1$, $R^2$, and $R^3$ are independently selected from the group consisting of hydrogen, hydroxy, fluoro, and oxido with counterion, wherein the counterion is selected from the group consisting of organic cations, wherein the group of organic cations is selected from ammonium salts, including protonated forms of arginine, benzathine, chloroprocaine, choline, diethanolamine, ethanolamine, ethylenediamine, lysine, histidine, meglumine, procaine, triethylamine, and/or inorganic cations, including sodium, lithium, potassium, calcium, magnesium and zinc, or a pharmaceutically acceptable salt or tautomer thereof, for use in treatment and/or prevention of a bacterial biofilm infection.

When used throughout this application the term "oxido" refers to negatively charged oxygen, i.e. $O^-$.

Another aspect of the present invention relates to a compound according to Formula (3)

Formula (3)

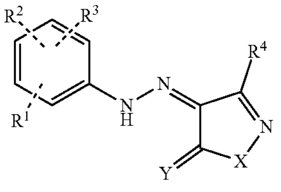

wherein $R^1$, $R^2$, and $R^3$ are substituents to the benzene ring independently selected from the group consisting of hydrogen, carboxy, carbamoyl, aminosulfonyl, hydroxy, amino, $(C_1\text{-}C_4)$alkyl, $(C_1\text{-}C_4)$alkoxy, $(C_2\text{-}C_4)$alkenyloxy, fluoro, chloro, iodo, bromo, amino, nitro, trifluoromethyl, and oxido further connected to a cationic counterion, $R^4$ is selected from the group consisting of $—NHR^5$, $—NH_2$, and $—NH_3^+$, X is selected from the group consisting of $NR^6$, NH, and $NH_2^+$, Y is selected from the group consisting of $NR^7$, NH, and $NH_2^+$, $R^5$, $R^6$, and $R^7$ are independently selected from the group consisting of hydrogen, $(C_1\text{-}C_4)$alkyl, acetyl, optionally substituted phenyl, optionally substituted benzyl, benzoyl, benzenesulfonyl, aminobenzenesulfonyl, hydroxy$(C_1\text{-}C_4)$alkyl, and pyridinoyl, and wherein any or all of the $—NH_3^+$ groups or $NH_2^+$ moieties are further connected to anionic counterions;

or a pharmaceutically acceptable salt thereof, or tautomer thereof.

Yet another aspect of the present invention is to provide a use of an anti-biofilm compound according to chemical formula (1):

Formula (1)

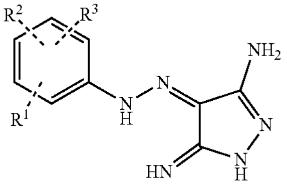

wherein $R^1$, $R^2$, and $R^3$ are independently selected from the group consisting of hydrogen, hydroxy, fluoro, and oxido with counterion, wherein the counterion is selected from the group consisting of organic cations, wherein the group of organic cations is selected from ammonium salts, including protonated forms of arginine, benzathine, chloroprocaine, choline, diethanolamine, ethanolamine, ethylenediamine, lysine, histidine, meglumine, procaine, triethylamine, and/or inorganic cations, including sodium, lithium, potassium, calcium, magnesium and zinc, or a pharmaceutically acceptable salt or tautomer thereof, for preventing and/or dispersing biofilms in industrial water systems formed by bacteria of the genus *Pseudomonas*, in particular *Pseudomonas* spp. including *P. aeruginosa.*

Figure 1:
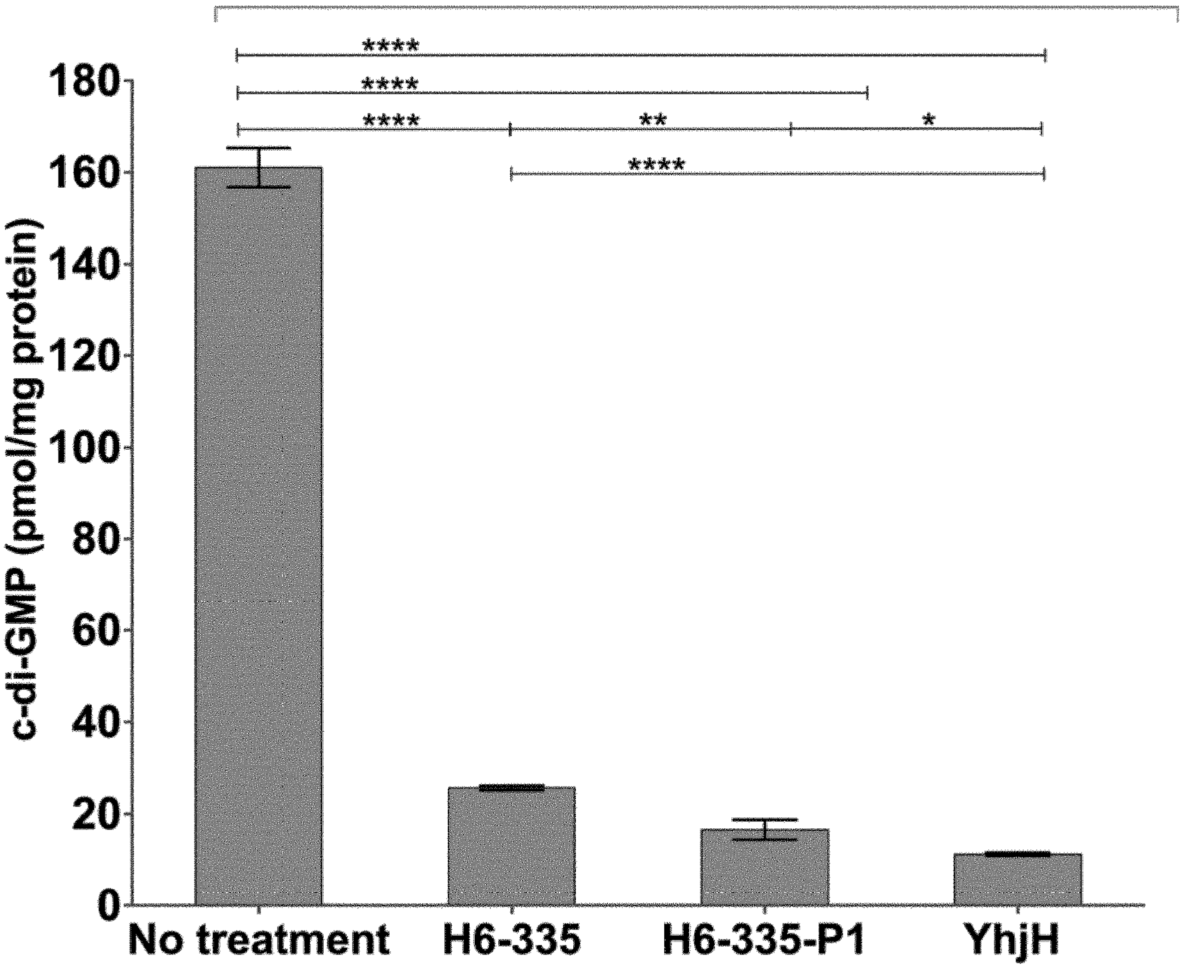
FIG. 1 shows the effect of H6-335 and H6-335-P1 on the c-di-GMP level of *P. aeruginosa* determined by HPLC coupled MS-MS quantification of c-di-GMP extracts.

The present invention will now be described in more detail in the following.

DETAILED DESCRIPTION OF THE INVENTION

By means of genetic analyses, the inventors have discovered and demonstrated that H6-compounds according to the invention control the enzymatic activity of the membrane bound phosphodiesterase BifA to reduce the amount of intracellular c-di-GMP thereby leading to the inhibition and disruption of *Pseudomonas* spp. biofilms. In this context, the following embodiments of the invention are contemplated.

Second Medical Use

According to one embodiment, the present invention relates to an anti-biofilm compound according to chemical formula (1):

Formula (1)

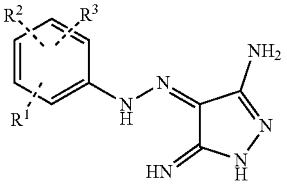

wherein $R^1$, $R^2$, and $R^3$ are independently selected from the group consisting of hydrogen, hydroxy, fluoro, and oxido with counterion, wherein the counterion is selected from the group consisting of organic cations, wherein the group of organic cations is selected from ammonium salts, including protonated forms of arginine, benzathine, chloroprocaine, choline, diethanolamine, ethanolamine, ethylenediamine, lysine, histidine, meglumine, procaine, triethylamine, and/or inorganic cations, including sodium, lithium, potassium, calcium, magnesium and zinc, or a pharmaceutically acceptable salt or tautomer thereof, for use in treatment and/or prevention of a bacterial biofilm infection.

According to a further embodiment, the present invention relates to a compound according to chemical formula (1):

Formula (1)

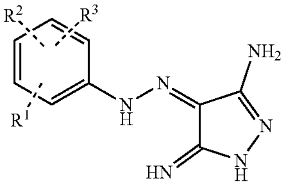

wherein $R^1$, $R^2$, and $R^3$ are independently selected from the group consisting of hydrogen, hydroxy, fluoro, and oxido with counterion, wherein the counterion is selected from the group consisting of organic cations, wherein the group of organic cations is selected from ammonium salts, including protonated forms of arginine, benzathine, chloroprocaine, choline, diethanolamine, ethanolamine, ethylenediamine, lysine, histidine, meglumine, procaine, triethylamine, and/or inorganic cations, including sodium, lithium, potassium, calcium, magnesium and zinc, or a pharmaceutically acceptable salt or tautomer thereof, wherein the pharmaceutically acceptable salt is a salt according to chemical formula (1) wherein one or more of the primary or secondary amino groups are protonated and the resulting positive charge countered by anions selected from the group consisting of organic anions, acetate, trifluoroacetate, aspartate, benzenesulfonate, benzoate, besylate, bicarbonate, bitartrate, camsylate, carbonate, citrate, decanoate, edetate, esylate, fumarate, gluceptate, gluconate, glutamate, glycolate, hexanoate, hydroxynaphthoate, isethionate, lactate, lactobionate, malate, maleate, mandelate, mesylate, methylsulfate, mucate, napsylate, octanoate, oleate, pamoate, pantothenate, polygalactonate, propionate, salicylate, stearate, succinate, tartrate, teoclate, tosylate, inorganic anions, tetrafluoroborate, hexafluorophosphate, bromide, chloride, iodide, nitrate, phosphate, and sulfate, for use in treatment of a bacterial infection caused by biofilm-forming bacteria of the genus *Pseudomonas*, in particular *Pseudomonas* spp. including *P. aeruginosa.*

According to a further embodiment, the present invention relates to an anti-biofilm compound according to chemical formula (1):

Formula (1)

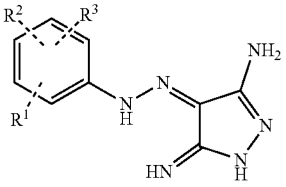

wherein $R^1$, $R^2$, and $R^3$ are independently selected from the group consisting of hydrogen, hydroxy, fluoro, and oxido with counterion, wherein the counterion is selected from the group consisting of organic cations, wherein the group of organic cations is selected from ammonium salts, including protonated forms of arginine, benzathine, chloroprocaine, choline, diethanolamine, ethanolamine, ethylenediamine, lysine, histidine, meglumine, procaine, triethylamine, and/or inorganic cations, including sodium, lithium, potassium, calcium, magnesium and zinc, or a pharmaceutically acceptable salt or tautomer thereof, wherein the pharmaceutically acceptable salt is a salt according to chemical formula (1) wherein one or more of the primary or secondary amino groups are protonated and the resulting positive charge countered by anions selected from the group consisting of organic anions, acetate, trifluoroacetate, aspartate, benzenesulfonate, benzoate, besylate, bicarbonate, bitartrate, camsylate, carbonate, citrate, decanoate, edetate, esylate, fumarate, gluceptate, gluconate, glutamate, glycolate, hexanoate, hydroxynaphthoate, isethionate, lactate, lactobionate, malate, maleate, mandelate, mesylate, methylsulfate, mucate, napsylate, octanoate, oleate, pamoate, pantothenate, polygalactonate, propionate, salicylate, stearate, succinate, tartrate, teoclate, tosylate, inorganic anions, tetrafluoroborate, hexafluorophosphate, bromide, chloride, iodide, nitrate, phosphate, and sulfate, wherein the molecular target of said anti-biofilm compounds is the BifA phosphodiesterase in *P. aeruginosa;* for use in treatment of a bacterial infection caused by biofilm-forming bacteria of the genus *Pseudomonas*, in particular *Pseudomonas* spp. including *P. aeruginosa.*

According to still another embodiment, the present invention relates to an anti-biofilm compound according to chemical formula (1):

Formula (1)

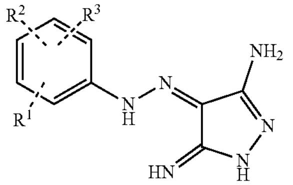

wherein $R^1$, $R^2$, and $R^3$ are independently selected from the group consisting of hydrogen, hydroxy, fluoro, and oxido with counterion, wherein the counterion is selected from the group consisting of organic cations, wherein the group of organic cations is selected from ammonium salts, including protonated forms of arginine, benzathine, chloroprocaine, choline, diethanolamine, ethanolamine, ethylenediamine, lysine, histidine, meglumine, procaine, triethylamine, and/or inorganic cations, including sodium, lithium, potassium, calcium, magnesium and zinc, or a pharmaceutically acceptable salt or tautomer thereof, for use in treatment of a bacterial infection caused by biofilm-forming bacteria of the genus *Pseudomonas*, in particular *Pseudomonas* spp. including *P. aeruginosa* and the infection is chosen from the group consisting of infections in wounds, eyes, urinary tract and respiratory tract.

According to a further embodiment, the present invention relates to an anti-biofilm compound according to chemical formula (1):

Formula (1)

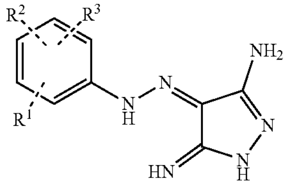

wherein $R^1$, $R^2$, and $R^3$ are independently selected from the group consisting of hydrogen, hydroxy, fluoro, and oxido with counterion, wherein the counterion is selected from the group consisting of organic cations, wherein the group of organic cations is selected from ammonium salts, including protonated forms of arginine, benzathine, chloroprocaine, choline, diethanolamine, ethanolamine, ethylenediamine, lysine, histidine, meglumine, procaine, triethylamine, and/or inorganic cations, including sodium, lithium, potassium, calcium, magnesium and zinc, or a pharmaceutically acceptable salt or tautomer thereof, wherein the pharmaceutically acceptable salt is a salt according to chemical formula (1) wherein one or more of the primary or secondary amino groups are protonated and the resulting positive charge countered by anions selected from the group consisting of organic anions, acetate, trifluoroacetate, aspartate, benzenesulfonate, benzoate, besylate, bicarbonate, bitartrate, camsylate, carbonate, citrate, decanoate, edetate, esylate, fumarate, gluceptate, gluconate, glutamate, glycolate, hexanoate, hydroxynaphthoate, isethionate, lactate, lactobionate, malate, maleate, mandelate, mesylate, methylsulfate, mucate, napsylate, octanoate, oleate, pamoate, pantothenate, polygalactonate, propionate, salicylate, stearate, succinate, tartrate, teoclate, tosylate, inorganic anions, tetrafluoroborate, hexafluorophosphate, bromide, chloride, iodide, nitrate, phosphate, and sulfate, wherein the anti-biofilm compound or the pharmaceutically acceptable salt or tautomer thereof is used in combination with one or more antibiotic(s) in a controlled release formulation or in a form suitable for topical, oral, intravenous, intramuscular or intraperitoneal administration, for use in treatment of a bacterial infection caused by biofilm-forming bacteria of the genus *Pseudomonas*, in particular *Pseudomonas* spp. including *P. aeruginosa.*

According to still another embodiment, the present invention relates to an anti-biofilm compound according to chemical formula (1):

Formula (1)

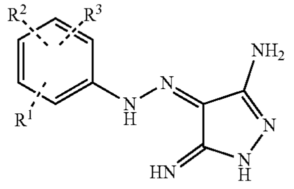

wherein $R^1$, $R^2$, and $R^3$ are independently selected from the group consisting of hydrogen, hydroxy, fluoro, and oxido with counterion, wherein the counterion is selected from the group consisting of organic cations, wherein the group of organic cations is selected from ammonium salts, including protonated forms of arginine, benzathine, chloroprocaine, choline, diethanolamine, ethanolamine, ethylenediamine, lysine, histidine, meglumine, procaine, triethylamine, and/or inorganic cations, including sodium, lithium, potassium, calcium, magnesium and zinc, or a pharmaceutically acceptable salt or tautomer thereof, wherein the anti-biofilm compound or the pharmaceutically acceptable salt or tautomer thereof is used in combination with one or more antibiotic(s) in a controlled release formulation or in a form suitable for topical, oral, intravenous, intramuscular or intraperitoneal administration, for use in treatment of a bacterial infection caused by biofilm-forming bacteria of the genus *Pseudomonas*, in particular *Pseudomonas* spp. including *P. aeruginosa* and the infection is chosen from the group consisting of infections in wounds, eyes, urinary tract and respiratory tract.

According to still another embodiment, the present invention relates to a an anti-biofilm compound 4-[(2-fluorophenyl) hydrazinylidene]pyrazole-3,5-diamine (H6-335-P1) having the following formula (2):

Formula (2)

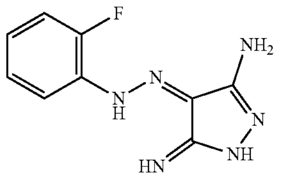

or a pharmaceutically acceptable salt or tautomer thereof, for use in treatment of a bacterial infection.

According to a further embodiment, the present invention relates to an anti-biofilm compound 4-[(2-fluorophenyl) hydrazinylidene]pyrazole-3,5-diamine (H6-335-P1) having the following formula (2):

Formula (2)

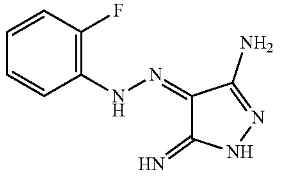

or a pharmaceutically acceptable salt or tautomer thereof, wherein the pharmaceutically acceptable salt is a salt according to chemical formula (1) wherein one or more of the primary or secondary amino groups are protonated and the resulting positive charge countered by anions selected from the group consisting of organic anions, acetate, trifluoroacetate, aspartate, benzenesulfonate, benzoate, besylate, bicarbonate, bitartrate, camsylate, carbonate, citrate, decanoate, edetate, esylate, fumarate, gluceptate, gluconate, glutamate, glycolate, hexanoate, hydroxynaphthoate, isethionate, lactate, lactobionate, malate, maleate, mandelate, mesylate, methylsulfate, mucate, napsylate, octanoate, oleate, pamoate, pantothenate, polygalactonate, propionate, salicylate, stearate, succinate, tartrate, teoclate, tosylate, inorganic anions, tetrafluoroborate, hexafluorophosphate, bromide, chloride, iodide, nitrate, phosphate, and sulfate, for use in treatment of a bacterial infection caused by biofilm-forming bacteria of the genus *Pseudomonas*, in particular *Pseudomonas* spp. including *P. aeruginosa.*

According to still another embodiment, the present invention relates to an anti-biofilm compound 4-[(2-fluorophenyl) hydrazinylidene]pyrazole-3,5-diamine (H6-335-P1) having the following formula (2):

Formula (2)

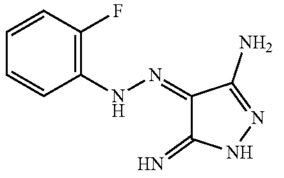

or a pharmaceutically acceptable salt or tautomer thereof, wherein the pharmaceutically acceptable salt is a salt according to chemical formula (1) wherein one or more of the primary or secondary amino groups are protonated and the resulting positive charge countered by anions selected from the group consisting of organic anions, acetate, trifluoroacetate, aspartate, benzenesulfonate, benzoate, besylate, bicarbonate, bitartrate, camsylate, carbonate, citrate, decanoate, edetate, esylate, fumarate, gluceptate, gluconate, glutamate, glycolate, hexanoate, hydroxynaphthoate, isethionate, lactate, lactobionate, malate, maleate, mandelate, mesylate, methylsulfate, mucate, napsylate, octanoate, oleate, pamoate, pantothenate, polygalactonate, propionate, salicylate, stearate, succinate, tartrate, teoclate, tosylate, inorganic anions, tetrafluoroborate, hexafluorophosphate, bromide, chloride, iodide, nitrate, phosphate, and sulfate, for use in treatment of a bacterial infection caused by biofilm-forming bacteria of the genus *Pseudomonas*, in particular *Pseudomonas* spp. including *P. aeruginosa* and the infection is chosen from the group consisting of infections in wounds, eyes, urinary tract and respiratory tract.

According to a still further embodiment, the present invention relates to an anti-biofilm compound 4-[(2-fluorophenyl) hydrazinylidene]pyrazole-3,5-diamine (H6-335-P1) having the following formula (2):

Formula (2)

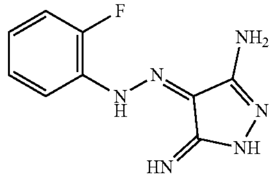

or a pharmaceutically acceptable salt or tautomer thereof, wherein the pharmaceutically acceptable salt is a salt according to chemical formula (1) wherein one or more of the primary or secondary amino groups are protonated and the resulting positive charge countered by anions selected from the group consisting of organic anions, acetate, trifluoroacetate, aspartate, benzenesulfonate, benzoate, besylate, bicarbonate, bitartrate, camsylate, carbonate, citrate, decanoate, edetate, esylate, fumarate, gluceptate, gluconate, glutamate, glycolate, hexanoate, hydroxynaphthoate, isethionate, lactate, lactobionate, malate, maleate, mandelate, mesylate, methylsulfate, mucate, napsylate, octanoate, oleate, pamoate, pantothenate, polygalactonate, propionate, salicylate, stearate, succinate, tartrate, teoclate, tosylate, inorganic anions, tetrafluoroborate, hexafluorophosphate, bromide, chloride, iodide, nitrate, phosphate, and sulfate, wherein the anti-biofilm compound or the pharmaceutically acceptable salt or tautomer thereof is used in combination with one or more antibiotic(s) in a controlled release formulation or in a form suitable for topical, oral, intravenous, intramuscular or intraperitoneal administration, for use in treatment of a bacterial infection caused by biofilm-forming bacteria of the genus *Pseudomonas*, in particular *Pseudomonas* spp. including *P. aeruginosa* and the infection is chosen from the group consisting of infections in wounds, eyes, urinary tract and respiratory tract.

Compounds as Such

According to another embodiment, the present invention relates to a compound according to Formula (3)

Formula (3)

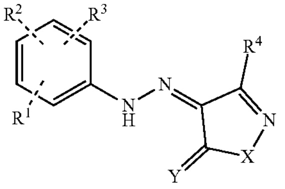

wherein $R^1$, $R^2$, and $R^3$ are substituents to the benzene ring independently selected from the group consisting of hydrogen, carboxy, carbamoyl, aminosulfonyl, hydroxy, amino, $(C_1\text{-}C_4)$alkyl, $(C_1\text{-}C_4)$alkoxy, $(C_2\text{-}C_4)$alkenyloxy, fluoro, chloro, iodo, bromo, amino, nitro, trifluoromethyl, and oxido further connected to a cationic counterion, $R^4$ is selected from the group consisting of —$NHR^5$, —$NH_2$, and —$NH_3^+$, X is selected from the group consisting of $NR^6$, NH, and $NH_2^+$, Y is selected from the group consisting of $NR^7$, NH, and $NH_2^+$, $R^5$, $R^6$, and $R^7$ are independently selected from the group consisting of hydrogen, $(C_1\text{-}C_4)$alkyl, acetyl, optionally substituted phenyl, optionally substituted benzyl, benzoyl, benzenesulfonyl, aminobenzenesulfonyl, hydroxy$(C_1\text{-}C_4)$alkyl, and pyridinoyl, and wherein any or all of the —$NH_3^+$ groups or $NH_2^+$ moieties are further connected to anionic counterions;

or a pharmaceutically acceptable salt thereof, or tautomer thereof.

Use of H6-Compounds for Dispersing Biofilms in Industrial Water Systems

According to another embodiment, the present invention relates to use of an anti-biofilm compound according to chemical formula (1):

Formula (1)

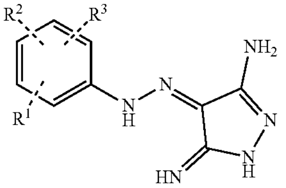

wherein $R^1$, $R^2$, and $R^3$ are independently selected from the group consisting of hydrogen, hydroxy, fluoro, and oxido with counterion, wherein the counterion is selected from the group consisting of organic cations, wherein the group of organic cations is selected from ammonium salts, including protonated forms of arginine, benzathine, chloroprocaine, choline, diethanolamine, ethanolamine, ethylenediamine, lysine, histidine, meglumine, procaine, triethylamine, and/or inorganic cations, including sodium, lithium, potassium, calcium, magnesium and zinc, or a salt or tautomer thereof, for dispersing biofilms in industrial water systems formed by bacteria of the genus *Pseudomonas*, in particular *Pseudomonas* spp. including *P. aeruginosa*.

According to still another embodiment, the present invention relates to use of an anti-biofilm compound according to chemical formula (1):

Formula (1)

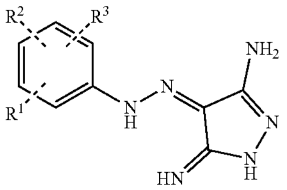

wherein $R^1$, $R^2$, and $R^3$ are independently selected from the group consisting of hydrogen, hydroxy, fluoro, and oxido with counterion, wherein the counterion is selected from the group consisting of organic cations, wherein the group of organic cations is selected from ammonium salts, including protonated forms of arginine, benzathine, chloroprocaine, choline, diethanolamine, ethanolamine, ethylenediamine, lysine, histidine, meglumine, procaine, triethylamine, and/or inorganic cations, including sodium, lithium, potassium, calcium, magnesium and zinc, or a salt or tautomer thereof, wherein the anti-biofilm compound, salt or tautomer thereof is combined with a detergent and/or a biocide.

for dispersing biofilms in industrial water systems formed by bacteria of the genus *Pseudomonas*, in particular *Pseudomonas* spp. including *P. aeruginosa*.

According to still another embodiment, the present invention relates to use of an anti-biofilm compound 4-[(2-fluorophenyl) hydrazinylidene]pyrazole-3,5-diamine (H6-335-P1) having the following formula (2):

Formula (2)

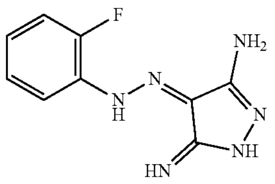

or a salt or tautomer thereof, for preventing development of biofilms and or dispersing already formed biofilms in industrial water systems formed by bacteria of the genus *Pseudomonas*, in particular *Pseudomonas* spp. including *P. aeruginosa*.

According to still another embodiment, the present invention relates to use of an anti-biofilm compound 4-[(2-fluorophenyl) hydrazinylidene]pyrazole-3,5-diamine (H6-335-P1) having the following formula (2):

Formula (2)

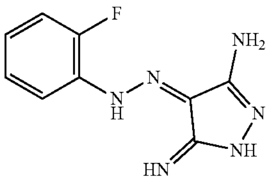

or a salt or tautomer thereof, for dispersing biofilms in industrial water systems formed by bacteria of the genus *Pseudomonas*, in particular *Pseudomonas* spp. including *P. aeruginosa* wherein the anti-biofilm compound or a salt thereof is combined with a detergent and/or a biocide.

Method of Treatment

Another aspect of the present invention relates to a method of treating a bacterial infection in a human subject in need thereof by applying to said subject an anti-biofilm compound according to chemical formula (1):

Formula (1)

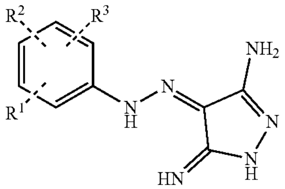

wherein $R^1$, $R^2$, and $R^3$ are independently selected from the group consisting of hydrogen, hydroxy, fluoro, and oxido with counterion, wherein the counterion is selected from the group consisting of organic cations, wherein the group of organic cations is selected from ammonium salts, including protonated forms of arginine, benzathine, chloroprocaine, choline, diethanolamine, ethanolamine, ethylenediamine, lysine, histidine, meglumine, procaine, triethylamine, and/or inorganic cations, including sodium, lithium, potassium, calcium, magnesium and zinc, or a pharmaceutically acceptable salt or tautomer thereof.

Still another aspect of the present invention relates to a method of treating a bacterial infection in a human subject in need thereof by applying to said subject an anti-biofilm compound according to chemical formula (1):

Formula (1)

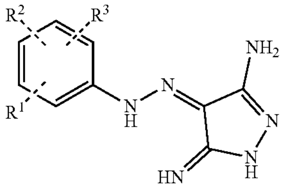

wherein $R^1$, $R^2$, and $R^3$ are independently selected from the group consisting of hydrogen, hydroxy, fluoro, and oxido with counterion, wherein the counterion is selected from the group consisting of organic cations, wherein the group of organic cations is selected from ammonium salts, including protonated forms of arginine, benzathine, chloroprocaine, choline, diethanolamine, ethanolamine, ethylenediamine, lysine, histidine, meglumine, procaine, triethylamine, and/or inorganic cations, including sodium, lithium, potassium, calcium, magnesium and zinc, or a pharmaceutically acceptable salt or tautomer thereof, wherein the pharmaceutically acceptable salt is a salt according to chemical formula (1) wherein one or more of the primary or secondary amino groups are protonated and the resulting positive charge countered by anions selected from the group consisting of organic anions, acetate, trifluoroacetate, aspartate, benzenesulfonate, benzoate, besylate, bicarbonate, bitartrate, camsylate, carbonate, citrate, decanoate, edetate, esylate, fumarate, gluceptate, gluconate, glutamate, glycolate, hexanoate, hydroxynaphthoate, isethionate, lactate, lactobionate, malate, maleate, mandelate, mesylate, methylsulfate, mucate, napsylate, octanoate, oleate, pamoate, pantothenate, polygalactonate, propionate, salicylate, stearate, succinate, tartrate, teoclate, tosylate, inorganic anions, tetrafluoroborate, hexafluorophosphate, bromide, chloride, iodide, nitrate, phosphate, and sulfate.

Still another aspect of the present invention relates to a method of treating a bacterial infection in a human subject in need thereof by applying to said subject an anti-biofilm compound 4-[(2-fluorophenyl) hydrazinylidene]pyrazole-3,5-diamine (H6-335-P1) having the following formula (2):

Formula (2)

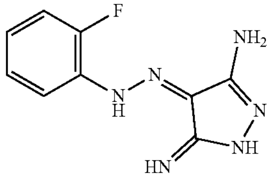

or a pharmaceutically acceptable salt or tautomer thereof, wherein the pharmaceutically acceptable salt is a salt according to chemical formula (1) wherein one or more of the primary or secondary amino groups are protonated and the resulting positive charge countered by anions selected from the group consisting of organic anions, acetate, trifluoroacetate, aspartate, benzenesulfonate, benzoate, besylate, bicarbonate, bitartrate, camsylate, carbonate, citrate, decanoate, edetate, esylate, fumarate, gluceptate, gluconate, glutamate, glycolate, hexanoate, hydroxynaphthoate, isethionate, lactate, lactobionate, malate, maleate, mandelate, mesylate, methylsulfate, mucate, napsylate, octanoate, oleate, pamoate, pantothenate, polygalactonate, propionate, salicylate, stearate, succinate, tartrate, teoclate, tosylate, inorganic anions, tetrafluoroborate, hexafluorophosphate, bromide, chloride, iodide, nitrate, phosphate, and sulfate.

Still another aspect of the present invention relates to a method of treating a bacterial infection infections in wounds, eyes, urinary tract and respiratory tract caused by biofilm-forming bacteria of the genus *Pseudomonas*, in particular *Pseudomonas* spp. including *P. aeruginosa*, in a human subject in need thereof by applying to said subject an anti-biofilm compound 4-[(2-fluorophenyl) hydrazinylidene]pyrazole-3,5-diamine (H6-335-P1) having the following formula (2):

Formula (2)

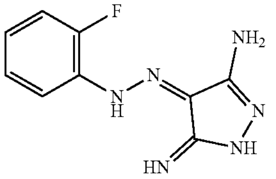

or a pharmaceutically acceptable salt or tautomer thereof;

wherein the pharmaceutically acceptable salt is a salt according to chemical formula (1) wherein one or more of the primary or secondary amino groups are protonated and the resulting positive charge countered by anions selected from the group consisting of organic anions, acetate, trifluoroacetate, aspartate, benzenesulfonate, benzoate, besylate, bicarbonate, bitartrate, camsylate, carbonate, citrate, decanoate, edetate, esylate, fumarate, gluceptate, gluconate, glutamate, glycolate, hexanoate, hydroxynaphthoate, isethionate, lactate, lactobionate, malate, maleate, mandelate, mesylate, methylsulfate, mucate, napsylate, octanoate, oleate, pamoate, pantothenate, polygalactonate, propionate, salicylate, stearate, succinate, tartrate, teoclate, tosylate, inorganic anions, tetrafluoroborate, hexafluorophosphate, bromide, chloride, iodide, nitrate, phosphate, and sulfate.

Still another aspect of the present invention relates to a method of treating a bacterial infection in wounds, eyes, urinary tract and respiratory tract caused by biofilm-forming bacteria of the genus *Pseudomonas*, in particular *Pseudomonas* spp. including *P. aeruginosa*, in a human subject in need thereof by applying to said subject an anti-biofilm compound 4-[(2-fluorophenyl) hydrazinylidene]pyrazole-3,5-diamine (H6-335-P1) having the following formula (2):

Formula (2)

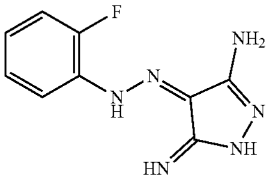

or a pharmaceutically acceptable salt or tautomer thereof, wherein the pharmaceutically acceptable salt is a salt according to chemical formula (1) wherein one or more of the primary or secondary amino groups are protonated and the resulting positive charge countered by anions selected from the group consisting of organic anions, acetate, trifluoroacetate, aspartate, benzenesulfonate, benzoate, besylate, bicarbonate, bitartrate, camsylate, carbonate, citrate, decanoate, edetate, esylate, fumarate, gluceptate, gluconate, glutamate, glycolate, hexanoate, hydroxynaphthoate, isethionate, lactate, lactobionate, malate, maleate, mandelate, mesylate, methylsulfate, mucate, napsylate, octanoate, oleate, pamoate, pantothenate, polygalactonate, propionate, salicylate, stearate, succinate, tartrate, teoclate, tosylate, inorganic anions, tetrafluoroborate, hexafluorophosphate, bromide, chloride, iodide, nitrate, phosphate, and sulfate wherein the anti-biofilm compound or the pharmaceutically acceptable salt or tautomer thereof is used in combination with one or more antibiotic(s) e.g. selected from the group consisting of ciprofloxacin, tobramycin and meropenem in a controlled release formulation or in a form suitable for topical, oral, intravenous, intramuscular or intraperitoneal administration.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples and figures.

EXAMPLES

Example 1 (Identification and Subsequent Synthesis of a Chemical Compound that Triggers Reduction of the Intracellular c-di-GMP Pool)

The inventors of the present invention embarked on a high-throughput approach to screen a synthetic chemical 50.000 compound library for identification of a molecule capable of significantly reducing the c-di-GMP level of a *P. aeruginosa* ΔwspFΔpelΔpsl mutant, which carries the "fluorescent" cdrA-gfp fusion. The ΔwspF mutant overproduces c-di-GMP and the ΔpelΔpsl mutations renders the bacteria deficient in exopolysaccharide production, which keeps the growing bacteria in the planktonic mode.

As judged from the fluorescent output, the most potent compound, denoted H6-335, was at a concentration of 100 μM capable of reducing the fluorescent output of the c-di-GMP monitor with 62% (data not shown).

Synthesis

General Methodologies

All solvents were of HPLC quality from either Sigma Aldrich or VWR Chemicals these and other commercially available reagents were used without further purification. The dry DCM was obtained from a Pure-Solve™ MD-7 Solvent Purification System, from Innovative Technology were $Al_2O_3$ was used as the stationary phase.

$^1$H-NMR, $^{13}$C-NMR, COSY spectra were recorded on Bruker Ascend spectrometer with a Prodigy cryo-probe operating at 400 MHz for $^1$H-NMR and 101 MHz for $^{13}$C-NMR by dissolving the molecule in a deuterated solvent. The specific deuterated solvent used for each compound is stated in Table 2. Chemical shifts (δ) are reported in ppm downfield from TMS (δ=0) using solvent resonance as the internal standard (chloroform-d, $^1$H: 7.26 ppm, $^{13}$C: 77.16 ppm; dimethylsulfoxide-$d_6$, $^1$H: 2.50 ppm, $^{13}$C: 39.52 ppm). Coupling constants (J) are reported in Hz and the field is reported in each case. Multiplicities are reported as singlet (s), broad singlet (br. s), doublet (d), doublet of doublets (dd), doublet of triplets (dt), doublet of doublet of doublets (ddd), doublet of doublet of triplets (ddt), triplet (t), triplet of doublets (td), quartet (q), pentet (p), septet (sep) and multiplets (m).

Evaporation of the solvents was performed using a Heidolph Laborota 4000 efficient under reduced pressure (in vacuo) at different temperatures depending on the boiling point of the solvents.

$N_2$ atmosphere was used in experiments for obtaining an inert atmosphere in reactions that would otherwise react with water or oxygen resulting in undesired side-reactions.

Flash chromatography was performed using Merck Geduran Silica gel 60 Å (particle size 40-63 μm) as the stationary phase. The chromatography method being used, followed the general method developed by Still et al. (J. Org. Chem. 1978, 43, 14, 2923-2925 doi.org/10.1021/jo00408a041). The eluent systems used are specified for relevant products in Table 2. These eluent systems are given as a volume ratio.

TLC was performed using Merck Aluminum Sheets which were precoated with silica gel 60 F254. By placing spots on the TLC plates of solutions containing the different compounds/products and running the TLC in relevant solvent mixtures, the compounds could be separated, as seen from spots on the TLC. The spots were developed using UV-light and/or a suitable staining reagent.

UPLC/MS analysis was run on Waters ACQUITY UPLC system equipped with PDA and either a SQD or a SQD2 electrospray MS detector. Column: Thermo accucore C18 2.6 μm, 2.1×50 mm. Column temp: 50° C. Flow rate: 0.6 mL/min. Acid run: Solvent A1—0.1% formic acid in water, Solvent B1—0.1% formic acid in ACN. Base run: Solvent A2—15 mM NH4Ac in water, Solvent B2—15 mM NH4Ac in ACN/water 9:1. Gradient: (short run) 5% B to 100% B in 2.4 min., hold 0.1 min., total run time 2.6 min. (long run) 5% B to 100% B in 3 min., hold 0.1 min., total run time 5 min.

Preparative HPLC purification was performed on a Waters auto purification system consisting of a 2767 Sample Manager, 2545 Gradient Pump and 2998 PDA detector. Column: XBridge Peptide BEH C18 OBD Prep Column, 130 Å, 5 μm, 19 mm×100 mm. Column temp: Ambient. Flow rate: 20 mL/min. Solvent A2—15 mM $NH_4Ac$ in water, Solvent B2—15 mM NH4Ac in MeCN/water 9:1. Gradient: 5% B to 20% B in min., hold min., gradient: 20% B to 50% B in min., hold min., gradient: 50% B to 70% B in min., hold min., gradient: 70% B to 100% B in min., hold min., run min., recalibrating the column for min. Total run time—18 min.

General Procedure A1—Diazotation with Malononitrile

In a 250 mL conical flask, a solution of the aniline (0.01 mol, 1 eq.) in $H_2O$/ice (50 mL) and conc. HCl (3 mL) was cooled to 0° C. Then, a cold solution of sodium nitrite (0.01 mol, 1 eq.) in 10 mL $H_2O$ was added dropwise under stirring. The mixture was allowed to stir for 30 min., before slow addition of an aqueous cold solution of malononitrile (0.015 mol, 1.5 eq.) and sodium acetate (25 g) in 85 mL $H_2O$. After stirring the reaction mixture at 0° C. for 1 h, the formed solid product was collected by filtration and washed with ice-cold water. For those compounds that did not precipitate, the product was isolated by extraction with EtOAc, dried with $MgSO_4$ and concentrated under vacuum. The product was dried under high vacuum overnight.

General Procedure A2—Diazotation with ethyl-2-cyanoacetate

In a 250 mL conical flask, a solution of the aniline (0.01 mol, 1 eq.) in H2O/ice (50 mL) and conc. HCl (3 mL) was cooled to 0° C. Then, a cold solution of sodium nitrite (0.01 mol, 1 eq.) in $H_2O$ (10 mL) was added dropwise under stirring. The reaction was allowed to stir for 30 min., before slow addition of an aqueous cold solution of ethyl-2-cyanoacetate (0.015 mol, 1.5 eq.) and sodium acetate (25 g) in $H_2O$ (85 mL). After stirring the reaction mixture at 0° C. for 1 h, the precipitated product was collected by filtration and washed with ice-cold water. For those compounds that did not precipitate, the product was isolated by extraction with EtOAc, dried with MgSO4 and concentrated under vacuum. The product was dried under high vacuum overnight.

General Procedure A3—Diazotation with Diethyl Malonate

In a 250 mL conical flask, a solution of the aniline (0.01 mol, 1 eq.) in $H_2O$/ice (50 mL) and conc. HCl (3 mL) was cooled to 0° C. Then, a cold solution of sodium nitrite (0.01 mol, 1 eq.) in $H_2O$ (10 mL) was added dropwise under stirring. The reaction was allowed to stir for 30 min., before slow addition of an aqueous cold solution of diethyl malonate (0.015 mol, 1.5 eq.) and sodium acetate (25 g) in 85 mL $H_2O$. After stirring the reaction mixture at 0° C. for 1 h, the precipitated product was collected by filtration and washed with ice-cold water. For those compounds that did not precipitate, the product was isolated by extraction with EtOAc, dried with $MgSO_4$ and concentrated under vacuum. The product was dried under high vacuum overnight.

General Procedure B1—Cyclization with Hydrazine/Hydrazide

The product from procedure A1→3 (1 eq) was dissolved in EtOH (2.9 mL/mmol), followed by addition of the appropriate hydrazine/hydrazide derivative (1.2 eq). Upon completion of the reaction, the product was isolated by filtration. For those compounds that did not precipitate, the solvent and hydrazine was removed by evaporation at high vacuum to give the product. If purification was needed, it was done with either flash chromatography or preparative HPLC.

The H6-335-P1 compound is synthesized by this general procedure B1 (cyclization with hydrazine/hydrazide).

Figure 2:
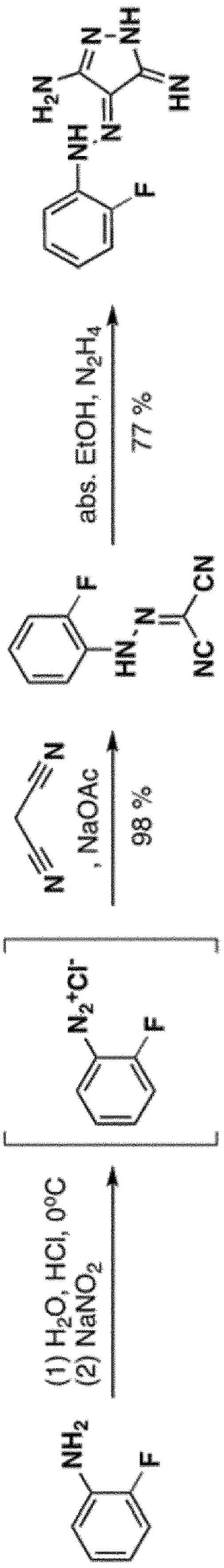
FIG. 2 shows the synthesis route of the H6-335-P1, i.e. 4-[(2-fluorophenyl) hydrazinylidene]pyrazole-3,5-diamine.

The synthesis route of the H6-335-P1 compound (FIG. 2) developed by the inventors is highly efficient (yield 77%) as the target molecule can be generated in few steps from readily available starting materials.

General Procedure B2—Cyclization with Hydrazine/Hydrazide

The product from procedure A1→3 (1 eq) was dissolved in EtOH (2.9 mL/mmol), followed by addition of the appropriate hydrazine/hydrazide derivative (1.2 eq). The reaction was refluxed until completion of the reaction. Afterwards the mixture was cooled to room temperature, and the precipitated product isolated by filtration. For those compounds that did not precipitate, the solvent and hydrazide was removed by evaporation under vacuum to give the product. If purification was needed, it was done with either flash chromatography or preparative HPLC.

General Procedure B3—Cyclization with Hydroxylamine

The product from procedure A1→3 (1 eq) was dissolved in methanol (6.5 mL/mmol) and added a solution of 10%

NaOtBu in methanol (0.5 mL/mmol), followed by hydroxylamine (1.2 eq). The mixture was re-fluxed overnight. The solvent was removed in vacuo and afterwards purified by flash chromatography or preparative HPLC.

General Procedure C1—Salt Formation with Acid

The product from procedure B1(ID2)(1 eq) was dissolved in 1,4-dioxane (10 mL/mmol), followed by acid (5 eq). The mixture stirred overnight, and the precipitate product isolated by filtration.

General Procedure C2—Salt Formation with Base

The product from procedure B1(CUJ-15) (1 eq) was dissolved in dry THF (5.3 mL/mmol) and cooled to 0° C., followed by base (1 eq). The mixture stirred overnight, and was concentrated in vacou.

The following compounds of Table 1 were synthesized by one or more of the above General Procedures A1-A3, B1-B3 and C1-C2.

TABLE 1

| Compound | Synthesis method, NMR characteristics and % yield |
|---|---|
| 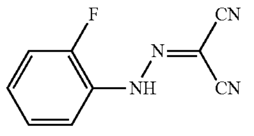<br>(Intermediate) | General Procedure A1<br>$^{1}H$ NMR (400 MHz, DMSO-$d_6$): δ 7.56-7.46 (m, 1H), 7.41-7.29 (m, 1H), 7.34-7.21 (m, 2H), NH proton not observed.<br>$^{13}C$ NMR (100 MHz, DMSO-$d_6$): δ 157.5 (d, J = 253.1 Hz), 127.9, 125.73, 125.70, 120.9, 117.2, 117.0, 110.4, 84.4.<br>Yield: 98% |
| 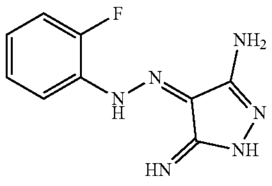<br>(H6-335-P1)<br>(4-[(2-fluorophenyl)hydrazinylidene]pyrazole-3,5-diamine) | General procedure B1<br>$^{1}H$ NMR (400 MHz, DMSO-$d_6$): δ 7.80 (m, 1H), 7.32-7.13 (m, 3H), 6.45 (s, 2H), 6.02 (s, 2H), NH protons not observed.<br>$^{13}C$ NMR (100 MHz, DMSO-$d_6$): δ 157.48 (d, J = 248.8 Hz), 141.79 (d, J = 6.4 Hz), 127.77 (d, J = 7.9 Hz), 124.84 (d, J = 3.6 Hz), 117.30, 116.69 (d, J = 19.6 Hz), 116.33.<br>Yield: 84% |
| 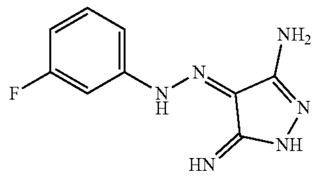<br>(H6-335)<br>The library compound<br>(4-[(3-fluorophenyl)hydrazinylidene]pyrazole-3,5-diamine) | General procedure A1 followed by B1<br>$^{1}H$ NMR (400 MHz, DMSO-$d_6$): δ 10.79 (s, 1H), 7.53 (dt, J = 11.2, 2.2 Hz, 1H), 7.49 (dt, J = 8.0, 1.3 Hz, 1H), 7.40 (td, J = 8.0, 6.3 Hz, 1H), 7.00 (tdd, J = 8.4, 2.7, 1.0 Hz, 1H), 6.44 (s, 1H), 5.90 (s, 1H), 5.27 (s, 1H).<br>$^{13}C$ NMR (100 MHz, DMSO-$d_6$): δ 163.52 (d, J = 242.9 Hz), 156.28 (d, J = 7.1 Hz), 130.70 (d, J = 9.2 Hz), 118.77, 115.07, 113.14 (d, J = 22.1 Hz), 105.50 (d, J = 22.5 Hz).<br>Yield: 81% |
| 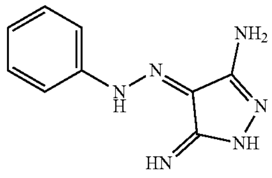<br>(H6-335 —SAR compound-1)<br>(4-[phenylhydrazinylidene]pyrazole-3,5-diamine) | General procedure A1 followed by B1<br>$^{1}H$ NMR (400 MHz, DMSO-$d_6$): δ 10.73 (s, 1H), 7.67 (dd, J = 8.3, 1.4 Hz, 2H), 7.39 (t, J = 7.8 Hz, 2H), 7.25-7.16 (m, 1H), 6.29 (s, 1H), 5.84 (s, 1H), 5.16 (s, 1H).<br>$^{13}C$ NMR (100 MHz, DMSO-$d_6$): δ 153.53, 128.77, 126.57, 120.46, 114.20.<br>Yield: 76% |
| 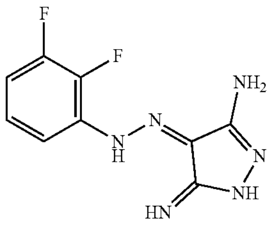<br>(H6-335 —SAR compound-2)<br>(4-[(2,3-difluorophenyl)hydrazin-ylidene]pyrazole-3,5-diamine) | General procedure A1 followed by B1<br>$^{1}H$ NMR (400 MHz, DMSO-$d_6$): δ 10.89 (s, 1H), 7.68-7.59 (m, 1H), 7.26-7.10 (m, 2H), 6.67 (s, 1H), 6.08 (s, 2H), 5.46 (s, 1H)<br>$^{13}C$ NMR (100 MHz, DMSO-$d_6$): δ 151.08 (dd, J = 243.5, 11.3 Hz), 145.29 (dd, J = 250.2, 13.5 Hz), 143.73 (dd, J = 3.6, 1.5 Hz), 124.29 (dd, J = 8.0, 4.8 Hz), 116.92, 114.13 (d, J = 17.2 Hz), 112.76 (d, J = 3.1 Hz).<br>Yield: 83% |

TABLE 1-continued

| Compound | Synthesis method, NMR characteristics and % yield |
|---|---|
| 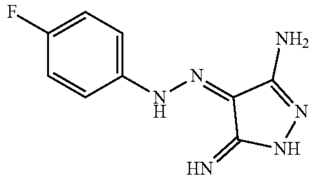<br>(H6-335 —SAR compound-3)<br>(4-[(4-fluorophenyl)hydrazin-ylidene]pyrazole-3,5-diamine) | General procedure A1 followed by B1<br>$^{1}$H NMR (400 MHz, DMSO-$d_6$): δ 10.92 (s, 1H), 7.96 (d, J = 8.2 Hz, 1H), 7.70 (dd, J = 7.9, 1.5 Hz, 1H), 7.63 (td, J = 7.8, 1.4 Hz, 1H), 7.33 (t, J = 7.6 Hz, 1H), 6.60 (s, 1H), 6.04 (s, 1H), 5.37 (s, 1H).<br>$^{13}$C NMR (100 MHz, DMSO-$d_6$): δ 151.38 (d, J = 243.2 Hz), 133.40 (d, J = 3.6 Hz), 126.17, 116.89 (d, J = 21.3 Hz), 116.27 (d, J = 6.9 Hz).<br>Yield: 87% |
| 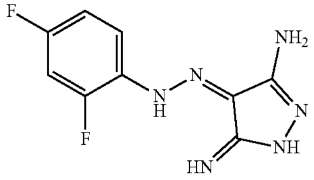<br>(H6-335 —SAR compound-4)<br>(4-[(2,4-difluorophenyl)hydrazin-ylidene]pyrazole-3,5-diamine) | General procedure A1 followed by B1<br>$^{1}$H NMR (400 MHz, DMSO-$d_6$): δ 10.84 (s, 2H), 7.85 (td, J = 9.1, 6.4 Hz, 2H), 7.30 (ddd, J = 11.7, 9.2, 2.8 Hz, 2H), 7.18 (s, 1H), 7.08 (dddd, J = 9.3, 8.2, 2.8, 1.3 Hz, 2H), 6.46 (s, 2H), 5.90 (s, 3H).<br>$^{13}$C NMR (100 MHz, DMSO-$d_6$): δ 160.79 (dd, J = 245.5, 11.7 Hz), 157.18 (dd, J = 251.9, 12.3 Hz), 138.90 (dd, J = 6.7, 3.7 Hz), 118.32 (dd, J = 9.5, 2.7 Hz), 116.12, 111.99 (dd, J = 22.1, 3.6 Hz), 104.94 (dd, J = 26.5, 24.1 Hz).<br>Yield: 72% |
| 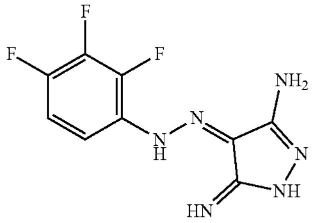<br>(H6-335 —SAR compound-5)<br>(4-[(2,3,4-trifluorophenyl)hydrazin-ylidene]pyrazole-3,5-diamine) | General procedure A1 followed by B1<br>$^{1}$H NMR (400 MHz, DMSO-$d_6$): δ 10.80 (s, 1H), 7.72-7.61 (m, 1H), 7.36-7.22 (m, 1H), 6.29 (s, 4H).<br>Due to low electron density of the polyfluorinated compound, it was not possible to obtain a good quality $^{13}$C NMR spectrum.<br>Yield: 56% |
| 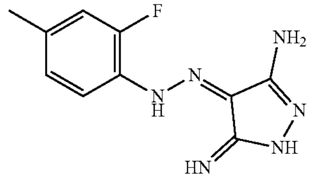<br>(H6-335 —SAR compound-6)<br>(4-[(2-fluoro,4-methylphenyl)hydrazin-ylidene]pyrazole-3,5-diamine) | General procedure A1 followed by B1<br>$^{1}$H NMR (400 MHz, DMSO-$d_6$): δ 10.80 (s, 1H), 7.70 (t, J = 8.4 Hz, 1H), 7.09 (dd, J = 12.4, 1.8 Hz, 1H), 6.99 (dd, J = 8.4, 1.8 Hz, 1H), 6.37 (s, 1H), 5.90 (s, 1H), 5.22 (s, 1H), 2.32 (s, 3H).<br>$^{13}$C NMR (100 MHz, DMSO-$d_6$): δ 157.35 (d, J = 249.0 Hz), 139.44 (d, J = 6.7 Hz), 138.15 (d, J = 7.7 Hz), 125.50, 116.99 (d, J = 19.5 Hz), 116.97, 115.82, 21.07.<br>Yield: 51% |
| 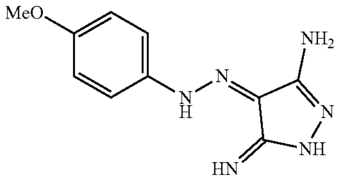<br>(H6-335 —SAR compound-7)<br>(4-[(4-methoxyphenyl)hydrazin-ylidene]pyrazole-3,5-diamine) | General procedure A1 followed by B1<br>$^{1}$H NMR (400 MHz, DMSO-$d_6$): δ 10.65 (s, 1H), 7.69-7.60 (m, 2H), 7.00-6.92 (m, 2H), 3.79 (s, 3H).<br>$^{13}$C NMR (100 MHz, DMSO-$d_6$): δ 158.86, 148.05, 122.16, 114.45, 113.84, 55.75.<br>Yield: 64% |
| 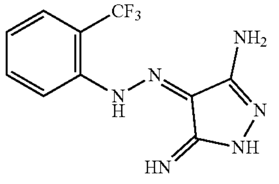<br>(H6-335 —SAR compound-8)<br>(4-[(2-(trifluoromethyl)phenyl)hydrazin-ylidene]pyrazole-3,5-diamine) | General procedure A1 followed by B1<br>$^{1}$H NMR (400 MHz, DMSO-$d_6$): δ 7.82 (m, 1H), 7.41-7.22 (m, 3H), 6.63 (s, 2H), 6.20 (s, 2H), NH protons not observed.<br>Yield: 78% |

TABLE 1-continued

| Compound | Synthesis method, NMR characteristics and % yield |
| --- | --- |
| 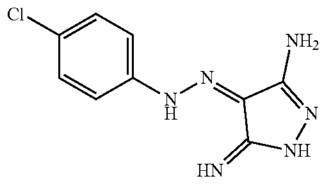<br>(H6-335 —SAR compound-9)<br>(4-[(4-chlorophenyl)hydrazin-ylidene]pyrazole-3,5-diamine) | General procedure A1 followed by B1<br>$^{1}H$ NMR (400 MHz, DMSO-$d_6$): δ 10.47 (s, 1H), 7.71-7.59 (m, 2H), 7.01-6.95 (m, 2H)<br>$^{13}C$ NMR (100 MHz, DMSO-$d_6$): δ 147.33, 134.67, 130.24, 128.26, 126.73.<br>Yield: 77% |
| 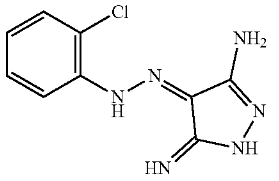<br>(H6-335 —SAR compound-10)<br>(4-[(2-chlorophenyl)hydrazin-ylidene]pyrazole-3,5-diamine) | General procedure A1 followed by B1<br>$^{1}H$ NMR (400 MHz, DMSO-$d_6$): δ 10.88 (s, 1H), 7.84 (d, J = 8.1, 1H), 7.50 (d, J = 8.0, 1H), 7.33 (t, J = 7.6 Hz, 1H), 7.23-7.15 (m, 1H), 6.52 (s, 1H), 6.11 (s, 1H), 5.31 (s, 1H).<br>$^{13}C$ NMR (100 MHz, DMSO-$d_6$): δ 149.39, 130.31, 127.92, 127.68, 117.05, 116.79.<br>Yield: 55% |
| 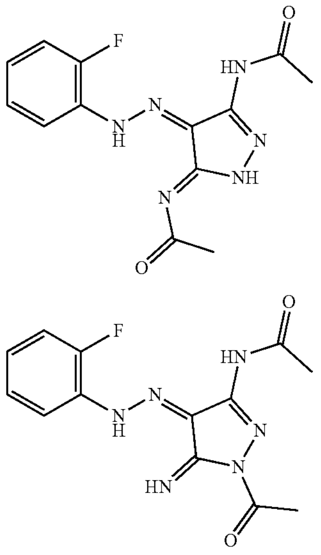<br>(H6-335 —SAR compound-11)<br>(Di-acetylatet H6 335-P1) | Procedure for acetylation<br>(E)-4-(2-(2-fluorophenyl)hydrazineylidene)-5-imino-4,5-dihydro-1H-pyrazol-3-amine (255.8 mg, 1.16 mmol, 1 eq) was added to a solution of sodium acetate (0.46 mg/mmol) in acetic anhydride (22 eq.) and heated to 100° C. until full conversion. The mixture was poured into an ice-water mixture (100 mL), resulting in precipitation of the product. The product was isolated by filtration, followed by recrystallization in ethanol to give the product mixture as black needles, yield 175.8 mg.<br>Initial biological testing was performed on the mixture.<br>$^{1}H$ NMR (400 MHz, DMSO-$d_6$): δ 8.39 (s, 0H), 8.34 (s, 2H), 7.93-7.80 (m, 0H), 7.71 (td, J = 8.0, 1.7 Hz, 1H), 7.62-7.21 (m, 4H), 2.89 (s, 0H), 2.76-2.69 (m, 0H), 2.58 (s, 3H), 2.54 (s, 1H), 2.32 (s, 6H), 2.29 (d, J = 2.8 Hz, 1H), 2.19 (d, J = 6.1 Hz, 1H).<br>$^{13}C$ NMR (100 MHz, DMSO-$d_6$): δ 173.53, 173.45, 172.02, 159.74, 157.23, 140.86, 140.79, 131.33, 131.25, 125.22, 125.19, 117.83, 117.41, 117.33, 117.13, 117.00, 26.02, 25.96, 23.36, 23.26.<br>Yield: 50% |
| 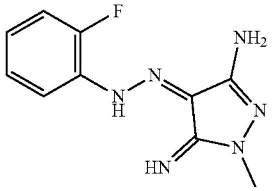<br>(H6-335 —SAR compound-12)<br>(4-[(2-fluorophenyl)hydrazinylidene]-1-methylpyrazole-3,5-diamine) | General procedure A1 followed by B1<br>$1^{H}$ NMR (400 MHz, DMSO-$d_6$): δ 7.83 (d, J = 10.1 Hz, 1H), 7.37-7.32 (m, 1H), 7.31-7.17 (m, 3H), 7.22-7.13 (m, 1H), 6.64 (s, 2H), 6.06 (s, 2H), 5.38 (s, 1H), 3.38 (s, 4H), 2.54-2.47 (m, 1H).<br>$^{13}C$ NMR (100 MHz, DMSO-$d_6$): δ 158.69, 141.79, 127.80, 124.84, 117.33, 116.79, 116.60, 116.20, 34.25.<br>Yield: 71% |

TABLE 1-continued

| Compound | Synthesis method, NMR characteristics and % yield |
|---|---|
| 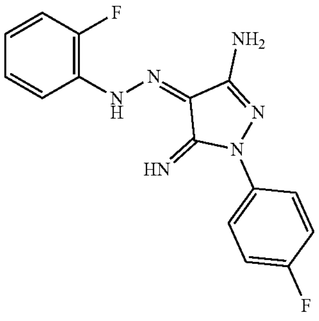<br>(H6-335 —SAR compound-13)<br>(4-[(2-fluorophenyl)hydrazinylidene]-1-(4-fluorophenyl)pyrazole-3,5-diamine) | General procedure A1 followed by B2<br>$^1$H NMR (400 MHz, DMSO-$d_6$): δ 7.91 (s, 1H), 7.66-7.51 (m, 2H), 7.44-7.14 (m, 6H), 6.90 (s, 1H), 6.25 (s, 1H), 5.75 (s, 1H).<br>$^{13}$C NMR (100 MHz, DMSO-$d_6$): δ 160.54 (d, J = 243.4 Hz), 157.72 (d, J = 249.7 Hz), 141.47, 128.57 (d, J = 7.9 Hz), 125.14 (d, J = 9.0 Hz), 124.95 (d, J = 3.5 Hz), 117.49, 116.81 (d, J = 19.5 Hz), 116.57, 116.53 (d, J = 22.8 Hz).<br>Yield: 47% |
| 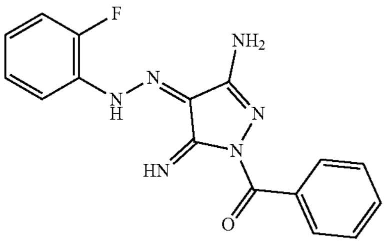<br>(H6-335 —SAR compound-14)<br>(4-[(2-fluorophenyl)hydrazinylidene]-1-benzoylpyrazole-3,5-diamine) | General procedure A1 followed by B2<br>$^1$H NMR (400 MHz, DMSO-$d_6$): δ 8.52 (s, 1H), 8.02-7.89 (m, 3H), 7.68-7.57 (m, 1H), 7.56-7.48 (m, 2H), 7.45-7.31 (m, 2H), 7.30-7.21 (m, 1H), 6.34 (s, 2H).<br>$^{13}$C NMR (100 MHz, DMSO-$d_6$): δ 169.47, 158.05 (d, J = 250.9 Hz), 141.13 (d, J = 6.4 Hz), 133.62, 132.37, 130.58, 129.81 (d, J = 8.0 Hz), 128.21, 125.06 (d, J = 3.6 Hz), 117.57, 117.01 (d, J = 19.5 Hz), 115.19.<br>Yield: 47% |
| 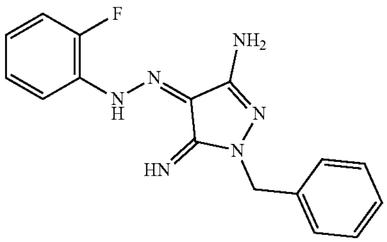<br>(H6-335 —SAR compound-15)<br>(4-[(2-fluorophenyl)hydrazinylidene]-1-benzylpyrazole-3,5-diamine) | General procedure A1 followed by B2<br>$^1$H NMR (400 MHz, DMSO-$d_6$): δ 7.83 (s, 2H), 7.42-7.11 (m, 9H), 6.86 (s, 1H), 6.09 (s, 1H), 5.43 (s, 1H), 4.98 (s, 2H).<br>$^{13}$C NMR (100 MHz, DMSO-$d_6$): δ 157.50 (d, J = 249.7 Hz), 148.92, 147.12, 141.75, 137.68, 128.84, 127.88 (d, J = 7.25 Hz), 127.71, 124.84, 117.37, 116.72 (d, J = 19.5 Hz), 116.13.<br>Yield: 70% |
| 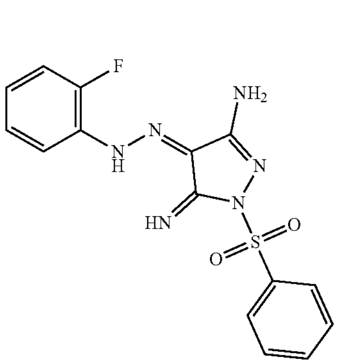<br>(H6-335 —SAR compound-16)<br>(4-[(2-fluorophenyl)hydrazinylidene]-1-(phenylsulfonyl)pyrazole-3,5-diamine) | General procedure A1 followed by B1<br>$^1$H NMR (400 MHz, DMSO-$d_6$): δ 8.06 (s, 1H), 7.96-7.74 (m, 3H), 7.73-7.57 (m, 2H), 7.38-7.17 (m, 4H), 6.30 (s, 2H).<br>$^{13}$C NMR (100 MHz, DMSO-$d_6$): δ 158.11 (d, J = 251.4 Hz), 140.77 (d, J = 6.5 Hz), 136.52, 135.33, 133.07, 130.25 (d, J = 8.6 Hz), 129.47, 127.96 (d, J = 13.7 Hz), 125.05 (d, J = 3.6 Hz), 117.52, 117.02 (d, J = 19.5 Hz), 114.89.<br>Yield: 81% |

TABLE 1-continued

| Compound | Synthesis method, NMR characteristics and % yield |
|---|---|
| 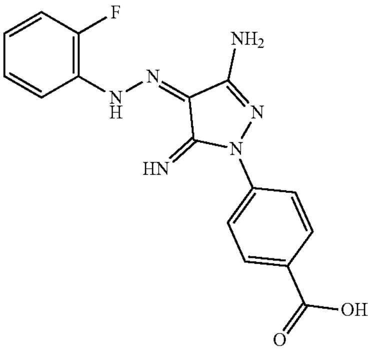<br>(H6-335 —SAR compound-17)<br>(4-[(2-fluorophenyl)hydrazinylidene]-1-(4-(carboxylic acid)phenyl)pyrazole-3,5-diamine) | General procedure A1 followed by B2<br>$^{1}$H NMR (400 MHz, DMSO-$d_6$): δ 12.81 (s, 1H), 8.09-7.94 (m, 3H), 7.77-7.68 (m, 2H), 7.43-6.95 (m, 3H), 6.28 (s, 1H), 5.98 (s, 1H).<br>$^{13}$C NMR (100 MHz, DMSO-$d_6$): δ 167.20, 157.82 (d, J = 250.2 Hz), 142.42, 141.35, 131.00, 128.89 (d, J = 8.1 Hz), 127.86, 124.96 (d, J = 3.65 Hz), 121.51, 117.52, 116.88 (d, J = 15.3 Hz), 116.77.<br>Yield: 81% |
| 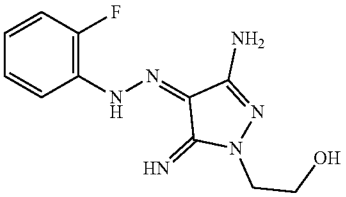<br>(H6-335 —SAR compound-18) | General procedure A1 followed by B2<br>$^{1}$H NMR (400 MHz, DMSO-$d_6$): δ 7.83 (s, 1H), 7.36-7.13 (m, 4H), 6.57 (s, 1H), 6.08 (s, 1H), 5.40 (s, 1H), 4.89 (t, J = 5.2 Hz, 1H), 3.78 (d, J = 6.2 Hz, 2H), 3.67 (q, J = 5.6 Hz, 2H).<br>$^{13}$C NMR (100 MHz, DMSO-$d_6$): δ 157.45 (d, J = 249.0 Hz), 149.06, 146.49, 141.80, 127.74 (d, J = 7.8 Hz), 124.84, 117.34, 116.68 (d, J = 19.6 Hz), 116.32, 59.45, 49.17.<br>Yield: 87% |
| 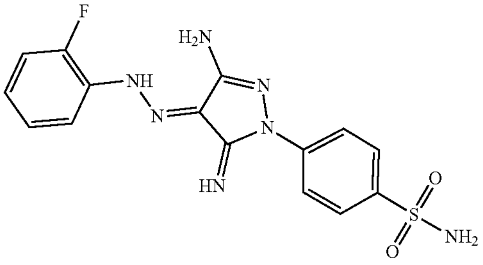<br>(H6-335 —SAR compound-19)<br>(4-[(2-fluorophenyl)hydrazinylidene]-1-(4-sulfonamidophenyl)pyrazole-3,5-diamine) | General procedure A1 followed by B2<br>$^{1}$H NMR (400 MHz, DMSO-$d_6$): δ 10.46 (s, 2H), 8.88 (s, 1H), 7.97-7.88 (m, 1H), 7.81-7.74 (m, 1H), 7.74-7.67 (m, 2H), 7.46 (s, 1H), 7.37-7.20 (m, 1H), 7.20 (s, 2H), 7.08-7.00 (m, 2H).<br>$^{13}$C NMR (100 MHz, DMSO-$d_6$): δ 157.81 (d, J = 249.9 Hz), 148.88, 141.35 (d, J = 6.8 Hz), 141.23, 136.59, 128.94 (d, J = 7.9 Hz), 127.38 (d, J = 2.1 Hz), 124.99 (d, J = 3.5 Hz), 121.97, 117.52, 116.97, 116.74 (d, J = 6.2 Hz), 113.74.<br>Yield: Quant. |
| 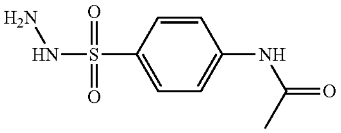<br>(Intermediate) | 4-acetamidobenzenesulfonyl chloride (3g, 12.84 mmol, 1 eq.) was dissolved in DCM (1.95 mL/mmol) and hydrazine hydrate (50%, 5 eq.) was added under nitrogen. The reaction was followed by TLC and upon completion, the product was isolated by filtration and dried under vacuum.<br>$^{1}$H NMR (400 MHz, DMSO-$d_6$): δ 10.40 (s, 1H), 8.24 (s, 1H), 7.82-7.66 (m, 4H), 7.52 (s, 1H), 4.04 (s, 2H), 2.09 (s, 3H).<br>$^{13}$C NMR (100 MHz, DMSO-$d_6$): δ 169.50, 143.49, 132.03, 129.22, 118.93, 24.60.<br>Yield: 52% |
| 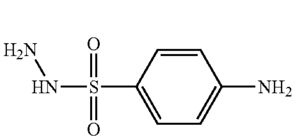<br>(Intermediate) | N-(4-(hydrazineylsulfonyl)phenyl) acetamide (923.7 mg, 4.03 mmol, 1 eq.) was dissolved in 40 wt% NaOH (40 ml) and refluxed until LCMS showed completion. When the reaction was complete, the cooled mixture was added ethyl acetate and made slightly acidic with conc. HCl before extraction. The organic phase was evaporated and used as crude salt without further purification.<br>$^{1}$H NMR (400 MHz, Deuterium Oxide) : δ 7.72-7.62 (m, 2H), 7.52-7.38 (m, 2H). NH proton not observed.<br>$^{13}$C NMR (100 MHz, Deuterium Oxide): δ 173.13, 140.95, 136.69, 128.08, 126.40, 121.37, 23.09.<br>Yield: Quant. |

TABLE 1-continued

| Compound | Synthesis method, NMR characteristics and % yield |
|---|---|
| 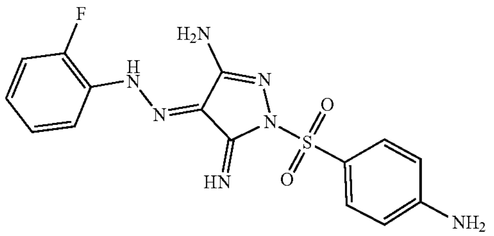 (H6-335 —SAR compound-20) (4-[(2-fluorophenyl)hydrazinylidene]-1-((4-aminophenyl)sulfonyl)pyrazole-3,5-diamine) | General procedure A1 followed by B1. $^{1}H$ NMR (400 MHz, Methanol-$d^{4}$) : δ 7.63-7.52 (m, 2H), 7.33-7.20 (m, 7H). NH proton not observed. $^{13}C$ NMR (100 MHz, Methanol-$d_4$): δ 152.31 (d, J = 247.7 Hz), 129.20 (d, J = 9.5 Hz), 126.94 (d, J = 7.4 Hz), 124.98 (d, J = 3.7 Hz), 118.90, 115.93 (d, J = 18.7 Hz), 112.83, 108.22. Yield: 28% |
| 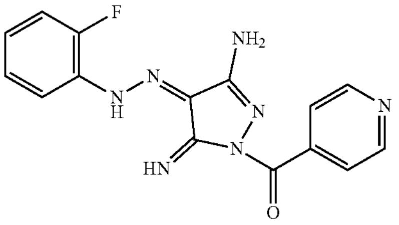 (H6-335 —SAR compound-21) (4-[(2-fluorophenyl)hydrazinylidene]-1-(pyridin-4-yl-methanone)pyrazole-3,5-diamine) | General procedure A1 followed by B1 $^{1}H$ NMR (400 MHz, DMSO-$d_6$): δ 8.80-8.74 (m, 2H), 8.54 (s, 1H), 7.97-7.89 (m, 1H), 7.85-7.79 (m, 2H), 7.45-7.20 (m, 4H), 7.04 (s, 1H), 6.42 (s, 1H). $^{13}C$ NMR (100 MHz, DMSO-$d_6$): δ 167.85, 158.09 (d, J = 251.1 Hz), 153.03, 150.03, 141.23, 141.05 (d, J = 6.3 Hz), 130.00 (d, J = 8.1 Hz), 123.53, 118.17, 117.56, 117.03 (d, J = 19.5 Hz), 115.14. Yield: 40% |
| 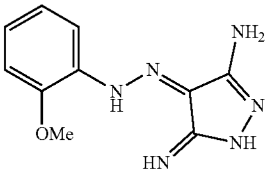 (H6-335 —SAR compound-22) (4-[(2-methoxyphenyl)hydrazin-ylidene]pyrazole-3,5-diamine) | General procedure A1 followed by B1 $^{1}H$ NMR (400 MHz, DMSO-$d_6$): δ 7.65 (dd, J = 8.0, 1.7 Hz, 1H), 7.24-7.11 (m, 1H), 7.14-7.05 (m, 1H), 6.97-6.89 (m, 1H), 5.80 (s, 0H), 3.86 (s, 3H). NH protons not observed. $^{13}C$ NMR (100 MHz, DMSO-$d_6$): δ 155.21, 154.60, 153.01, 142.69, 128.14, 120.88, 115.78, 113.05, 56.29. Yield: 33% |
| 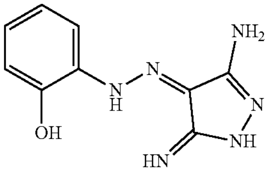 (H6-335 —SAR compound-23) (4-[(2-hydroxyphenyl)hydrazin-ylidene]pyrazole-3,5-diamine) | General procedure A1 followed by B1 $^{1}H$ NMR (400 MHz, DMSO-$d_6$): δ 10.71 (s, 1H), 10.28 (s, 1H), 7.62 (dd, J = 7.9, 1.7 Hz, 1H), 7.13-7.02 (m, 1H), 6.94-6.79 (m, 1H), 6.04 (s, 3H). $^{13}C$ NMR (100 MHz, DMSO-$d_6$): δ 152.02, 139.79, 135.81, 128.18, 122.01, 119.71, 117.53, 113.92. Yield: 30% |
| 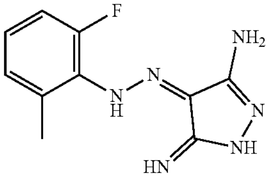 (H6-335 —SAR compound-24) (4-[(2-fluor-6-methylphenyl)hydrazin-ylidene]pyrazole-3,5-diamine) | General procedure A1 followed by B1 $^{1}H$ NMR (400 MHz, DMSO-$d_6$): δ 7.29-7.16 (m, 1H), 7.21-7.13 (m, 1H), 7.18-7.08 (m, 2H), 7.09 (d, J = 2.8 Hz, 2H), 7.11-7.00 (m, 4H), 7.04-6.93 (m, 2H), 2.44 (s, 2H), 2.40 (s, 2H), 2.40-2.30 (m, 1H), 2.32 (s, 6H), 2.23 (s, 2H). $^{13}C$ NMR (100 MHz, DMSO-$d_6$): δ 155.66, 153.19, 141.37, 141.29, 134.13, 133.77, 133.40, 127.36, 126.86, 126.82, 126.78, 126.51, 126.48, 116.92, 115.03, 114.64, 114.42, 114.21, 114.01, 19.22, 18.86, 18.83, 18.25, 18.22. Yield: 86% |

TABLE 1-continued

| Compound | Synthesis method, NMR characteristics and % yield |
| --- | --- |
| 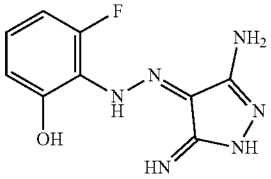 (H6-335 —SAR compound-25) (4-[(2-fluor-6-hydroxyphenyl)hydrazin-ylidene]pyrazole-3,5-diamine) | General procedure A1 followed by B1 $^{1}H$ NMR (400 MHz, DMSO-$d_6$): δ 11.68 (s, 1H), 10.93 (s, 1H), 7.13-7.03 (m, 1H), 6.82-6.72 (m, 1H), 6.72-6.65 (m, 1H), 6.14 (s, 2H). $^{13}C$ NMR (100 MHz, DMSO-$d_6$): δ 158.27 (d, J = 249.1 Hz), 152.26 (d, J = 2.2 Hz), 128.21 (d, J = 10.7 Hz), 126.75 (d, J = 8.2 Hz), 114.39, 113.59 (d, J = 3.1 Hz), 106.73 (d, J = 20.1 Hz). Yield: 25% |
| 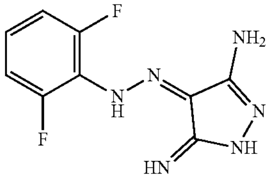 (H6-335 —SAR compound-26) (4-[(2,6-difluorophenyl)hydrazin-ylidene]pyrazole-3,5-diamine) | General procedure A1 followed by B1 $^{1}H$ NMR (400 MHz, DMSO-$d_6$): δ 10.90-10.84 (m, 2H), 7.26-7.17 (m, 1H), 7.22-7.06 (m, 4H), 6.10 (s, 4H), 3.35 (s, 1H), 2.53 (s, 1H). $^{13}C$ NMR (100 MHz, DMSO-$d_6$): δ 155.41 (dd, J = 250.7, 5.6 Hz), 132.35 (t, J = 11.0 Hz), 126.51 (t, J = 10.0 Hz), 117.24, 112.70 (dd, 18.1, 5.6 Hz). Yield: 51% |
| 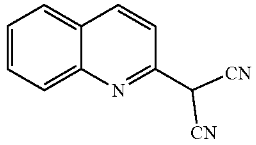 (Intermediate) | In a dry round bottom flask was added malonitrile (1.7 eq) to a solution of NaH (4.5 eq, 60% in oil) in HMPA (2.1 mL/mmol quinoline). The solution was cooled in an ice bath for 30 min before addition of 2-bromoquinoline (1 eq), afterwards the reaction was allowed to heat to rt before being heated to 1000C until full conversion. The reaction was poured into ice/water (80 mL) and neutralized with acetic acid. The precipitate was isolated by vacuum filtration and washed with toluene. The crude product was used without further purification. $^{1}H$ NMR (400 MHz, DMSO-$d_6$): δ 12.61 (s, 1H), 8.11 (d, J = 9.3 Hz, 1H), 7.92 (d, J = 8.4 Hz, 1H), 7.81 (dd, J = 7.9, 1.4 Hz, 1H), 7.75-7.50 (m, 2H), 7.41 (ddd, J = 8.2, 7.2, 1.1 Hz, 1H), 7.16 (d, J = 9.3 Hz, 1H), 3.43 (s, H1). $^{13}C$ NMR (100 MHz, DMSO-$d_6$): δ 161.36, 147.82, 134.67, 129.87, 128.32, 127.84, 126.73, 125.92, 122.04, 111.74. Yield: Quant. |
| 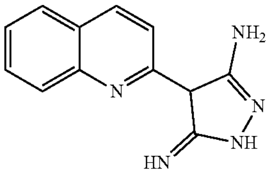 (H6-335 —SAR compound-27) 4-(quinolin-2-yl)pyrazole-3,5-diamine | General procedure B2 $^{1}H$ NMR (400 MHz, DMSO-$d_6$): δ 10.64 (s, 1H), 8.14 (d, J = 8.9 Hz, 1H), 7.85-7.76 (m, 3H), 7.69-7.58 (m, 1H), 7.38 (t, J = 7.4 Hz, 1H), 5.69 (s, 3H). $^{13}C$ NMR (100 MHz, DMSO-$d_6$): δ 155.93, 147.55, 135.78, 129.70, 127.95, 127.67, 125.04, 124.34, 119.23, 90.47. Yield: 3% |
| 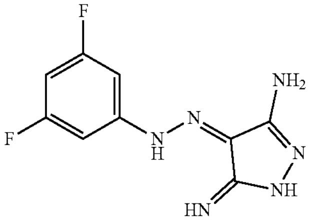 (H6-335 —SAR compound-28) (4-[(3,5-difluorophenyl)hydrazin-ylidene]pyrazole-3,5-diamine) | General procedure A1 followed by B1 $^{1}H$ NMR (400 MHz, DMSO-$d_6$): δ 10.86 (s, 1H), 7.45-7.35 (m, 2H), 7.01-6.91 (m, 1H), 6.61 (s, 1H), 5.97 (s, 1H), 5.36 (s, 1H). Due to low electron density of the polyfluorinated compound, it was not possible to obtain a good quality $^{13}C$ NMR spectrum. Yield: 23% |

TABLE 1-continued

| Compound | Synthesis method, NMR characteristics and % yield |
|---|---|
| 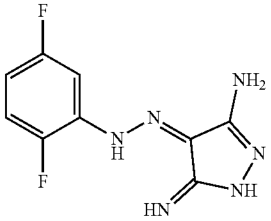 (H6-335 —SAR compound-29) (4-[(2,5-difluorophenyl)hydrazin-ylidene]pyrazole-3,5-diamine) | General procedure A1 followed by B1<br>$^{1}$H NMR (400 MHz, DMSO-$d_6$): δ 10.93 (s, 7.30 (ddd, J = 10.7, 9.0, 4.9 Hz, 1H), 7.01 (ddt, J = 9.0, 7.2, 3.5 Hz, 1H), 6.43 (s, 3H), 6.27 (s, 1H).<br>$^{13}$C NMR (100 MHz, DMSO-$d_6$): δ 10.93 (s, 1H), 7.68 (ddd, J = 10.0, 6.4, 3.3 Hz, 1H), 7.30 (ddd, J = 10.6, 9.0, 4.9 Hz, 1H), 7.05-6.95 (m, 1H), 6.47 (s, 2H), 6.25 (s, 2H).<br>Yield: 73% |
| 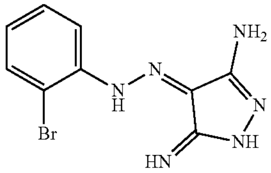 (H6-335 —SAR compound-30) (4-[(2-bromophenyl)hydrazin-ylidene]pyrazole-3,5-diamine) | General procedure A1 followed by B1<br>$^{1}$H NMR (400 MHz, DMSO-$d_6$): δ 10.90 (s, 1H), 7.82 (ddd, J = 10.0, 8.0, 1.5 Hz, 1H), 7.67 (dd, J = 7.9, 1.4 Hz, 1H), 7.37 (td, J = 8.3, 7.7, 1.4 Hz, 1H), 7.12 (td, J = 7.6, 1.7 Hz, 1H), 6.67 (s, 1H), 6.04 (s, 1H), 1H), 7.67 (ddd, J = 10.0, 6.4, 3.3 Hz, 1H).<br>$^{13}$C NMR (100 MHz, DMSO-$d_6$): δ 152.76, 150.25, 133.29, 128.53, 128.09, 121.58, 117.26, 116.64.<br>Yield: Quant. |
| 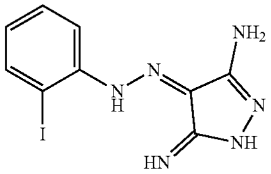 (H6-335 —SAR compound-31) (4-[(2-iodophenyl)hydrazin-ylidene]pyrazole-3,5-diamine) | General procedure A1 followed by B1<br>$^{1}$H NMR (400 MHz, DMSO-$d_6$): δ 10.84 (s, 1H), 7.90 (d, J = 7.8 Hz, 1H), 7.76 (dd, J = 8.2, 1.5 Hz, 1H), 7.38 (t, J = 7.6 Hz, 1H), 7.26 (s, 0H), 6.98 (td, J = 7.4, 1.6 Hz, 1H), 6.77-6.68 (m, 2H).<br>$^{13}$C NMR (100 MHz, DMSO-$d_6$): δ 152.31, 139.28, 129.22, 128.62, 116.82, 115.99, 99.73.<br>Yield: Quant. |
| 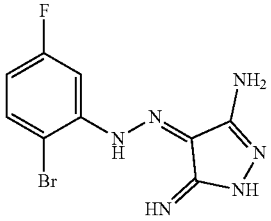 (H6-335 —SAR compound-32) (4-[(2-bromo-5-fluorophenyl)hydrazin-ylidene]pyrazole-3,5-diamine) | General procedure A1 followed by B1<br>$^{1}$H NMR (400 MHz, DMSO-$d_6$): δ 10.99 (s, 1H), 7.74-7.64 (m, 2H), 7.04-6.93 (m, 1H), 6.73 (s, 1H), 6.26 (s, 1H).<br>$^{13}$C NMR (100 MHz, DMSO-$d_6$): δ 162.81 (d, J = 244.5 Hz), 152.19 (d, J = 6.1 Hz), 134.34 (d, J = 8.8 Hz), 117.20, 115.65 (d, J = 2.9 Hz), 114.44 (d, J = 24.2 Hz), 103.74 (d, J = 24.6 Hz).<br>Yield: 98% |
| 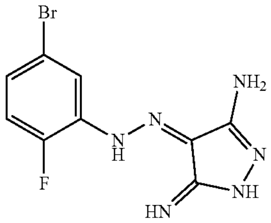 (H6-335 —SAR compound-33) (4-[(5-bromo-2-fluorophenyl)hydrazin-ylidene]pyrazole-3,5-diamine) | General procedure A1 followed by B1<br>$^{1}$H NMR (400 MHz, DMSO-$d_6$): δ 10.92 (s, 1H), 8.01 (dd, J = 7.2, 2.6 Hz, 1H), 7.38-7.29 (m, 1H), 7.29-7.20 (m, 1H), 6.75 (s, 2H), 6.10 (s, 3H)<br>$^{13}$C NMR (100 MHz, DMSO-$d_6$): δ 156.43 (d, J = 249.3 Hz), 143.09 (d, J = 7.6 Hz), 129.42 (d, J = 8.0 Hz), 119.79, 118.82 (d, J = 21.4 Hz), 117.53 (d, J = 3.2 Hz), 117.09.<br>Yield: 63% |

TABLE 1-continued

| Compound | Synthesis method, NMR characteristics and % yield |
|---|---|
| 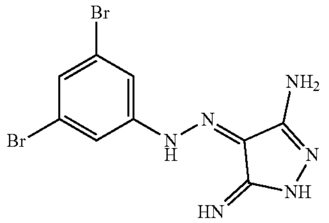 (H6-335 —SAR compound-34) (4-[(3,5-dibromophenyl)hydrazin-ylidene]pyrazole-3,5-diamine) | General procedure A1 followed by B1 $^{1}$H NMR (400 MHz, DMSO-$d_6$): δ 10.83 (s, 1H), 7.90 (d, J = 1.8 Hz, 2H), 7.54 (t, J = 1.8 Hz, 1H), 6.19 (s, 2H). $^{13}$C NMR (100 MHz, DMSO-$d_6$): δ 156.73, 130.21, 123.30, 122.57, 116.16. Yield: 91% |
| 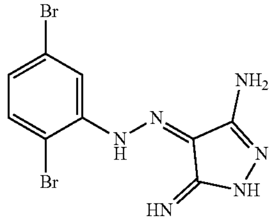 (H6-335 —SAR compound-35) (4-[(2,5-dibromophenyl)hydrazin-ylidene]pyrazole-3,5-diamine) | General procedure A1 followed by B1 $^{1}$H NMR (400 MHz, DMSO-$d_6$): δ 10.62 (s, 1H), 8.02 (d, J = 2.4 Hz, 1H), 7.60 (d, J = 8.4 Hz, 1H), 7.30-7.21 (m, 1H), 6.75 (s, 2H). $^{13}$C NMR (100 MHz, DMSO-$d_6$): δ 151.60, 134.81, 134.20, 129.72, 122.26, 119.93 (d, J = 5.2 Hz), 119.72, 117.59. Yield: 63% |
| 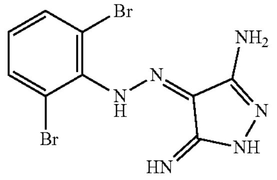 (H6-335 —SAR compound-36) (4-[(2,6-dibromophenyl)hydrazin-ylidene]pyrazole-3,5-diamine) | General procedure A1 followed by B1 $^{1}$H NMR (400 MHz, DMSO-$d_6$): δ 10.88 (s, 1H), 7.68 (d, J = 8.0 Hz, 2H), 7.03 (t, J = 7.9 Hz, 1H), 6.36 (s, 1H), 5.81 (s, 1H). $^{13}$C NMR (100 MHz, DMSO-$d_6$): δ 150.28, 133.19, 128.10, 116.97, 115.70. Yield: Quant. |
| 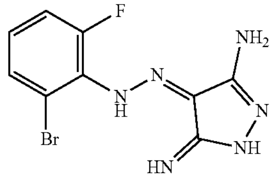 (H6-335 —SAR compound-37) (4-[(2-bromo, 6-fluorophenyl)hydrazin-ylidene]pyrazole-3,5-diamine) | General procedure A1 followed by B1 $^{1}$H NMR (400 MHz, DMSO-$d_6$): δ 10.91 (s, 1H), 7.52 (dt, J = 8.0, 1.3 Hz, 1H), 7.33-7.23 (m, 1H), 7.17-7.07 (m, 1H), 6.51 (s, 1H), 5.80 (s, 1H). $^{13}$C NMR (100 MHz, DMSO-$d_6$): δ 153.75 (d, J = 255.3 Hz), 140.78, 128.90 (d, J = 3.5 Hz), 127.39 (d, J = 8.8 Hz), 120.10 (d, J = 3.5 Hz), 117.07 (d, J = 2.1 Hz), 116.88. Yield: Quant. |
| 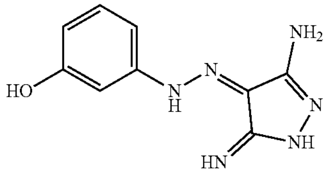 (H6-335 —SAR compound-38) (4-[(3-hydroxyphenyl)hydrazin-ylidene]pyrazole-3,5-diamine) | General procedure A1 followed by B1 $^{1}$H NMR (400 MHz, DMSO-$d_6$): δ 7.42 (s, 1H), 7.20-7.02 (m, 3H), 6.63 (ddd, J = 7.8, 2.5, 1.2 Hz, 1H), 6.29 (s, 1H). $^{13}$C NMR (100 MHz, DMSO-$d_6$): δ 173.43, 158.51, 155.44, 129.69, 114.52, 114.25, 112.59, 107.08. Yield: 34% |
| 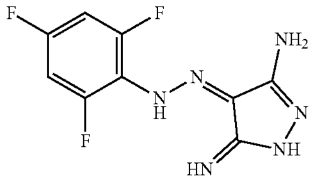 (H6-335 —SAR compound-39) (4-[(2,4,6-trifluorophenyl)hydrazin-ylidene]pyrazole-3,5-diamine) | General procedure A1 followed by B1 $^{1}$H NMR (400 MHz, DMSO-$d_6$): δ 12.06 (s, 1H), 7.29-7.16 (m, 1H), 6.82 (ddd, J = 11.7, 9.2, 2.8 Hz, 1H), 6.61 (ddd, J = 10.6, 2.8, 1.7 Hz, 1H), 6.37 (s, 2H), 6.16 (s, 2H), 5.80 (s, 1H). Due to low electron density of the polyfluorinated compound, it was not possible to obtain a good quality $^{13}$C NMR spectrum. Yield: 43% |

TABLE 1-continued

| Compound | Synthesis method, NMR characteristics and % yield |
|---|---|
| 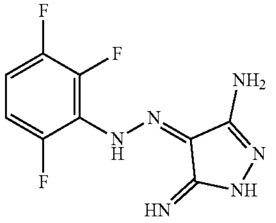 (H6-335 —SAR compound-40) (4-[(2,3,6-trifluorophenyl)hydrazin-ylidene]pyrazole-3,5-diamine) | General procedure A1 followed by B1<br>$^{1}H$ NMR (400 MHz, DMSO-$d_6$): δ 11.08 (s, 1H), 7.31-7.10 (m, 2H), 6.46 (s, 2H), 5.90 (s, 2H).<br>Due to low electron density of the polyfluorinated compound, it was not possible to obtain a good quality $^{13}C$ NMR spectrum.<br>Yield: 67% |
| 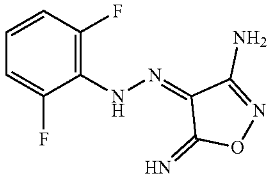 (H6-335 —SAR compound-41) (4-[(2,6-difluorophenyl)hydrazin-ylidene]-5-imino-4,5-dihydroisoxazol-3-amine) | General procedure A1 followed by B3<br>$^{1}H$ NMR (400 MHz, Methanol-$d_4$): δ 7.44-7.24 (m, 2H), 7.26 (s, 1H), 7.28-7.20 (m, 2H), 7.24-6.99 (m, 8H).<br>Due to low electron density of the polyfluorinated compound, it was not possible to obtain a good quality $^{13}C$ NMR spectrum.<br>Yield: 41% |
| 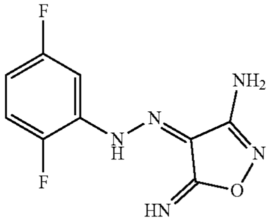 (H6-335 —SAR compound-42) 4-[(2,5-difluorophenyl)hydrazin-ylidene]-5-imino-4,5-dihydroisoxazol-3-amine | General procedure A1 followed by B3<br>$^{1}H$ NMR (400 MHz, Methanol-$d_4$): δ 7.61-7.52 (m, 1H), 7.29-7.18 (m, 1H), 7.11-6.99 (m, 1H).<br>$^{13}C$ NMR (100 MHz, Methanol-$d_4$): δ 159.20 (dd, J = 241.0, 2.0 Hz), 154.10 (dd, J = 246.7, 2.3 Hz), 142.33 (dd, J = 23.7, 8.9 Hz), 118.29 (dd, J = 22.6, 9.3 Hz), 115.26 (dd, J = 25.3, 8.2 Hz), 110.21, 103.71 (d, J = 25.6, 8.3 Hz).<br>Yield: 52% |
| 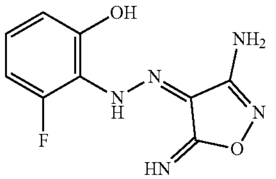 (H6-335 —SAR compound-43) (4-[(2-fluoro-6-hydroxyphenyl)hydrazin-ylidene]-5-imino-4,5-dihydroisoxazol-3-amine) | General procedure A1 followed by B3<br>$^{1}H$ NMR (400 MHz, Chloroform-d): δ 11.27 (s, 1H), 11.04 (q, J = 8.5, 7.7 Hz, 0H), 10.76 (s, 1H), 10.60 (dh, J = 17.5, 8.9, 8.3 Hz, 2H), 7.65 (s, 9H), 5.16 (s, 3H), 4.82-4.72 (m, 1H), 3.98 (d, J = 4.0 Hz, 4H).<br>$^{13}C$ NMR (100 MHz, Chloroform-d): δ 53.50, 53.29, 53.08, 52.87, 52.65, 52.44, 52.23, 4.82.<br>Yield: 2% |
| 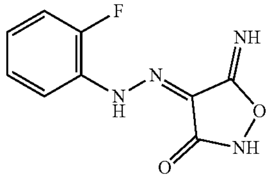 (H6-335 —SAR compound-44) (4-[(2-fluorophenyl)hydrazinylidene]-5-iminoisoxazolidin-3-one) | General procedure A2 followed by B3<br>$^{1}H$ NMR (400 MHz, Methanol-$d_4$): δ 7.89 (td, J = 7.9, 1.5 Hz, 1H), 7.34-7.22 (m, 3H). NH protons not observed.<br>$^{13}C$ NMR (100 MHz, Methanol-$d_4$): δ 164.03, 158.74, 150.51 (d, J = 245.71 Hz), 125.93 (d, J = 7.5 Hz), 125.13 (d, J = 3.5 Hz), 116.00, 115.47 (d, J = 18.0 Hz), 114.90 (d, J = 18.1 Hz).<br>Yield: 8% |

TABLE 1-continued

| Compound | Synthesis method, NMR characteristics and % yield |
|---|---|
| 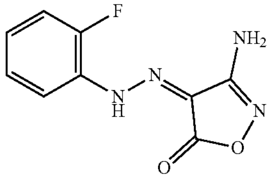<br>(H6-335 —SAR compound-45)<br>4-[(2-fluorophenyl)hydrazinylidene]-3-aminoisoxazol-5(4H)-one | General procedure A2 followed by B3<br>$^{1}$H NMR (400 MHz, Methanol-$d_4$): δ 7.71 (td, J = 8.1, 1.7 Hz, 1H), 7.21-7.08 (m, 2H), 7.07-6.97 (m, 1H). NH protons not observed.<br>$^{13}$C NMR (100 MHz, Methanol-$d_4$): δ 165.64, 151.38, 151.21 (d, J = 242.5 Hz), 131.23 (d, J = 9.5 Hz), 124.70 (d, J = 3.5 Hz), 122.94 (d, J = 7.2 Hz), 119.59, 115.27 (d, J = 2.0 Hz), 114.89 (d, J = 18.0 Hz).<br>Yield: 77% |
| 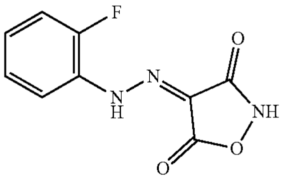<br>(H6-335 —SAR compound-46)<br>(4-[(2-fluorophenyl)hydrazinylidene]-isoxazolidine-3,5-dione) | General procedure A3 followed by B3<br>$^{1}$H NMR (400 MHz, DMSO-$d_6$): δ 11.09 (s, 1H), 7.49-7.37 (m, 3H), 7.14 (m, 1H).<br>$^{13}$C NMR (100 MHz, DMSO-$d_6$): δ 154.51 (d, J = 245.7 Hz), 131.76 (d, J = 10.1 Hz), 125.3 (d, J = 2.1 Hz), 123.45 (d, J = 8.2 Hz), 121.71, 117.98 (d, J = 7.8 Hz), 116.43 (d, J = 18.1 Hz).<br>Yield: Quant. |
| 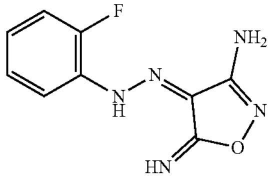<br>(H6-335 —SAR compound-47)<br>(4-[(2-fluorophenyl)hydrazin-ylidene]-5-imino-4,5-dihydroisoxazol-3-amine) | General procedure A1 followed by B3<br>$^{1}$H NMR (400 MHz, Acetone-$d_6$): δ 13.15 (s, 1H), 7.83 (td, J = 8.2, 1.7 Hz, 1H), 7.39-7.24 (m, 2H), 7.19-7.08 (m, 1H), 5.97 (s, 2H).<br>$^{13}$C NMR (100 MHz, Acetone-$d_6$): δ 159.34, 150.95 (d, J = 242.5 Hz), 150.08, 130.39 (d, J = 9.2 Hz), 126.48, 125.89 (d, J = 3.5 Hz), 124.92 (d, J = 7.2 Hz), 116.31 (d, J = 17.6 Hz), 115.70.<br>Yield: 12% |
| 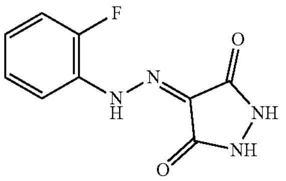<br>(H6-335 —SAR compound-48)<br>(4-[(2-fluorophenyl)hydrazin-ylidene]pyrazole-3,5-dione) | General procedure A3 followed by B1<br>$^{1}$H NMR (400 MHz, Methanol-$d_4$): δ 7.88 (td, J = 7.9, 1.6 Hz, 1H), 7.34-7.20 (m, 3H). NH protons not observed.<br>$^{13}$C NMR (100 MHz, Methanol-$d_4$): δ 161.59, 151.68 (d, J = 244.7 Hz), 129.50 (d, J = 8.9 Hz), 125.92 (d, J = 7.4 Hz), 125.28 (d, J = 3.6 Hz), 122.62, 115.86, 115.52 (d, J = 18.0 Hz).<br>Yield: 42% |
| 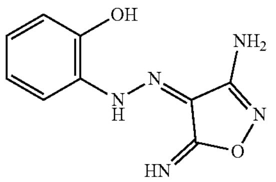<br>(H6-335 —SAR compound-49)<br>(4-[(2-hydroxyphenyl)hydrazin-ylidene]-5-imino-4,5-dihydroisoxazol-3-amine) | General procedure A1 followed by B3<br>$^{1}$H NMR (400 MHz, DMSO-$d_6$): δ 10.08 (s, 1H), 7.44-7.33 (m, 2H), 7.21 (m, 2H)<br>$^{13}$C NMR (100 MHz, DMSO-$d_6$): δ 146.73, 128.42, 123.46, 121.15, 119.63, 116.23, 115.52.<br>Yield: Quant. |
| 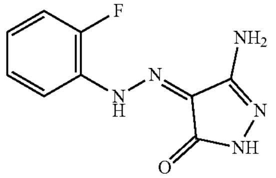<br>(H6-335 —SAR compound-50)<br>(4-[(2-fluorophenyl)hydrazinylidene]-3-aminopyrazole -5(4H)-one) | General procedure A2 followed by B1<br>$^{1}$H NMR (400 MHz, DMSO-$d_6$): δ 7.78 (td, J = 7.9, 7.4, 1.2 Hz, 1H), 7.39-7.26 (m, 2H), 7.23 (ddd, J = 8.4, 5.3, 3.4 Hz, 1H), 6.28 (s, 1H).<br>$^{13}$C NMR (100 MHz, DMSO-$d_6$): 0 158.54, 149.05 (d, J = 245.43 Hz), 148.97, 129.54 (d, J = 9.7 Hz), 124.96 (d, J = 3.7 Hz), 124.83 (d, J = 7.2 Hz) 117.52.<br>Yield: 38% |

TABLE 1-continued

| Compound | Synthesis method, NMR characteristics and % yield |
|---|---|
| 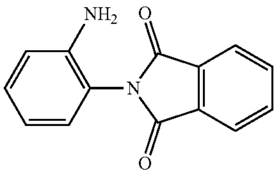 (Intermediate) | o-Phenylenediamine (1 g, 9.25 mmol, 1 eq) was dissolved in 0.1 M phosphate buffer (2.2 ml/mmol) and N-hydroxyphthalimide was added (1 eq). The reaction was stirred overnight at rt. The product was isolated by filtration and washed with water. $^{1}$H NMR (400 MHz, DMSO-$d_6$): δ 7.98-7.82 (m, 4H), 7.18-7.09 (m, 1H), 7.02 (dd, J = 7.8, 1.5 Hz, 1H), 6.77 (dd, J = 8.2, 1.3 Hz, 1H), 6.58 (td, J = 7.5, 1.4 Hz, 1H), 5.37 (s, 2H). $^{13}$C NMR (100 MHz, DMSO-$d_6$): δ 168.02, 146.96, 134.57, 132.96, 130.47, 130.16, 123.53, 116.42, 115.81, 115.77. Yield: 85% |
| 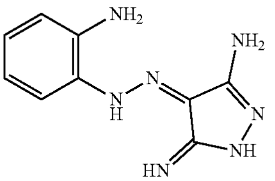 (H6-335 —SAR compound-51) (4-[(2-aminophenyl)hydrazin-ylidene]pyrazole-3,5-diamine) | General procedure A1 followed by B1 $^{1}$H NMR (400 MHz, DMSO-$d_6$): δ 10.58 (s, 1H), 7.48 (dd, J = 8.0, 1.5 Hz, 1H), 6.96-6.87 (m, 1H), 6.73 (dd, J = 8.1, 1.3 Hz, 1H), 6.57-6.48 (m, 1H), 5.72 (s, 2H). $^{13}$C NMR (100 MHz, DMSO-$d_6$): δ 143.51, 138.54, 127.99, 120.14, 116.44, 116.03, 114.13. Yield: Quant. |
| 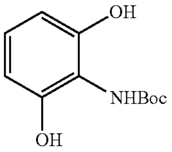 (Intermediate) | 2-Aminoresorcinol (589.2 mg, 4.71 mmol, 1 eq) was dissolved in water (5 mL) and added boc-anhydride (1.13 g, 1.1 eq). Upon completion of the reaction, the product was isolated by filtration as a black solid. $^{1}$H NMR (400 MHz, DMSO-$d_6$): δ 9.07 (s, 2H), 7.65 (s, 1H), 6.81 (t, J = 8.1 Hz, 1H), 6.30 (d, J = 8.1 Hz, 2H), 1.42 (s, 9H). $^{13}$C NMR (100 MHz, DMSO-$d_6$): δ 154.98, 154.39, 146.68, 126.92, 113.67, 107.24, 86.08, 78.75, 28.65. Yield: 98% |
| 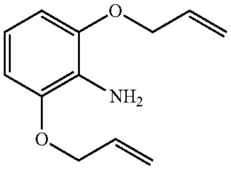 (Intermediate) | tert-Butyl (2,6-dihydroxyphenyl)carbamate (1 eq) and $K_2CO_3$ (3 eq) was dissolved in DMF (1 mL/mmol) and allylbromide (2.3 eq) was added. The reaction was left with stirring overnight at rt. The mixture was filtered and the filtrate was washed with water. The aqueous phase was extracted with $Et_2O$ twice. The combined organic phase was washed with brine and dried over $Na_2SO_4$. After removal of the solvent under vacuum, two immiscible oils were obtained, which could be separated to give a black oil. DCM:TFA (4:1, 25 mL) were added and the mixture stirred for 1 h. The TFA and DCM were removed under vacuum, followed by co-evaporating with heptane to give the product 2,6-bis(allyloxy)aniline. $^{1}$H NMR (400 MHz, DMSO-$d_6$): δ 10.28 (s, 6H), 7.18 (t, J = 8.4 Hz, 1H), 6.74 (d, J = 8.5 Hz, 2H), 6.02 (ddt, J = 17.4, 10.5, 5.2 Hz, 2H), 5.43 (dq, J = 17.4, 1.7 Hz, 2H), 5.25 (dq, J = 10.5, 1.5 Hz, 2H), 4.65 (dt, J = 5.2, 1.7 Hz, 4H). $^{13}$C NMR (100 MHz, DMSO-$d_6$): δ 151.82, 133.41, 128.07, 118.22, 111.13, 106.32, 69.78. Yield: 71% |
| 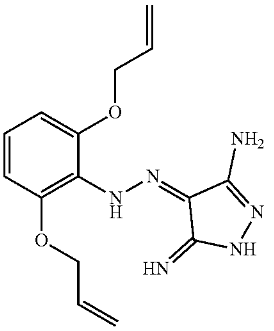 (Intermediate) | General procedure A1 followed by B1 from 2,6-Bis(allyloxy)aniline Used without further purification in the next step. Yield: Crude 96% |

TABLE 1-continued

| Compound | Synthesis method, NMR characteristics and % yield |
|---|---|
| 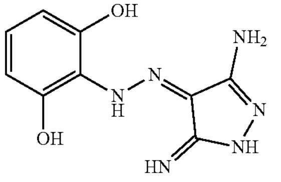<br>(H6-335 —SAR compound-52)<br>4-[(2,6-dihydroxyphenyl)-hydrazinylidene]pyrazole-3,5-diamine) | 4-[(2,6-bis (allyloxy)phenyl)-hydrazinylidene]pyrazole-3,5-diamine (1 eq) was dissolved in dry MeOH (10.8 mL/mmol) and Pd (PPh3)4 (0.02 eq) added, followed by $K_2CO_3$ (6 eq). The reaction was allowed to stir overnight under nitrogen. The mixture was filtered, conc. in vacuo, and purified by preparative HPLC.<br>$^1$H NMR (400 MHz, Deuterium Oxide): δ 10.4 (s, 2H), 7.14 (t, J = 7.9 Hz, 1H), 6.77 (m, 2H).<br>$^{13}$C NMR (100 MHz, Deuterium Oxide): δ 146.34, 121.54, 121.11, 119.26, 109.3.<br>Yield: Quant. |
| 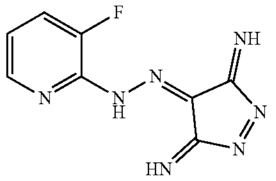<br>(H6-335 —SAR compound-53)<br>(4-[2-(3-fluoropyridin-2-yl)hydrazin-ylidene]pyrazole-3,5-diamine) | General procedure A1 followed by B1<br>$^1$H NMR (400 MHz, DMSO-$d_6$): δ 7.41-7.32 (m, 1H), 7.22 (dd, J = 6.6, 1.8 Hz, 1H), 6.14 (td, J = 6.9, 4.1 Hz, 1H). NH protons not observed.<br>Yield: Quant. |
| 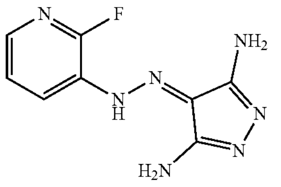<br>(H6-335 —SAR compound-54)<br>(4-[2-(2-fluoropyridin-3-yl)hydrazin-ylidene]pyrazole-3,5-diamine) | General procedure A1 followed by B1<br>$^1$H NMR (400 MHz, DMSO-$d_6$): δ 7.62 (dd, J = 7.2, 2.0 Hz, 1H), 7.28 (dd, J = 6.4, 2.0 Hz, 1H), 6.60 (s, 2H), 6.23 (dd, J = 7.2, 6.3 Hz, 1H), 5.78 (s, 2H).<br>Yield: 91% |
| 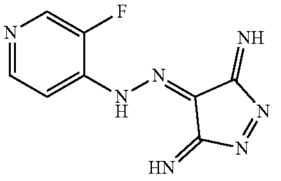<br>(H6-335 —SAR compound-55)<br>(4-[2-(3-fluoropyridin-4-yl)hydrazin-ylidene]pyrazole-3,5-diamine) | General procedure A1 followed by B1<br>$^1$H NMR (400 MHz, DMSO-$d_6$): δ 8.06 (d, J = 3.7 Hz, 1H), 7.86 (dd, J = 5.3, 0.8 Hz, 1H), 7.41 (s, 9H), 6.68 (dd, J = 8.1, 5.3 Hz, 1H), 6.18 (s, 2H).<br>$^{13}$C NMR (100 MHz, DMSO-$d_6$): δ 173.46, 148.87 (d, J = 244.3 Hz), 146.17 (d, J = 4.3 Hz), 143.10 (d, J = 10.7 Hz), 136.12 (d, J = 19.2 Hz), 110.96 (d, J = 3.0 Hz).<br>Yield: Quant. |
| 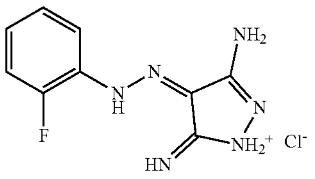<br>(HCl salt of H6-335—P1) | General procedure A1 followed by B1 followed by C1<br>$^1$H NMR (400 MHz, DMSO-$d_6$): δ 7.87-7.83 (m, 1H), 7.42-7.36 (m, 2H), 7.28-7.24 (m, 1H). NH protons not observed.<br>$^{13}$C NMR (100 MHz, DMSO-$d_6$): δ 158.09 (d, J = 251.8 Hz), 154.48, 140.65 (d, J = 6.7 Hz), 130.66 (d, J = 8.2 Hz), 125.13, 117.78, 117.15 (d, J = 19.4 Hz).<br>Yield: 100% |
| 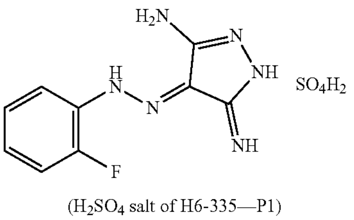<br>($H_2SO_4$ salt of H6-335—P1) | General procedure A1 followed by B1 followed by C1<br>$^1$H NMR (400 MHz, DMSO-$d_6$): δ 7.80 (dt, J = 8.0, 2.0 Hz, 1H), 7.30-7.15 (m, 3H). NH protons not observed.<br>$^{13}$C NMR (100 MHz, DMSO-$d_6$): δ 158.74 (d, J = 247.1 Hz), 153.33, 141.75 (d, J = 5.4 Hz), 127.91 (d, J = 7.2 Hz), 124.86, 117.33, 116.71 (d, J = 20.5 Hz).<br>Yield: 100% |

TABLE 1-continued

| Compound | Synthesis method, NMR characteristics and % yield |
|---|---|
| 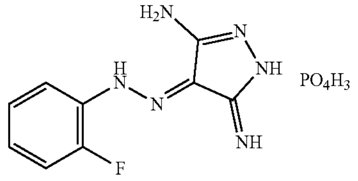<br>($H_3PO_4$ salt of H6-335—P1) | General procedure A1 followed by B1 followed by C1<br>$^1$H NMR (400 MHz, DMSO-$d_6$): δ 7.81 (dt, J = 8.0, 2.0 Hz, 1H), 7.29-7.17 (m, 3H). NH protons not observed.<br>$^{13}$C NMR (100 MHz, DMSO-$d_6$): δ 158.74 (d, J = 248.8 Hz), 152.43, 141.72 (d, J = 6.6 Hz), 127.90 (d, J = 8.6 Hz), 124.86, 117.33, 116.70 (d, J = 19.4 Hz).<br>$^{31}$P NMR (162 MHz, DMSO-$d_6$): δ −0.79.<br>Yield: 100% |
| 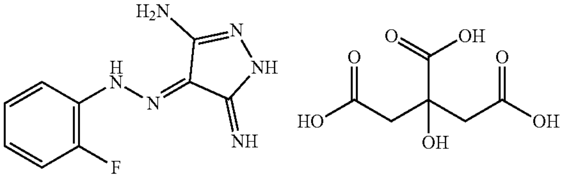<br>(Citric acid salt of H6-335—P1) | General procedure A1 followed by B1 followed by C1<br>$^1$H NMR (400 MHz, DMSO-$d_6$): δ 7.80 (dt, J = 8.1, 1.7 Hz, 1H), 7.32-7.16 (m, 3H), 2.74 (s, 2H), 2.68 (s, 2H). NH protons not observed.<br>$^{13}$C NMR (100 MHz, DMSO-$d_6$): δ 175.02, 171.14, 157.54 (d, J = 249.4 Hz), 155.11, 141.62 (d, J = 6.5 Hz), 128.14 (d, J = 7.7 Hz), 124.88, 117.35, 116.74 (d, J = 19.6 Hz) 72.89, 43.17.<br>Yield: 10% |
| 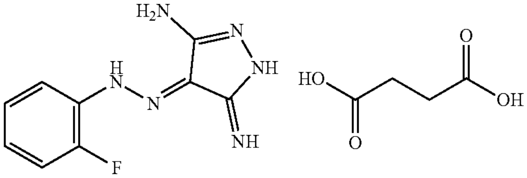<br>(Succinic acid salt of H6-335—P1) | General procedure A1 followed by B1 followed by C1<br>$^1$H NMR (400 MHz, DMSO-$d_6$): δ 7.80 (dt, J = 8.1, 2.1 Hz, 1H), 7.30-7.14 (m, 3H), 2.42 (s, 4H). NH protons not observed.<br>$^{13}$C NMR (100 MHz, DMSO-$d_6$): δ 174.04, 156.34 (d, J = 247.8 Hz), 154.87, 142.12 (d, J = 6.4 Hz), 129.24 (d, J = 8.4 Hz), 125.14, 116.87, 116.52 (d, J = 19.4 Hz), 29.<br>Yield: 11% |
| 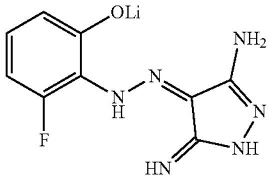<br>(Lithium salt of H6-335 —SAR compound-25) | General procedure A1 followed by B1 followed by C2<br>$^1$H NMR (400 MHz, DMSO-$d_6$): δ 11.17 (s, 1H), 7.25-7.16 (m, 1H), 6.91-6.77 (m, 1H), 6.71-6.65 (m, 1H), 6.57 (s, 2H).<br>$^{13}$C NMR (100 MHz, DMSO-$d_6$): δ 157.44 (d, J = 249.9 Hz), 151.26 (d, J = 2.3 Hz), 128.41 (d, J = 10.6 Hz), 127.21 (d, J = 8.1 Hz), 114.25, 113.53 (d, J = 3.1 Hz), 106.76 (d, J = 20.7 Hz).<br>Yield: quant. |
| 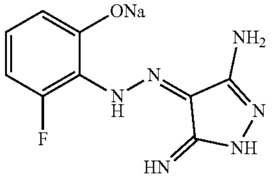<br>(Sodium salt of H6-335 —SAR compound-25) | General procedure A1 followed by B1 followed by C2<br>$^1$H NMR (400 MHz, DMSO-$d_6$): δ 10.97 (s, 1H), 7.21-7.17 (m, 1H), 6.93-6.78 (m, 1H), 6.72-6.68 (m, 1H), 6.54 (s, 2H).<br>$^{13}$C NMR (100 MHz, DMSO-$d_6$): δ 157.34 (d, J = 249.3 Hz), 151.56 (d, J = 2.1 Hz), 128.61 (d, J = 10.4 Hz), 127.17 (d, J = 8.4 Hz), 114.29, 113.51 (d, J = 3.2 Hz), 106.79 (d, J = 20.8 Hz).<br>Yield: quant. |

Example 2 Determining the Structure-Activity-Relationship of Compounds

The ability of all compounds H6-335, H6-335-P1, and H6-335-SAR compound-1 to H6-335-SAR compound-55 to reduce the total cellular c-di-CMP levels has been determined. In Table 2 below, the activities of all compounds showing reduction of total cellular c-di-GMP level are listed (compounds are dissolved in either $H_2O$ or DMSO).

The reduction of total cellular c-di-GMP level was determined as follows. To evaluate the impact of the various compounds on the c-di-GMP level of *P. aeruginosa* ΔwspFΔpelΔpsl/pCdrA-gfp, 20 hour old cultures of the strain were diluted 100 fold in microtiter plate wells (Nunc) containing 100 μl aliquots of ABTrace medium supplemented with 0.2% glucose, 0.5% casamino acids, 60 μg/ml gentamicin, 1 μM $FeCl_3$, 1% DMSO, and concentrations of compounds as indicated.

Subsequently the microtiter plates were incubated at 37° C. and 440 RPM in a TECAN reader (Infinite F200 PRO), and corresponding values of cell density ($OD_{600}$) and GFP fluorescence were measured every 20 minutes for 24 hours. The reduction values indicated in the tables are calculated as fluorescence values divided by optical density at a time point where this value reached a plateau.

TABLE 2

| Structural formula of active compounds of the invention | Synthesis procedure (according to example 1) Reduction of total cellular c-di-GMP level (compounds are stored in DMSO and are transferred to aqueous solutions giving rise to a compound concentration of 100 μM and a DMSO concentration of 1%) |
| --- | --- |
| 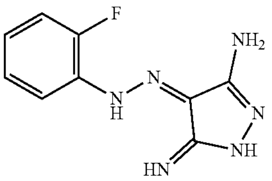 [SMILES: N=C1NN=C(N)/C1=N/Nc1ccccc1F] (H6-335-P1) (4-[(2-fluorophenyl) hydrazinylidene]pyrazole-3,5-diamine) | General procedure B1 80% reduction of cellular c-di-GMP level. |
| 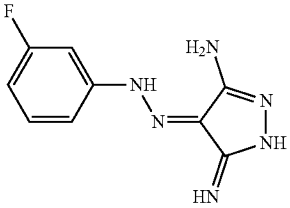 [SMILES: N=C1NN=C(N)/C1=N\Nc1cccc(F)c1] (H6-335) The Library compound (4-[(3-fluorophenyl) hydrazinylidene]pyrazole-3,5-diamine) | General procedure A1 followed by B1 73% reduction of cellular c-di-GMP level. |
| 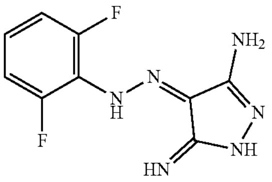 [SMILES: N=C1NN=C(N)/C1=N/Nc1c(F)cccc1F] (H6-335 -SAR compound 26) (4-[(2,6-difluorophenyl) hydrazinylidene]pyrazole-3,5-diamine) | General procedure A1 followed by B1 77% reduction of cellular c-di-GMP level. |
| 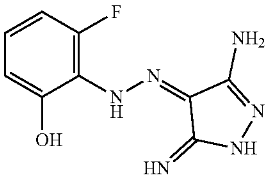 [SMILES: N=C1NN=C(N)/C1=N/Nc1c(O)cccc1F] (H6-335 -SAR compound-25) (4-[(2-fluoro-6-hydroxyphenyl) hydrazinylidene]pyrazole-3,5-diamine) | General procedure A1 followed by B1 75% reduction of cellular c-di-GMP level. |
| 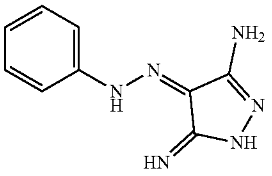 [SMILES: N=C1NN=C(N)/C1=N/Nc1ccccc1] (H6-335 -SAR compound-1) (4-[phenyl hydrazinylidene]pyrazole-3,5-diamine) | General procedure A1 followed by B1 71% reduction of cellular c-di-GMP level. |

TABLE 2-continued

| Structural formula of active compounds of the invention | Synthesis procedure (according to example 1) Reduction of total cellular c-di-GMP level (compounds are stored in DMSO and are transferred to aqueous solutions giving rise to a compound concentration of 100 μM and a DMSO concentration of 1%) |
|---|---|
| 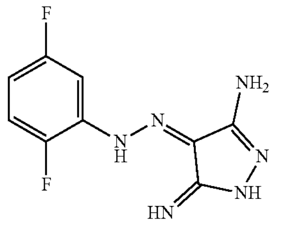 [SMILES: N=C1NN=C(N)/C1=N/Nc1cc(F)ccc1F] (H6-335 -SAR compound-29) (4-[(2,5-difluorophenyl) hydrazinylidene]pyrazole-3,5-diamine) | General procedure A1 followed by B1 65% reduction of cellular c-di-GMP level. |
| 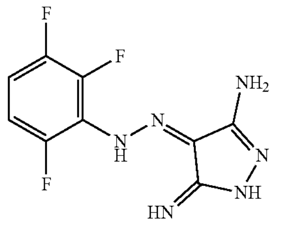 [SMILES: N=C1NN=C(N)/C1=N/Nc1c(F)ccc(F)c1F] (H6-335 -SAR compound-40) (4-[(2,3,6-trifluorophenyl) hydrazinylidene]pyrazole-3,5-diamine) | General procedure A1 followed by B1 61% reduction of cellular c-di-GMP level. |
| 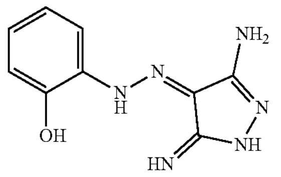 [SMILES: N=C1NN=C(N)/C1=N/Nc1ccccc1O] (H6-335 -SAR compound-23) (4-[(2-hydroxyphenyl) hydrazinylidene]pyrazole-3,5-diamine) | General procedure A1 followed by B1 55% reduction of cellular c-di-GMP level. |
| 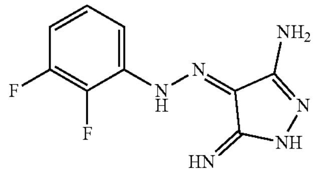 [SMILES: N=C1NN=C(N)/C1=N/Nc1cccc(F)c1F] (H6-335 -SAR compound-2) (4-[(2,3-difluorophenyl) hydrazinylidene]pyrazole-3,5-diamine) | General procedure A1 followed by B1 48% reduction of cellular c-di-GMP level. |
| 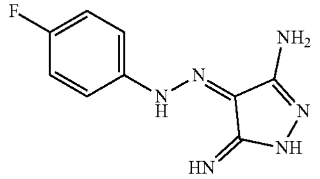 [SMILES: N=C1NN=C(N)/C1=N/Nc1ccc(F)cc1] (H6-335 -SAR compound-3) (4-[(4-fluorophenyl) hydrazinylidene]pyrazole-3,5-diamine) | General procedure A1 followed by B1 44% reduction of cellular c-di-GMP level. |

TABLE 2-continued

| Structural formula of active compounds of the invention | Synthesis procedure (according to example 1) Reduction of total cellular c-di-GMP level (compounds are stored in DMSO and are transferred to aqueous solutions giving rise to a compound concentration of 100 µM and a DMSO concentration of 1%) |
|---|---|
| 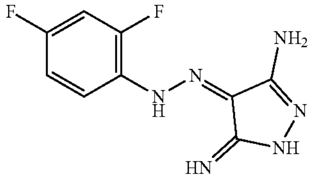 [SMILES: N=C1NN=C(N)/C1=N/Nc1ccc(F)cc1F] (H6-335 -SAR compound-4) (4-[(2,4-difluorophenyl) hydrazinylidene]pyrazole-3,5-diamine) | General procedure A1 followed by B1 41% reduction of cellular c-di-GMP level. |
| 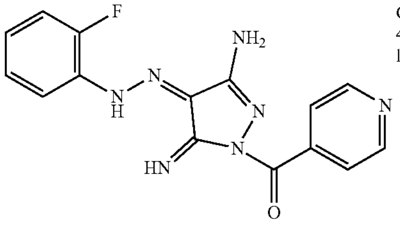 (H6-335 -SAR compound-21) (4-[(2-fluorophenyl)hydrazinylidene]-1-(pyridin-4-yl-methanone)pyrazole-3,5-diamine) | General procedure A1 followed by B1 40% reduction of cellular c-di-GMP level |
| 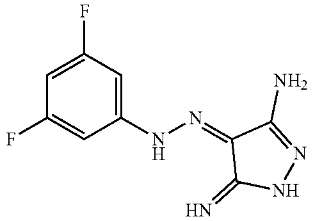 [SMILES: N=C1NN=C(N)/C1=N/Nc1cc(F)cc(F)c1] (H6-335 -SAR compound-28) (4-[(3,5-difluorophenyl) hydrazinylidene]pyrazole-3,5-diamine) | General procedure A1 followed by B1 35% reduction of cellular c-di-GMP level. |
| 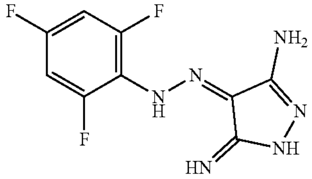 [SMILES: N=C1NN=C(N)/C1=N/Nc1c(F)cc(F)cc1F] (H6-335 -SAR compound-39) (4-[(2,4,6-trifluorophenyl) hydrazinylidene]pyrazole-3,5-diamine) | General procedure A1 followed by B1 30% reduction of cellular c-di-GMP level. |
| 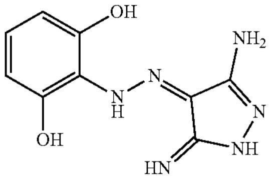 [SMILES: N=C1NN=C(N)/C1=N/Nc1c(O)cccc1O] (H6-335 -SAR compound-52) (4-[(2,6-dihydroxyphenyl) hydrazinylidene]pyrazole-3,5-diamine) | See Table 1 5% reduction of cellular c-di-GMP level. |

Example 3 (H6-335 Validation)

As quality control and final structural validation, H6-335 was synthesized from commercially available 3-fluoroaniline which was converted into the corresponding N-arylhydrazone and subsequent cyclization with hydrazine gave the corresponding hydrazonodiaminopyrazole H6-335 in two steps (FIG. 2) in an overall yield of 75%.

Next, the inventors performed direct measurements of the intracellular pool of c-di-GMP by means of tandem-MS analysis and validated the biological measurements of c-di-GMP contents (FIG. 1).

Specifically, a 20 h old culture of *P. aeruginosa* ΔwspF, Δpsl,Δpel (Rybtke et al 2012) was diluted 100 fold into 25 mL aliquots of ABtrace media supplemented with 0.5% Cas amino acids, 0.2% glucose, 60 μg/mL of gentamicin, 1 μM $FeCl_3$, 0.05% DMSO and either 100 μM H6-335-P1, 100 μM H6-335 or no compound as reference control. Acting as a positive control for low total cellular c-di-GMP content, a 20 hour old culture of strain *P. aeruginosa* ΔwspF,Δpsl,Δpel carrying plasmid pYhj::Gm (encoding a constitutively expressed YhjH phosphodiesterase) was also diluted 100 fold into 25 mL of ABtrace medium supplemented with 0.5% Cas amino acids, 0.2% glucose, 60 μg/mL of gentamicin, 1 μM $FeCl_3$ and 0.05% DMSO. The 4 cultures were placed on a rotary shaker and following 8 hours of growth at 37° C. and 200 RPM culture samples for c-di-GMP extraction and protein quantification was collected from each of the 4 different cultures. C-di-GMP extracts were prepared and subsequently quantified by HPLC coupled tandem-MS analysis as previously described (Groizeleau et al., 2016), while protein quantification was carried out using the Pierce 660 nm Protein Assay (Thermo Scientific Cat. No 22660) according to the manufacturer's protocol. Finally, pmol contents of c-di-GMP in each sample were normalized to mg of protein contents and plotted as a function of either no treatment (untreated), treatments (100 μM H6-335 or 100 μM H6-335-P1) or high expression of YhjH phosphodiesterase activity (YhjH+).

In line with the output measured by the live screen, H6-335 reduced the total cellular c-di-GMP content by 84% (FIG. 1), and equally important, it neither affected the growth rate nor the yield of the growing cultures (not shown). Further in line with the output measured by the live screen, H6-335-P1 reduced the total cellular c-di-GMP content by 90% (FIG. 1), verifying that the c-di-GMP reducing potency of H6-335-P1 is superior to H6-335. Noteworthy, the total cellular c-di-GMP content obtained by constitutive overexpression of the phosphodiesterase YhjH was only slightly lower than the total cellular c-di-GMP content obtained by addition of 100 μM H6-335-P1.

Example 4 (Continuous Measurements of c-di-GMP Levels in Response to Varying H6-335-P1 Concentrations)

Figure 3A:
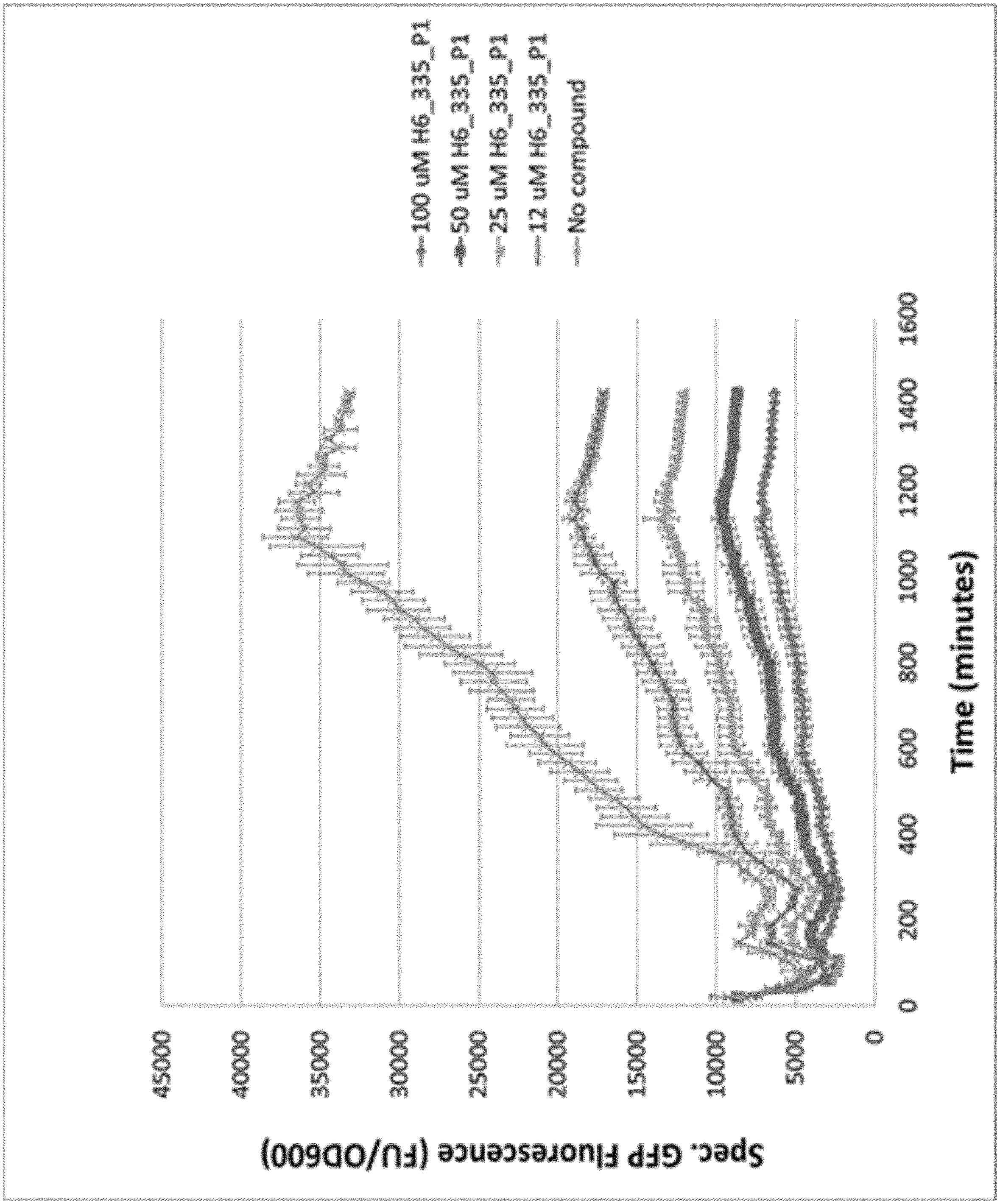
FIG. 3A shows the effects of varying H6-335-P1 concentrations on the GFP (Green Fluorescent Protein) output from the c-di-GMP monitor *P. aeruginosa* ΔwspFΔpelΔpsl monitor strain (Rybtke et al., 2012). GFP (FU, fluorescence unit) values were measured every 20 minutes for 24 hours with the following concentrations: 100 μM H6-335-P1, 50 μM H6-335-P1, 25 μM H6-335-P1, 12 μM H6-335-P1 or 0 μM H6-335-P1.
Figure 3B:
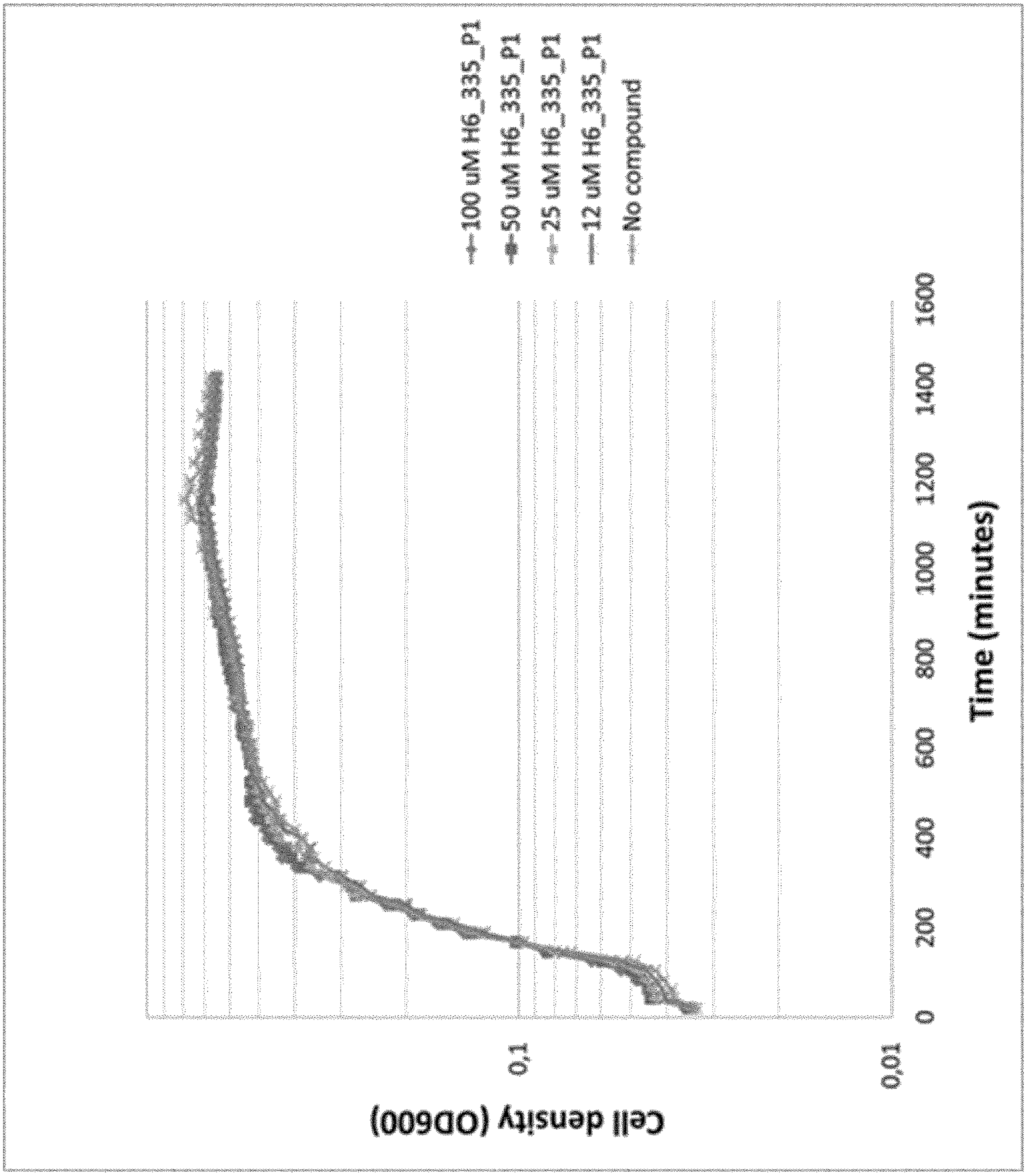
FIG. 3B shows the effects of varying H6-335-P1 concentrations on corresponding growth curves. OD600 values were measured every 20 minutes for 24 hours with the following concentrations: 100 μM H6-335-P1, 50 μM H6-335-P1, 25 μM H6-335-P1, 12 μM H6-335-P1 or 0 μM H6-335-P1.

In order to demonstrate the effects of varying H6-335-P1 concentrations on the GFP output and the growth kinetics of the *P. aeruginosa* ΔwspFΔpelΔpsl c-di-GMP monitor strain (Rybtke et al., 2012), cultures of the *P. aeruginosa* ΔwspFΔpelΔpsl c-di-GMP monitor strain were challenged with either 100 μM H6-335-P1, 50 μM H6-335-P1, 25 μM H6-335-P1, 12 μM H6-335-P1 or 0 μM H6-335-P1 (FIGS. 3A and 3B). Briefly, using a 96 well microtiter tray format, a 20 hour old culture of the *P. aeruginosa* c-di-GMP monitor strain (*P. aeruginosa* ΔwspF, Δpel, Δpsl carrying plasmid pCdrA-gfp) (Rybtke et al 2012) was diluted 100 fold into 100 μL aliquots of ABtrace media supplemented with 0.5% Cas amino acids, 0.2% glucose, 1 μM $FeCl_3$, 60 μg/mL of gentamicin, 1% DMSO and either 100 μM H6-335-P1, 50 μM H6-335-P1, 25 μM H6-335-P1, 12 μM H6-335-P1 or 0 μM H6-335-P1. The resulting microtiter trays were incubated at 37° C. at 440 RPM in a TECAN reader (Infinite F200 PRO), and corresponding values of GFP fluorescence (FU) and cell density (OD600) were measured every 20 minutes for 24 hours. Finally, specific GFP values (GFP/OD600) was calculated and plotted as a function of time and H6-335-P1 concentration (FIG. 3A), and cell density values (OD600) was plotted as a function of time and H6-335-P1 concentration (FIG. 3B). In FIGS. 3A and 3B, means and standard deviations (bars) represents 3 biological replicates (n=3).

As can be seen from FIGS. 3A and 3B increasing concentrations (from 0 to 100 μM) of H6-335-P1 stepwise reduces the c-di-GMP content of the bacteria, but does not inhibit growth. H6-335-P1 was at a concentration of 100 μM capable of reducing the fluorescence output of the c-di-GMP monitor cultures with 80% compared with the control cultures that contained medium supplemented with 1% DMSO.

Example 5 (Anti-Biofilm Properties of H6-335-P1)

Figure 4A:
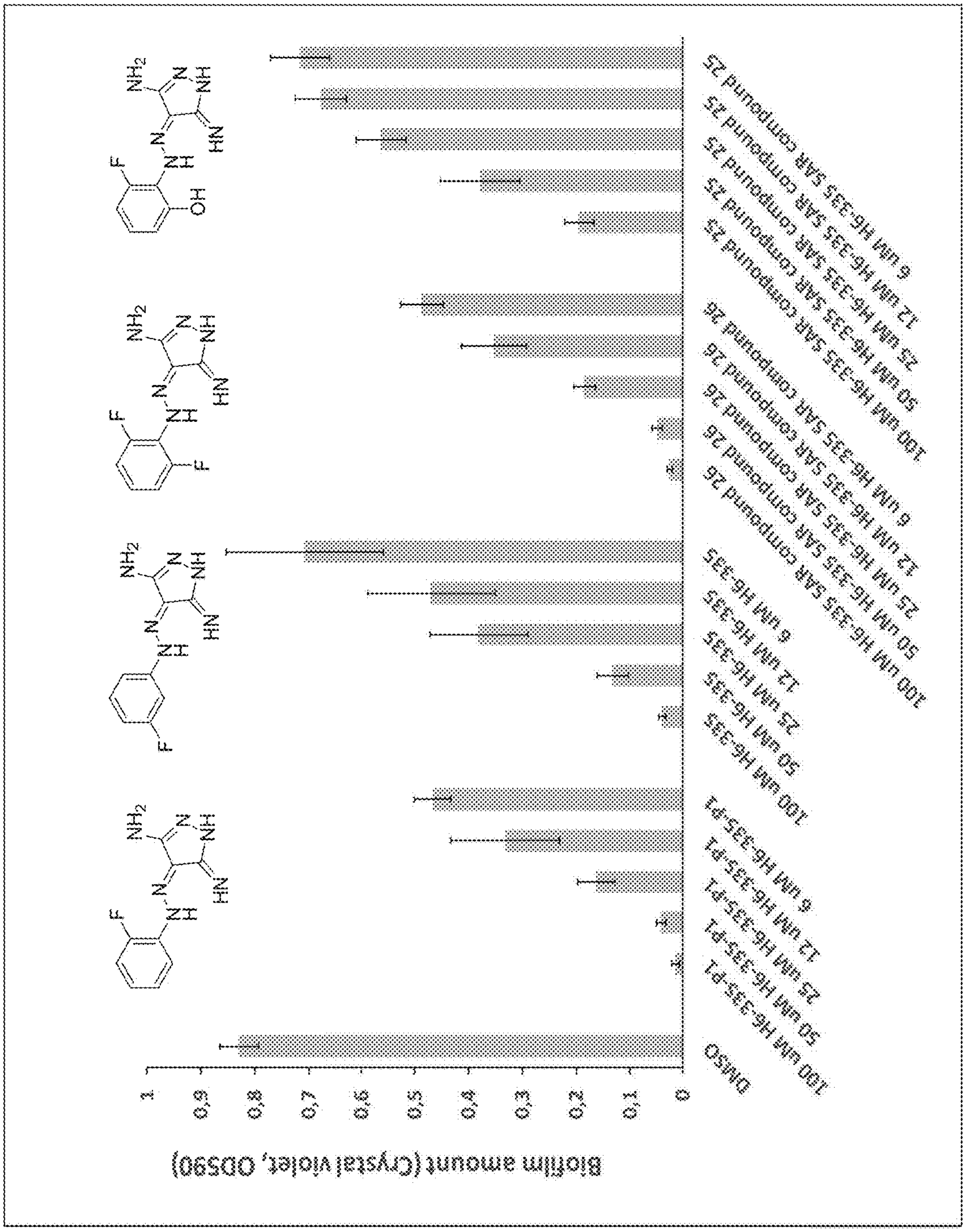
FIG. 4A shows inhibition of biofilm development as a function of H6-335-P1, H6-335, H6-335-SAR compound 26 and H6-335-SAR compound 25 at the concentrations 100 μM, 50 μM, 25 μM, 12 μM, 6 μM or 0 μM H6-335-P1 (dose-response).

For the purpose of demonstrating the anti-biofilm properties of the four most efficient c-di-GMP reducing compounds, microtiter tray experiments were carried out involving crystal violet staining of biofilm material, and the experiments showed that all 4 compounds gave rise to distinct concentration dependent biofilm inhibition (FIG. 4A).

Briefly, using a microtiter tray format, a 20 hour old culture of wt *P. aeruginosa* was diluted 1000 fold into 100 μL ABtrace media aliquots supplemented with 0.2% glucose, 0.5% Cas amino acids, 1 μM $FeCl_3$, 0.2% DMSO and varying concentrations (100 μM, 50 μM, 25 μM, 12 μM, 6 μM or 0 μM) of either H6-335-P1, H6-335, H6-335-SAR compound 26 or H6-335-SAR compound 25. The resulting microtiter trays were sealed with an air permeable lid, and biofilm cultures were grown on a rotary shaker at 37° C. and 160 RPM for 8 hours. After this, culture-supernatants were discarded and the remaining biomass was stained with crystal violet (Groizeleau et al., 2016). Finally, the amount of Crystal violet bound to the biofilm present in each well was plotted as a function of H6-335-P1, H6-335, H6-335-SAR compound 26 and H6-335-SAR compound 25 in the following concentrations: 100 μM, 50 μM, 25 μM, 12 μM, 6 μM or 0 μM (FIG. 4A). Means and standard deviations (bars) in FIG. 4A represents 4 biological replicates (n=4).

As seen in FIG. 4A, the experiment revealed that H6-335-P1, H6-335, H6-335-SAR compound 26 and H6-335-SAR compound 25 all gave rise to distinct concentration dependent biofilm inhibition. It also identified H6-335-P1 as the most potent biofilm inhibitory compound, as 100 μM H6-335-P1 reduced biofilm formation of wt *P. aeruginosa* with 98% compared to untreated wt *P. aeruginosa* (DMSO control).

Figure 4B:
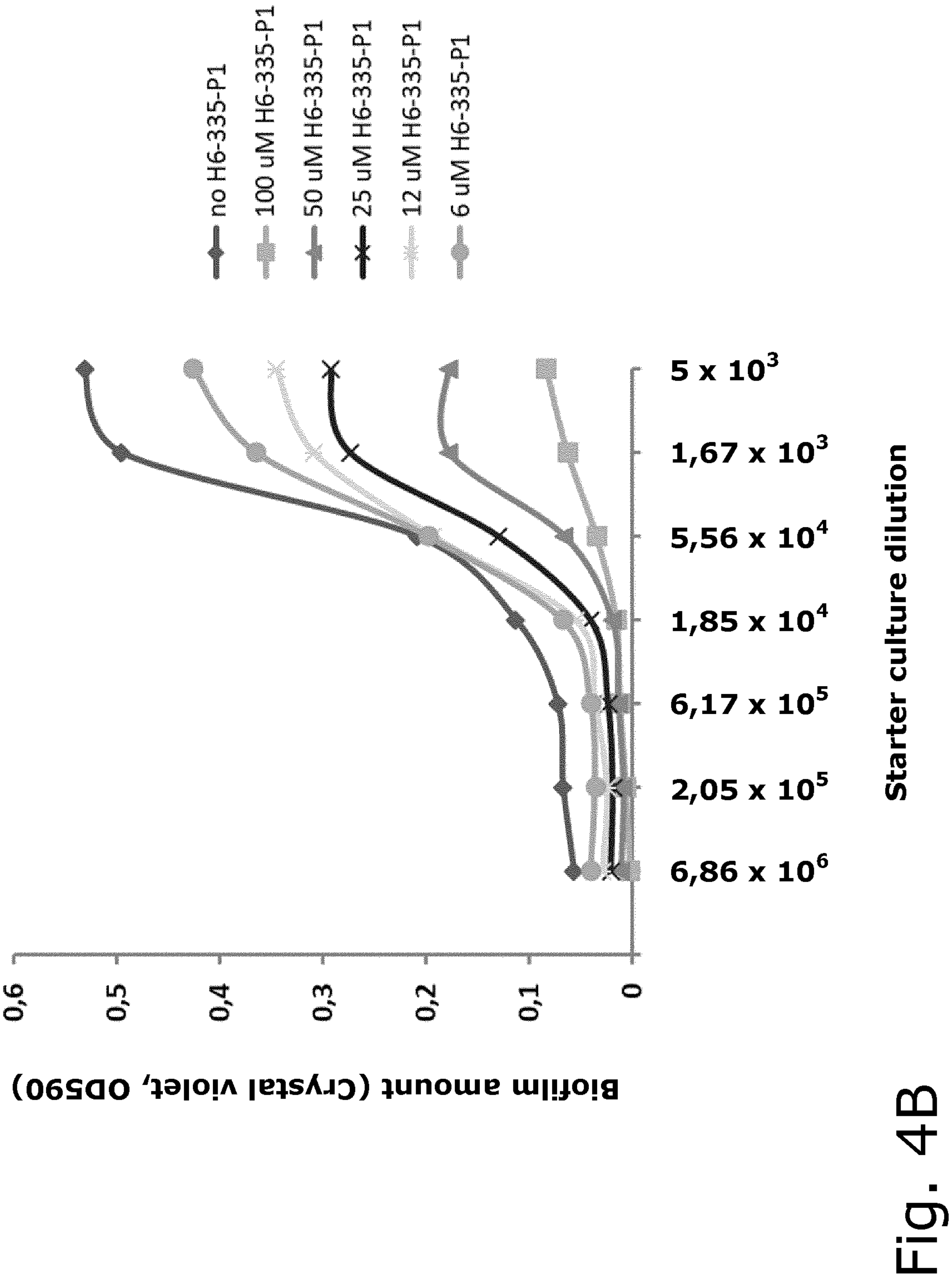
FIG. 4B shows anti-biofilm properties of H6-335-P1 on time dependent biofilm development as a function of H6-335-P1 concentrations (100 μM, 50 μM, 25 μM, 12 μM, 6 μM or 0 μM).

FIG. 4B shows anti-biofilm properties of H6-335-P1 as time dependent biofilm development in a 96 well microtiter tray as a function of H6-335-P1 concentration. To obtain time series reflecting biofilm formation as a function of growth phase and H6-335-P1 concentration, 7 well dilution rows of 3 fold serial dilutions of the inoculation culture (20 hour old culture diluted $5\times10^3$ fold) was established in wells containing 100 μl ABTrace media aliquots supplemented with 0.2% Glucose, 0.5% Casa amino acids, 0.2% DMSO, 1 μM $FeCl_3$ and either 100 μM, 50 μM, 25 μM, 12 μM, 6 μM or 0 μM H6-335-P1.

Biofilm cultures were grown at 37° C. on a rotary shaker (160 RPM) for 10 hours. After this, the supernatants were discarded and the remaining biomass was stained with crystal violet (Groizeleau et al. 2016). Finally, the amount of Crystal violet bound to the biofilm present in each well was plotted as a function of starter culture dilution at time T=0 hours, and H6-335-P1 concentration (100 μM, 50 μM, 25 μM, 12 μM, 6 μM or 0 μM H6-335-P1) (FIG. 4B).

Figure 4C:
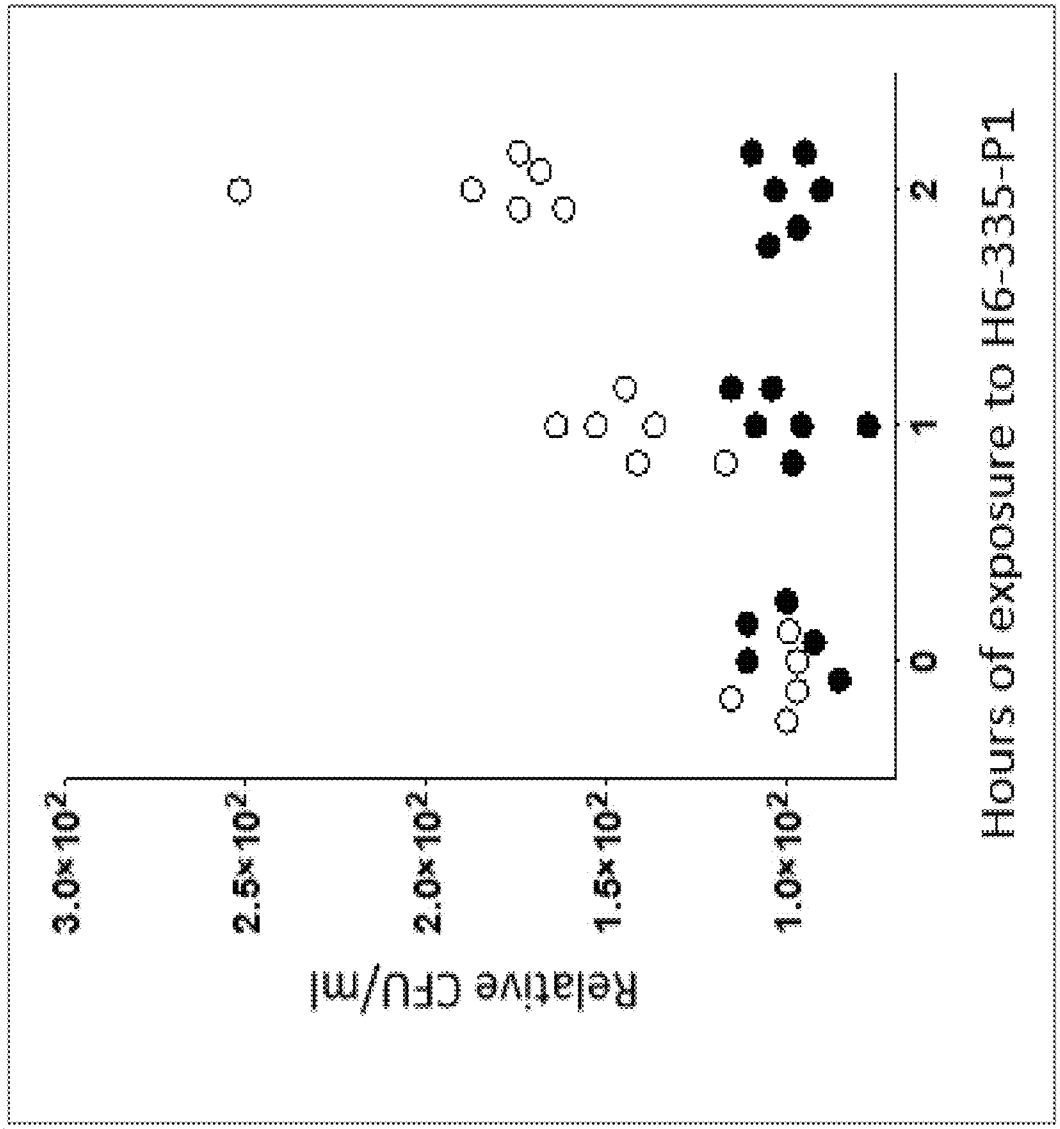
FIG. 4C shows time dependent liberation of bacteria during H6-335-P1 induced dispersal.

In a further experiment (FIG. 4C) the time dependent liberation of wt *P. aeruginosa* bacteria during H6-335-P1 induced dispersal performed in 48 well trays microtiter trays was determined. After 18 hours of growth in ABtrace media aliquots supplemented with 0.5% glucose, 0.5% Cas amino acids and 1 μM $FeCl_3$ on a rotary shaker, 25 μM H6-335-P1 or 1% DMSO control was added. At the time-points indicated, samples were withdrawn and plated for CFU determinations. Average CFU's per ml for the 1% DMSO controls at each time point are set to 100. The microtiter tray experiments with already formed biofilms exposed to 25 μM H6-335-P1 showed induced dispersal of live bacteria into the growth medium (FIG. 4C).

In a further experiment (FIG. 4D) the remaining (left behind) biofilm content was determined after two hours of H6 compound induced biofilm dispersal. Using a 96 well microtiter tray format, a 20 hour old culture of wt *P. aeruginosa* was diluted 1000 fold into 100 μL ABtrace media aliquots supplemented with 0.2% glucose, 0.5% Cas amino acids and 1 μM $FeCl_3$. The resulting microtiter trays were sealed with an air permeable lid and the biofilm cultures were incubated at 37° C. on a rotary shaker at 160 RPM.

Figure 4D:
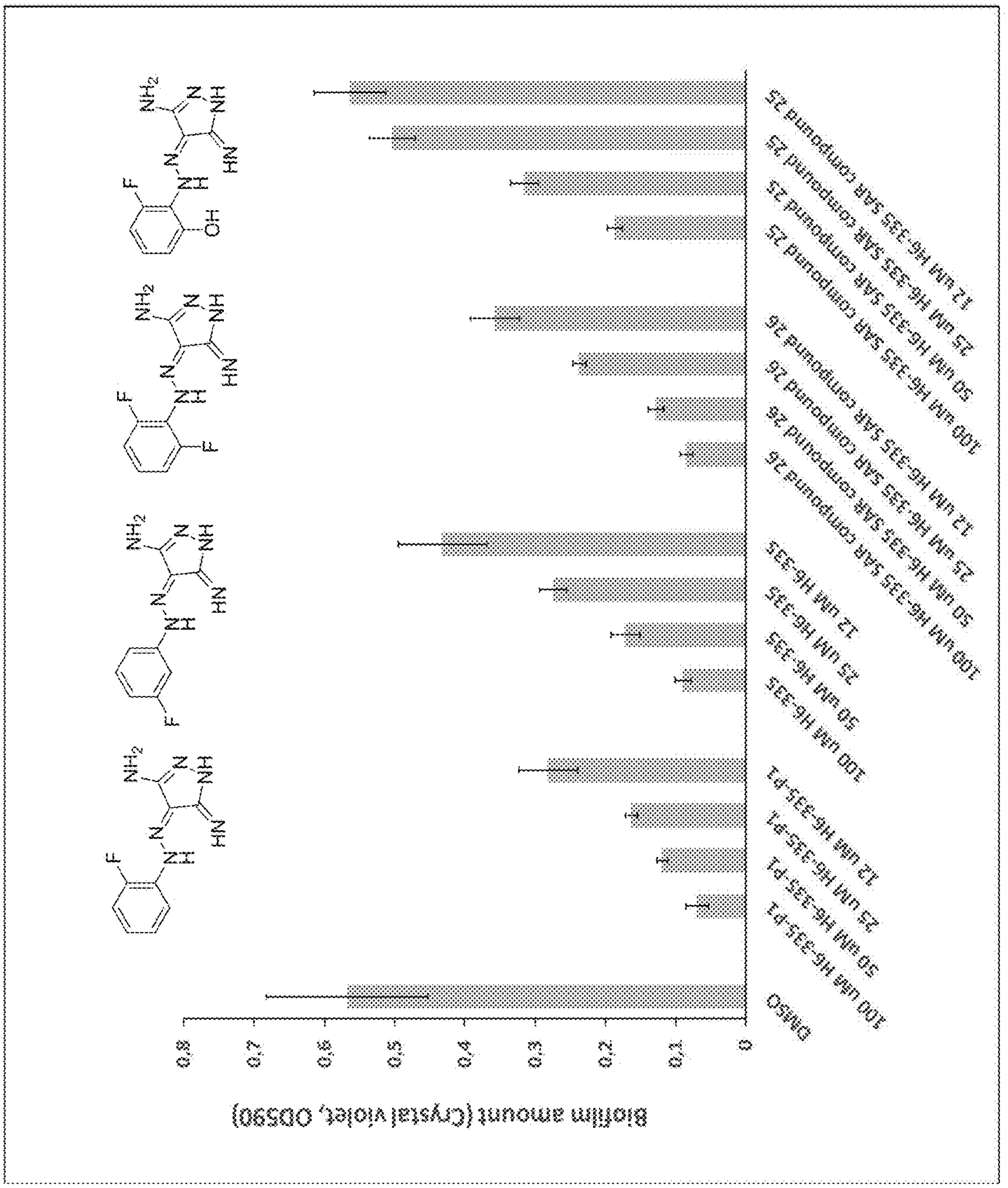
FIG. 4D shows the amount of biofilms (8 hours old) that remained after induction of dispersal (for subsequent two hours) with various concentrations of H6-335-P1, H6-335, H6-335-SAR compound 26 and H6-335-SAR compound 25

After 8 hours of growth, 1 μL aliquots containing 40% DMSO and various concentrations (10 mM, 5 mM, 2.5 mM, 1.25 mM or 0 mM) of either H6-335-P1, H6-335, H6-335-SAR compound 26 or H6-335-SAR compound 25 was added to the 8 hour old cultures and the plate was incubated at 160 RPM and 37° C. for 2 additional hours. After this, the culture supernatants were discarded and the remaining biomass was stained with crystal violet (Groizeleau et al. 2016). Finally, the amount of Crystal violet bound to the biofilm present in each well was plotted as a function of H6-335-P1, H6-335, H6-335-SAR compound 26 and H6-335-SAR compound 25 in the following concentrations: 100 μM, 50 μM, 25 μM, 12 μM or 0 μM (FIG. 4D). Means and standard deviations (bars) in FIG. 4D represents 5 biological replicates (n=5)

As judged from the Crystal violet stained biofilm material left behind after the two hours of dispersal (FIG. 4D), H6-335-P1 appears to be the most potent biofilm dispersing compound, while H6-335-SAR compound 26 appears to be the second most potent biofilm dispersing compound. Then follows H6-335, while H6-335-SAR compound 25 is observed to exhibit the lowest biofilm dispersing activity of the four tested compounds. Within a 2 hours period, 100 μM of H6-335-P1 is seen to disperse 88% of an 8 hour old biofilm of wt *P. aeruginosa.*

In order to demonstrate the effect of H6-335-P1 on the biofilm growth and inhibition, a flow-chamber system was operated as described by Crusz et al. (Crusz et al., 2012).

Biofilms were grown at 37° C. in continuous-culture, once-through, three-channel, flow-chambers (individual channel dimensions of 1×4×40 mm) perfused with sterile AB trace minimal medium (Pamp and Tolker-Nielsen, 2007), supplemented with 0.3 mM glucose and 0.025% (v/v) DMSO. *P. aeruginosa* (PA01) tagged with GFP at a neutral chromosomal locus was used for the experiments. After a static attachment phase of 1 h, the flow of medium was turned on and the biofilms were allowed to establish for 48 h in the absence (untreated) or presence (treated) of medium supplemented with 25 μM of H6-335-P1. Confocal laser scanning microscopy was used to image the biofilms after 24 h and 48 h (FIG. 5A).

Figure 5A:
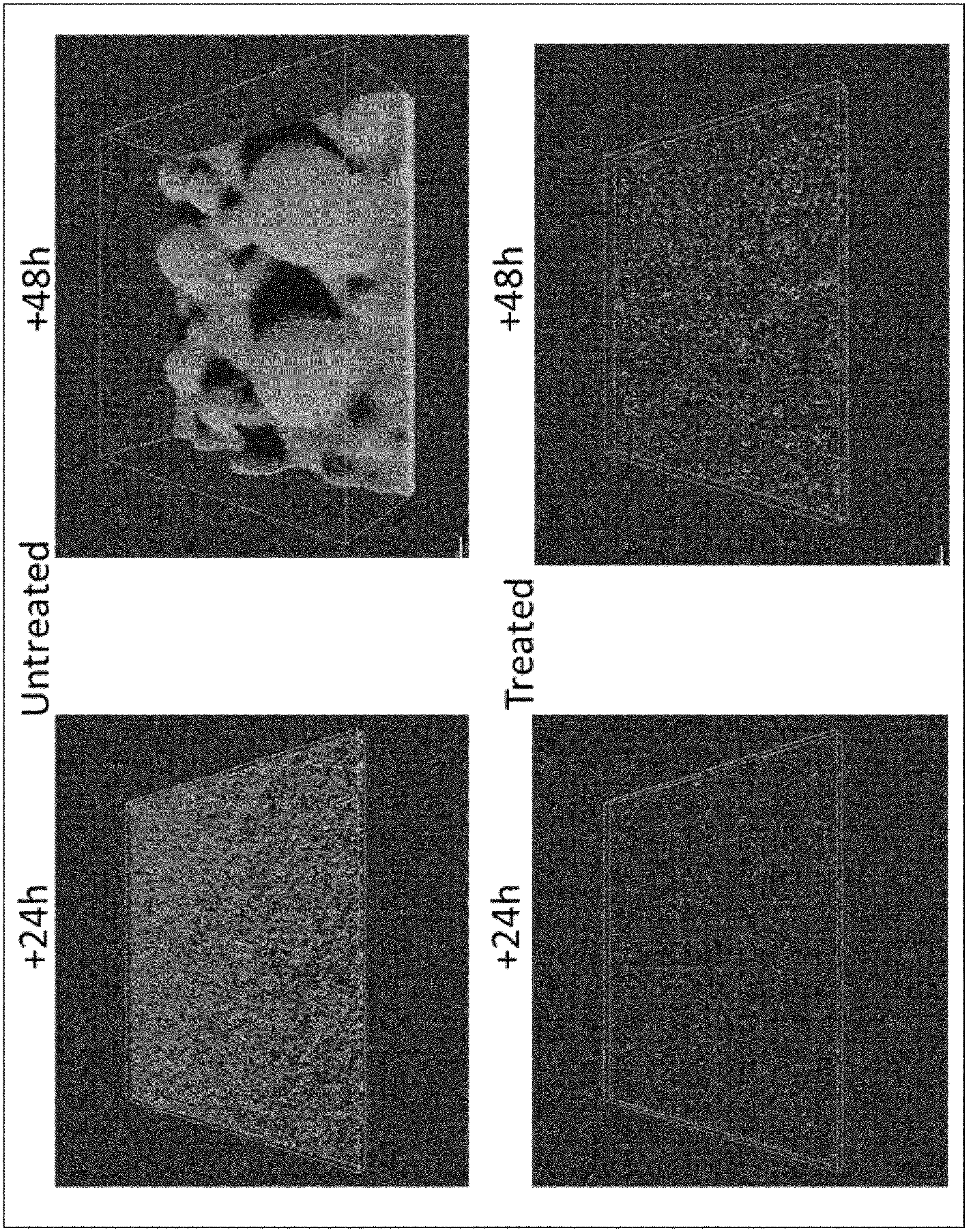
FIG. 5A shows biofilm growth and inhibition in the absence (untreated) and presence (treated) of 25 μM of H6-335-P1.

In the biofilm flow-through cells, the presence of 25 μM H6-335-P1 in the growth medium significantly prevented biofilm formation as shown in FIG. 5A.

Figure 5B:
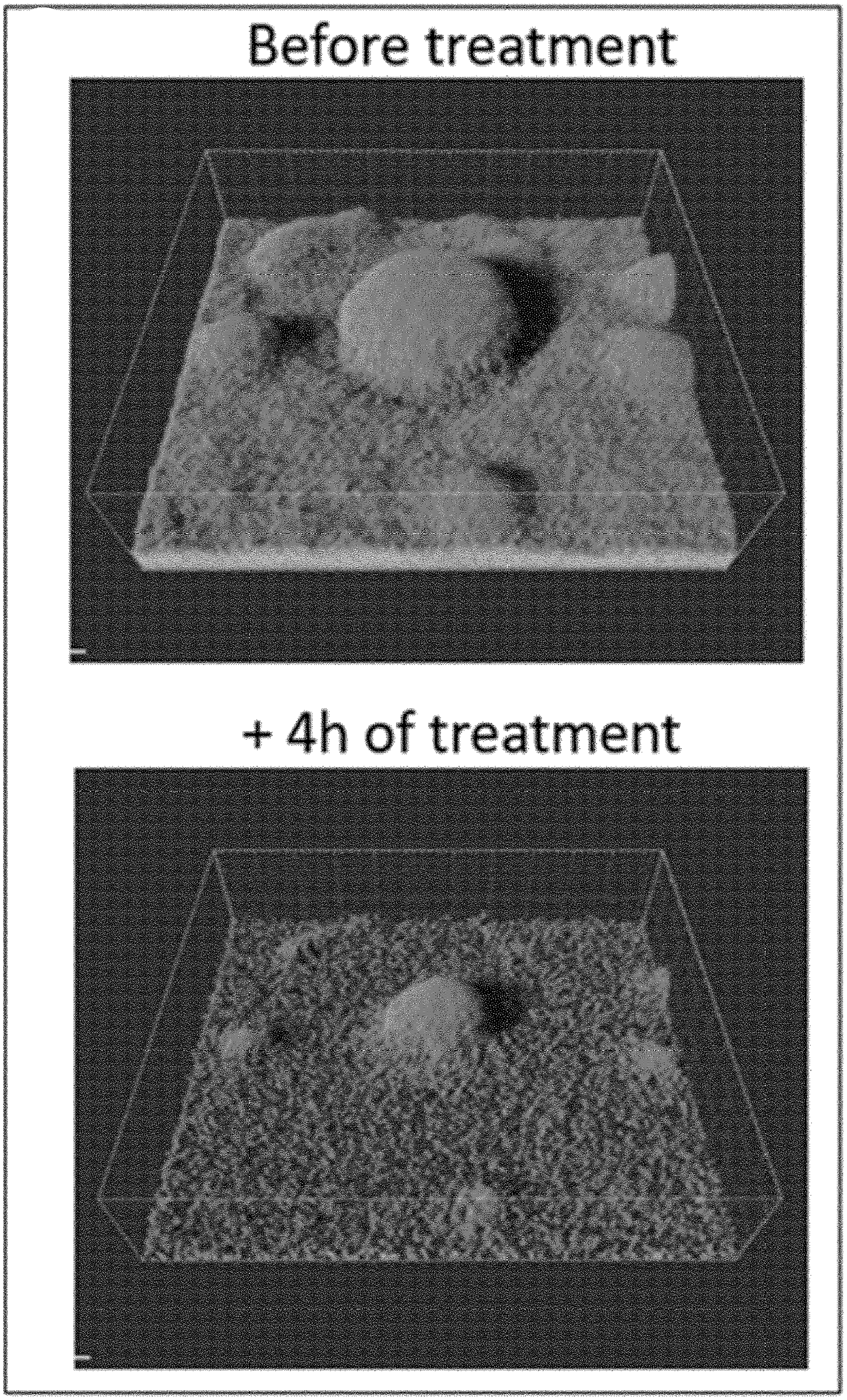
FIG. 5B shows biofilm growth and dispersal before (before treatment) and 4 hours after (+4 h of treatment) exposure to 25 μM of H6-335-P1.

In order to demonstrate dispersal of already formed biofilm after exposure to H6-335-P1, biofilms were grown in the absence of H6-335-P1 for 48 hours (before treatment) and then exposed to 25 μM of H6-335-P1 for 4 hours (+4 h of treatment). Confocal laser scanning microscopy was used to image the biofilm immediately before H6-335-P1 was added, and after 4 h of H6-335-P1 treatment. Simulated fluorescence projections in 3D were generated from the image stacks using the IMARIS software package (Bitplane, Oxford Imaging, UK) and the resulting images were processed for publication using Photoshop (Adobe, USA). FIG. 5B shows that in biofilm flow-through cells, exposure of 25 μM H6-335-P1 added to the growth medium significantly reduced the biofilm biomass to 10% (biomaterial left behind) after four hours of exposure (FIG. 5B).

Example 6 (The BifA protein is the central PDE for H6-335-P1 function) For the purpose of demonstrating that BifA (c-di-GMP phosphodiesterase) is required for H6-335-P1 induced biofilm dispersal the following experiments were carried out.

The inventors obtained mutants of all *P. aeruginosa* PDEs from the Washington *P. aeruginosa* mPAO1 transposon mutant library and investigated the ability of H6-335-P1 to disperse biofilms formed by each of these mutants in microtiter trays. Using a 96 well microtiter platform, overnight cultures of wt strain mPA01 and all of the *P. aeruginosa* PDE mutants: PA0285, PA220, PA0707 (toxR), PA2818 (arr), PA3825, PA2567, PA2572, PA4781, PA5295, PA4108, PA3947 (rocR), PA1727 (mucR), PA4367 (bifA), PA4601 (morA), PA0861 (rbdA), PA3311 (nbdA), PA5017 (dipA), PA0575, PA1433, PA2072, PA3258, PA4959 (fimX), PA5442, PA2133, PA118 (PDE mutants were named according to the PAXXXX gene number that has been inactivated in the respective PDE mutants) were diluted into 100 μL ABTrace media aliquots (Pamp and Tolker-Nielsen, 2007) supplemented with 0.5% glucose, 0.5% casa amino acids and 1 μM $FeCl_3$.

The resulting cultures were incubated at 37° C. on a rotary shaker (160 RPM) and biofilms were grown for 18 hours, at which time point either 2 μL of a 5 mM H6-335-P1 in 50% DMSO (+) or 2 μL of 50% DMSO (−) were added to each well. After two subsequent hours of growth, the culture supernatants were discarded and the amounts of biofilm present in the wells were quantified by crystal violet (CV) staining (Groizeleau et al., 2016).

Figure 6A:
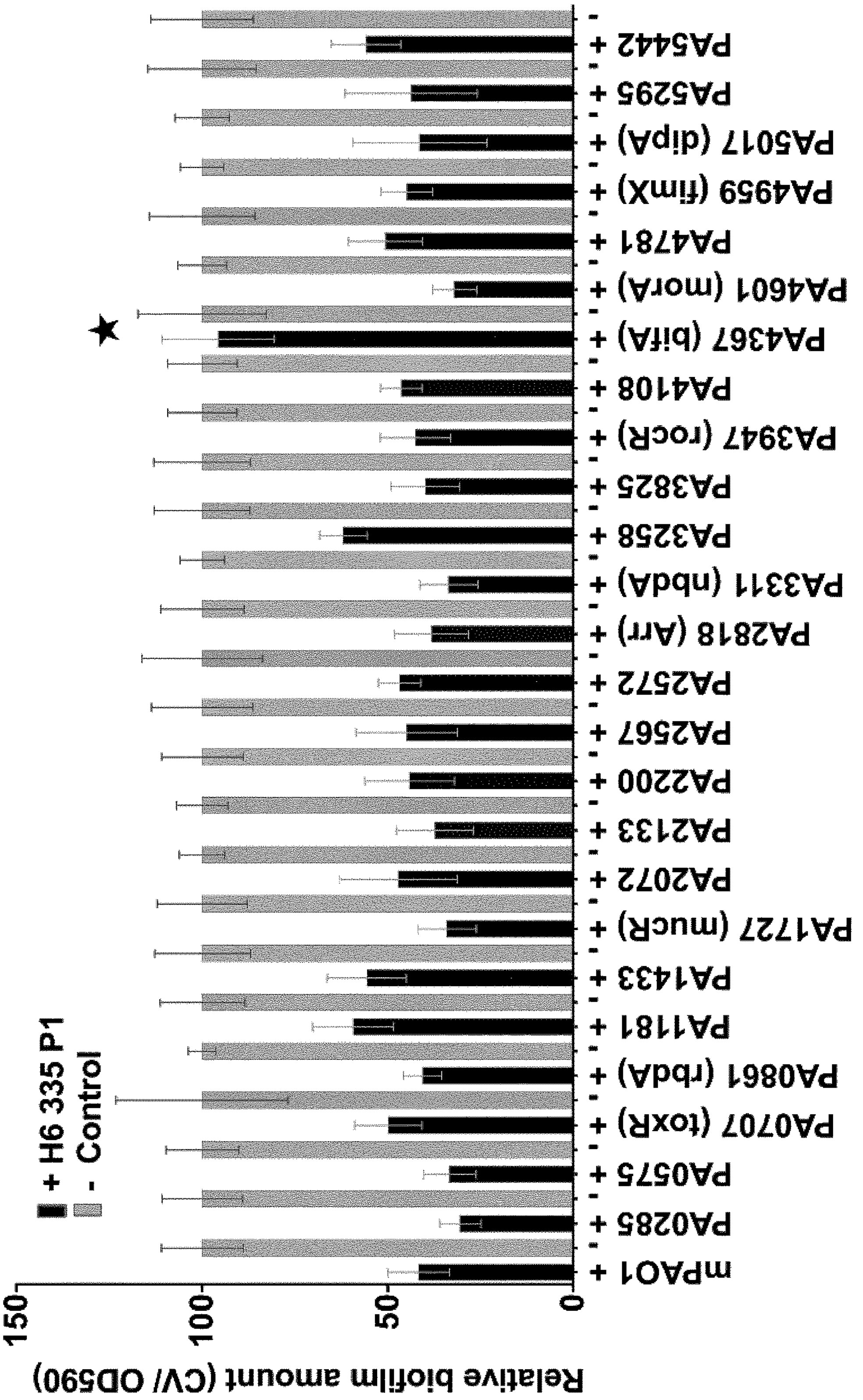
FIG. 6A shows that a functional BifA is required for H6-335-P1 induced dispersal of *P. aeruginosa* biofilm. Biofilm formed by a bifA mutant does not disperse in response to H6-335-P1 treatment, whereas biofilm formed by the wt and all other PDE mutants does disperse in response to H6-335-P1 treatment.

The amounts of biofilm prevailing after two hours of treatments were determined for the wt strain mPA01 and each of the PDE mutants. The graph presented in FIG. 6A shows relative values, where the average crystal violet (CV) value of each control (1% DMSO treatment) was arbitrarily set to 100. The range of PDE mutants tested, being mutants of all known proteins involved in synthesis and break down of c-di-GMP (Kulasekara et al., 2006), were acquired from University of Washington (The Transposon mutant collection).

As shown in FIG. 6A, the bifA mutant (PA4367 (bifA)) was the only one that did not respond to H6-335-P1 induced dispersal, whereas the biofilms formed by the *P. aeruginosa* wt and all the remaining PDE mutants dispersed in response to H6-335-P1 exposure. Together, the experiments described in this section strongly indicate that the BifA PDE contains the molecular target for H6-335-P1, binding of which strongly induces BifA's enzymatic, c-di-GMP degrading capacity.

Figure 6B:
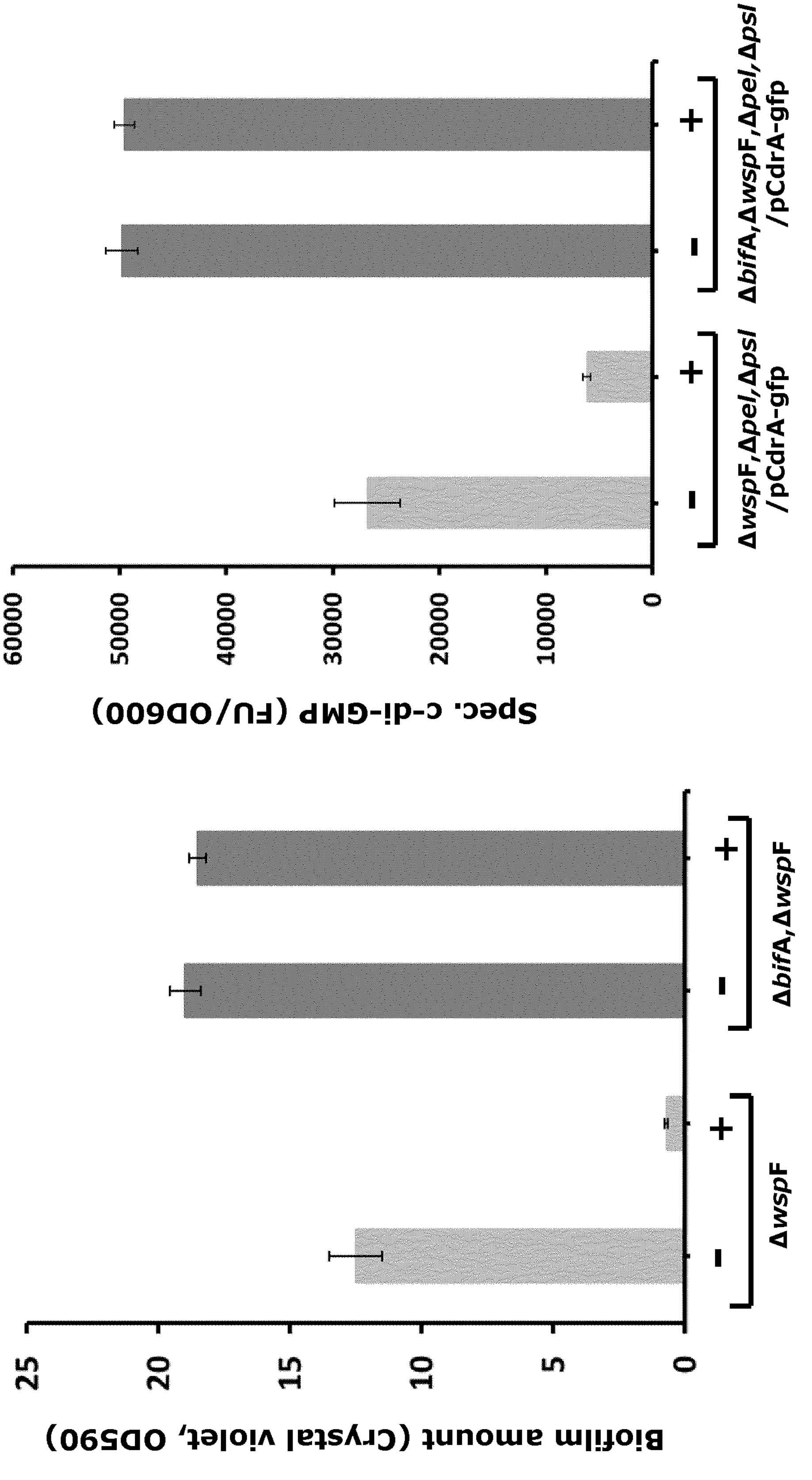
FIG. 6B shows that a functional BifA is required for H6-335-P1-mediated inhibition of biofilm formation (left graph), as well as for H6-335-P1-mediated reduction in the c-di-GMP level (right graph).

Subsequently, the inventors constructed a clean bifA knockout mutant in the *P. aeruginosa* wspF background, and could demonstrate that the constructed ΔbifAΔwspF mutant no longer responded to the presence of H6-335-P1, but formed biofilms similar to the control that was not treated with H6-335-P1 (FIG. 6B, left graph). Biofilm quantification was done using a 96 well microtiter platform where 20 hour old cultures of the deletion mutant of *P. aeruginosa* PA01 (ΔwspF) and its isogenic bifA deletion mutant (ΔbifA−) were diluted $10^6$ fold into 100 μL ABTrace media aliquots (Pamp and Tolker-Nielsen, 2007) supplemented with 0.2% glucose, 0.5% casa amino acids, 1 μM $FeCl_3$, 0.2% DMSO and either 100 μM or 0 μM of H6-335-P1. The resulting cultures were incubated at 37° C. and 160 RPM, and following 16 hours of growth the amounts of biofilm were quantified by the use of crystal violet staining. The inventors also knocked out bifA in the *P. aeruginosa* ΔwspFΔpelΔpsl/pCdrA-gfp c-di-GMP monitor strain, and found that the fluorescent read-out from the ΔbifAΔwspFΔpelΔpsl/pCdrA-gfp strain was completely unaffected by the presence of H6-335-P1, whereas 100 μM H6-335-P1 reduced the GFP read-out from the *P. aeruginosa* ΔwspFΔpelΔpsl/pCdrA-gfp monitor bacteria significantly (FIG. 6B, right graph).

This experiment was done using a 96 well microtiter format where 20 hour old cultures of the *P. aeruginosa* ΔwspFΔpelΔpsl/pCdrA-gfp c-di-GMP monitor strain and the *P. aeruginosa* ΔbifAΔwspFΔpelΔpsl/pCdrA-gfp c-di-GMP monitor strain were diluted 100 fold into 100 μL ABTrace media aliquots supplemented with 0.2% glucose, 0.5% casamino acids, 1 μM $FeCl_3$, 60 μg/mL of gentamicin, 1% DMSO and either 100 μM or 0 μM of H6-335-P1. The resulting microtiter was incubated at 37° C. and 440 RPM in a Tecan reader, and corresponding values of GFP fluorescence (FU) and cell density (OD600) was measured every 20 minutes for 24 hours. The right plot in FIG. 6B, shows the specific GFP fluorescence (FU/OD600) obtained by the respective c-di-GMP monitor strains following 18 hours of cultivation in the absence of H6-335-P1 (−) or in the presence of 100 μM H6-335-P1 (+).

Example 7 (Cloning and Over-Expression of bifA)

Figure 6C:
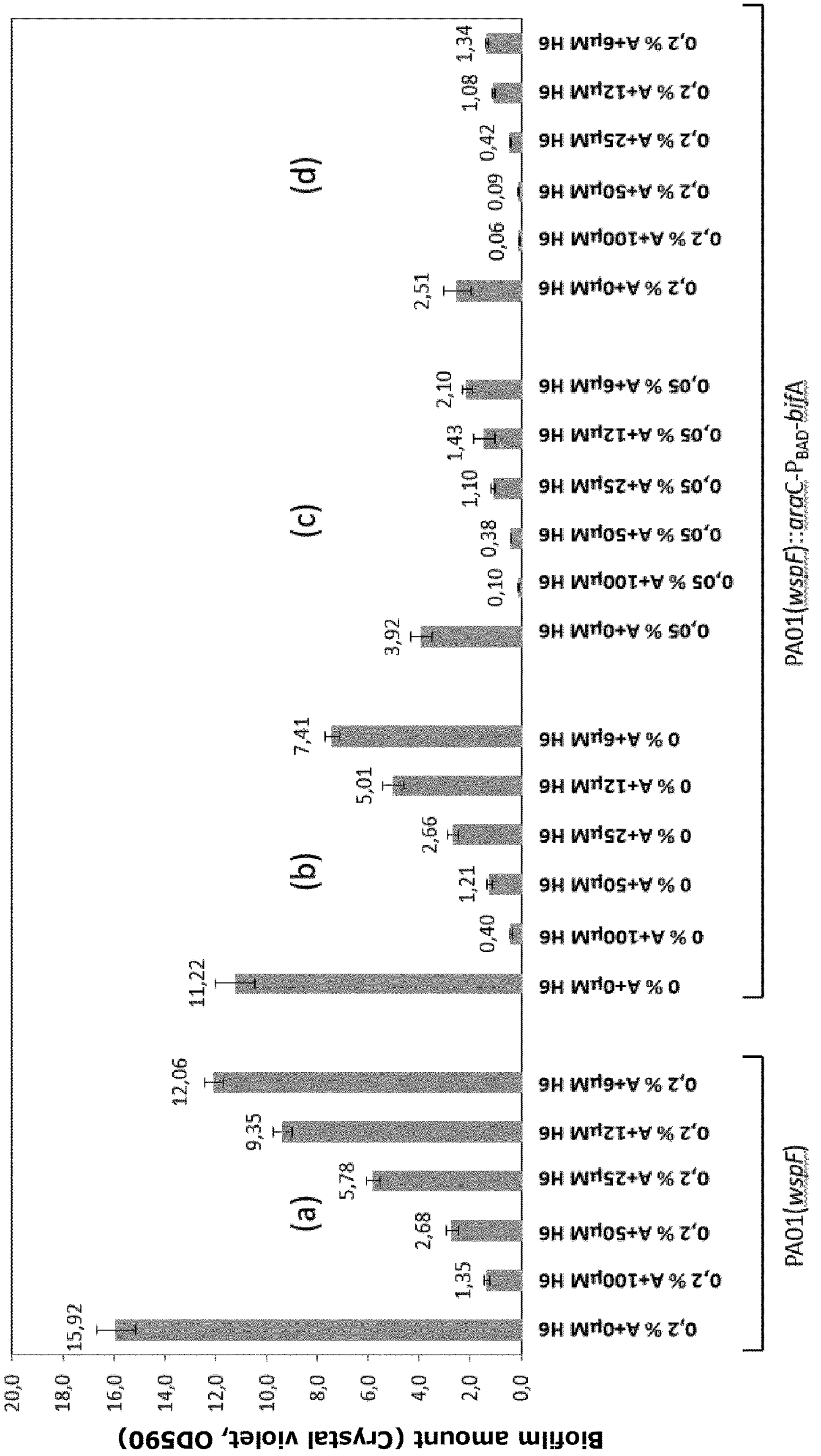
FIG. 6C shows the effect of variable bifA+ expressions and H6-335-P1 concentrations on biofilm formation of *P. aeruginosa* PA01(wspF) (a) and PA01(wspF)::araC-PBAD-bifA+ carrying an arabinose inducible bifA expression cassette (araC-$P_{BAD}$-bifA+) its chromosome) (b,c,d). The biofilm amounts prevailing following treatment with varying concentrations of arabinose and H6-335-P1 were plotted. The amounts of supplemented arabinose (0% A, 0.05% A or 0.2% A) and H6-335-P1 (100 μM, 50 μM, 25 μM, 12 μM, 6 μM or 0 μM) are indicated below the X-axis of FIG. 6C. Numbers above the bars in FIG. 6C represents the crystal violet measurements.

A further experiment, as shown in FIG. 6C, demonstrates the effect of variable bifA+ expressions and H6-335-P1 concentrations on biofilm formation of the wspF deletion mutant of *P. aeruginosa* PA01(wspF) (a) and PA01(wspF)::araC-PBAD-bifA+ carrying an arabinose inducible bifA expression cassette (araC-PBAD-bifA+) on its chromosome) (b,c,d).

Using a 96 well microtiter platform, overnight cultures of the strains were diluted 200 fold into 100 uL ABTrace media aliquots (Pamp and Tolker-Nielsen, 2007) supplemented with 0.2% glucose, 0.5% casa amino acids, 1 μM $FeCl_3$, 1% DMSO and varying concentrations of arabinose and H6-335-P1.

The resulting microtiter plates were sealed with air permeable lids and biofilm cultures were grown at 37° C. on a rotary shaker (280 RPM) for 18 hours, after which the culture supernatants were discarded and biofilm present in the wells were quantified by crystal violet staining (Groizeleau et al., 2016).

Finally, biofilm prevailing following treatment with varying concentrations of arabinose and H6-335-P1 were plotted. The amounts of supplemented arabinose (0% A, 0.05% A or 0.2% A) and H6-335-P1 (100 μM, 50 μM, 25 μM, 12 μM, 6 μM or 0 μM) are indicated below the X-axis of FIG. 6C. Numbers above the bars in FIG. 6 represents the crystal violet measurements.

The PA01 bifA gene and its native ribosome binding site were initially cloned into the arabinose inducible expression vector pJN105 to give pJBAMG10. Expression of pJBAMG10-borne bifA in a bifA knock-out background restored H6-335-P1 mediated reduction in c-di-GMP, induced biofilm dispersal and inhibited biofilm formation as seen with the wt PA01 strain and the wspF mutant strain (not shown). From this plasmid, the inventors next constructed a wspF strain carrying a copy of an arabinose inducible bifA+ expression cassette, araC-PBAD-bifA+, located in the CTX site of its chromosome.

In the absence of arabinose, the wspF::araC-PBAD-bifA strain was observed to form less biofilm than the ΔwspF parent ((a) and (b) of FIG. 6C) indicating that the expression of BifA from the araC-PBAD-bifA cassette is leaky, and that the resulting basal expression of BifA is capable of reducing the c-di-GMP content and subsequent biofilm formation. A further rise in bifA expression induced by addition of arabinose ((b), (c), (d) of FIG. 6C)) increased inhibition of biofilm formation even in the absence of added H6-335-P1. Addition of H6-335-P1 to the arabinose stimulated cultures created a synergistic inhibitory effect on biofilm formation (FIG. 6C).

The results of the above described experiments support that the BifA protein is the primary and only target of H6-335-P1. H6-335-P1 may therefore directly interact with and activate (in a concentration dependent manner) BifA to degrade c-di-GMP.

Example 8 (In Vitro Experiment)

The below described in vitro experiments was carried out in order to demonstrate that H6-335-P1 exposure improves subsequent antibiotic (tobramycin and ciprofloxacin) kill of biofilms and dispersed biofilm bacteria.

Figure 7:
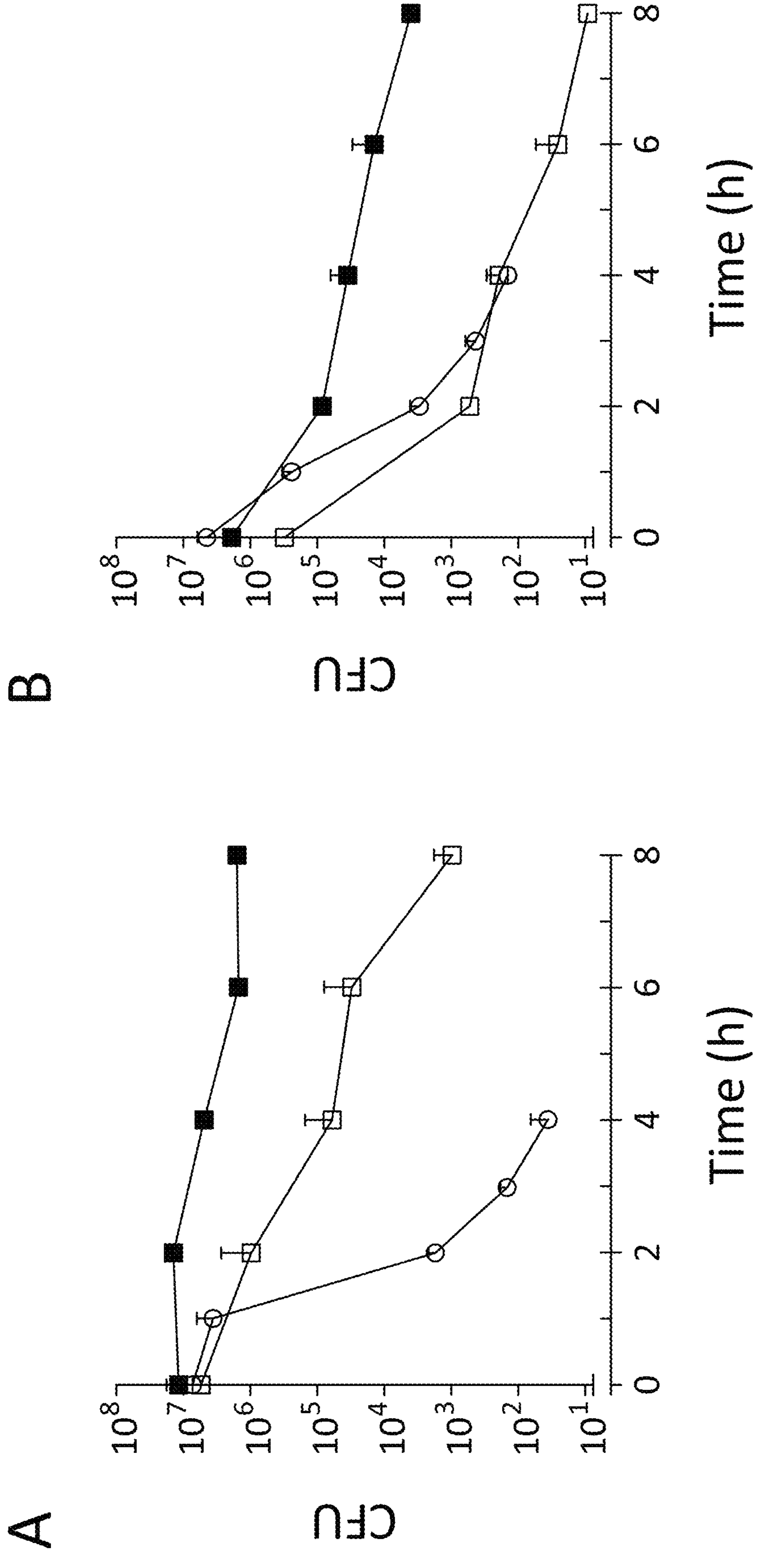
FIG. 7A shows time dependent antibiotic killing assay of *P. aeruginosa* biofilms and of planktonic cells, originated from H6-335-P1 treated biofilms, exposed to 30 μg/ml tobramycin.
FIG. 7B shows time dependent killing assay of *P. aeruginosa* biofilms and of planktonic cells, originated from H6-335-P1 treated biofilms, exposed to 0.5 μg/ml ciprofloxacin. Biofilms were grown on pegs and subsequently treated with and without H6-335-P1. Biofilms treated with H6-335-P1 (open squares) and without H6-335-P1 (filled squares) as well as their planktonic cells (open circles) were challenged with antibiotics. The biofilms were disrupted at 0, 2, 4, 6 and 8 hour and planktonic cells were withdrawn at 0, 1, 2, 3 and 4 hours, diluted and spotted on LB-agar plates for CFU determination. The data are averages of three replicates. Bars indicate standard deviations.

The inventors performed a variety of experiments to support the hypothesis that an efficient biofilm dispersing compound would promote the efficacy of conventional antibiotics. Such in vitro experiments are shown in FIGS. 7A (with tobramycin) and 7B (with ciprofloxacin).

*P. aeruginosa* biofilms were cultivated, with agitation (110 RPM) in ABTrace medium supplemented with 0.5% glucose, 0.5% casamino acids and 1 μM $FeCl_3$ for 24 hours at 37° C., on polystyrene pegs protruding down from plastic lids into microtiter plates. The biofilm coated pegs were washed and placed for 2 hours in medium supplemented with either 100 μM H6-335-P1 or without any H6-335-P1 and then subsequently washed and challenged with medium containing either tobramycin (FIG. 7A) or ciprofloxacin (FIG. 7B).

The addition of H6-335-P1 mediates dispersion of bacteria from the biofilms. Thereafter, the biofilms and dispersed/planktonic bacteria were separately treated with tobramycin or ciprofloxacin (tobramycin and ciprofloxacin are two clinically relevant antimicrobials used to treat *P. aeruginosa* infections in e.g. cystic fibrosis (CF) patients), i.e. 30 μg/ml tobramycin (MIC value of 1 μg/ml) and 0.5

μg/ml ciprofloxacin (MIC value of 0.125 μg/ml), respectively, with and without H6-335-P1.

The number of surviving bacterial cells (colony forming units (CFUs)) from sonication-disrupted biofilms were determined by plating samples on agar plates at intervals during a time period of 4 hours. The number of viable dispersed/planktonic bacteria (CFUs) were determined by plating samples on agar plates at intervals during a time period of 8 hours. CFUs were counted after overnight incubation of the agar plates.

More specifically, the inventors observed a time dependent antibiotic killing assay of *P. aeruginosa* biofilms and of planktonic cells, originating from H6-335-P1 treated biofilms, exposed to 30 μg/ml tobramycin (FIG. 7A). Likewise, FIG. 7B shows time dependent killing assay of *P. aeruginosa* biofilms and of planktonic cells, originating from H6-335-P1 treated biofilms, exposed to 0.5 μg/ml ciprofloxacin.

The experiments demonstrated that dispersed/planktonic cells were rapidly killed in a time dependent manner. Antibiotic mediated killing only showed a marginal kill-effect on biofilms that had not been treated with H6-335-P1, whereas there was a substantial decrease of surviving cells originating from biofilms treated with H6-335-P1.

The outcome of the experiments illustrates that dispersed cells from the biofilms are released to the growth medium where they (in contrast to the biofilms) get efficiently killed by the antibiotics. In addition, improved access to the remaining bacteria (those that were not liberated by H6-335-P1 exposure) promotes antibiotic mediated killing of the remaining biofilms.

Example 9 (In Vivo Experiment)

The below in vivo experiments were carried out in mice, in order to demonstrate that H6-335-P1 exposure improves subsequent antibiotic (tobramycin and ciprofloxacin) kill of biofilms and dispersed biofilm bacteria.

The inventors first determined H6-335-P1 anti-biofilm efficacy in implant-harboring mice at low dosages (concentration) of 5 to 25 μM H6-335-P1 which corresponds to 1 to 5 μg H6-335-P1 per gram of body weight. *P. aeruginosa* biofilms were allowed to form on implants in the mouse intraperitoneal cavity during 24 hours after implant insertion, after which mice were given either placebo or experimental drug (H6-335-P1) as intraperitoneal injections (in the opposite site of the implant). After the treatments, the implants were removed and the bacteria remaining on the implants were enumerated as CFU (colony forming units).

Similar to the in vitro investigations above, four hours of exposure to H6-335-P1 reduced the number of cells on the implant, indicating that up to 90% of the biofilm bacteria had been dispersed (not shown).

Next the inventors conducted a series of in vivo experiments with combinatorial treatments. The inventors decided to focus on H6-335-P1 for anti-biofilm efficacy in mice at low dosages (concentration) of 5 to 25 μM H6-335-P1, which corresponds to 1 to 5 μg H6-335-P1 per gram of body weight.

Figure 8:
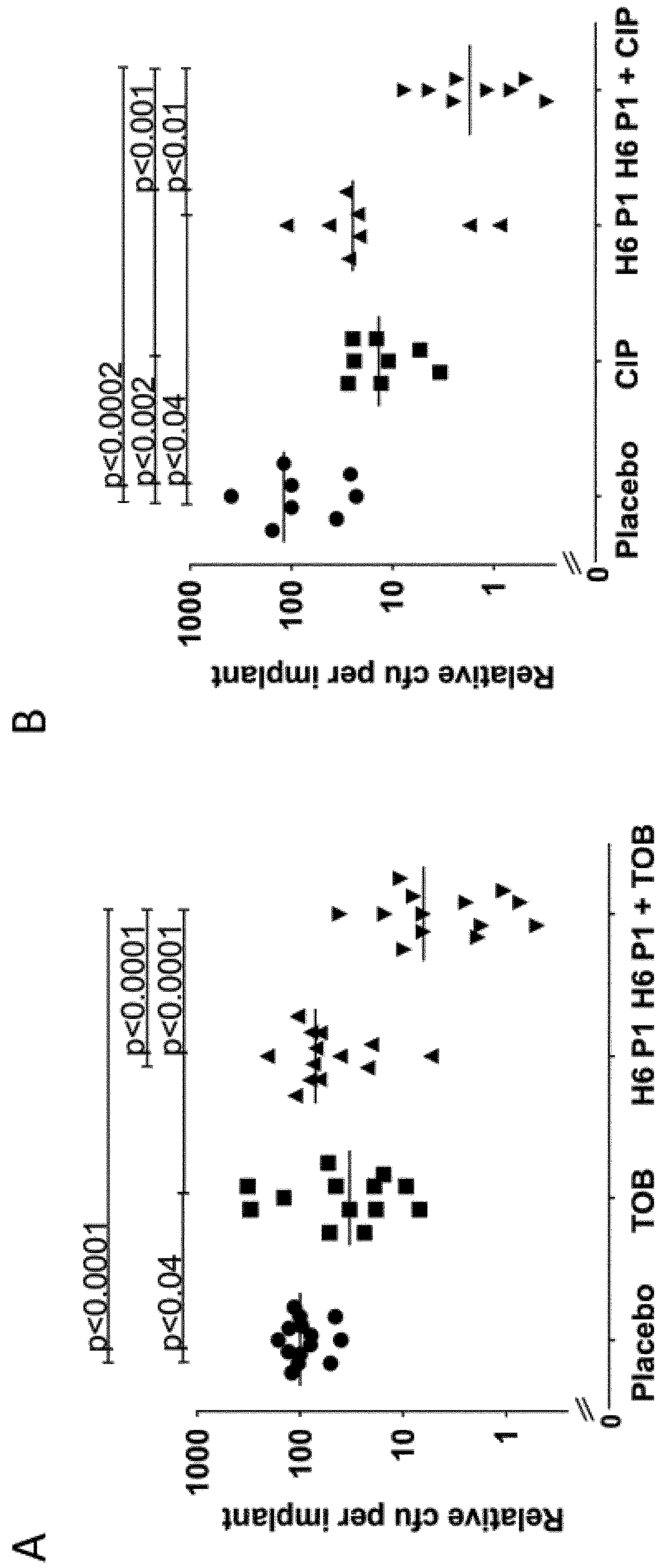
FIG. 8 shows bacterial contents on *P. aeruginosa*-infected peritoneal implants after treatment with H6-335-P1 and/or tobramycin/ciprofloxacin. Silicone implants (5 mm long, 6 mm OD×4 mm ID) were incubated with *P. aeruginosa* cultures (OD 0.1) for 20 hours to allow bacterial adhesion and subsequent coating. At time t=0, mice had the implants inserted in the peritoneal cavity and biofilm developed on the implants for 24 hours. (A) At 24 hours and 26 hours post-insertion of the implants (PI), the mice were treated with either H6-335-P1 (named "H6 P1" in FIG. 8) 25 μM (~6 μg/g BW) in 0.2% cyclodextrin or 0.2% cyclodextrin, and at 26 hours PI with 30 μg per g BW tobramycin (TOB) or 0.9% NaCl. (B) At 24 hours and 26 hours PI mice were treated with either H6-335-P1 25 μM (~6 μg/g BW) in 0.2% cyclodextrin or 0.2% cyclodextrin, and at 24 hours PI with either 10 μg per g BW ciprofloxacin (CIP) or 0.9% NaCl. At 28 hours PI the mice were euthanized, and the bacterial contents as CFU per implant were determined. The median CFU per implant for the placebo group was set to 100. The median CFU per implant for the placebo groups were $8.5\times10^6$ (A) and $1.5\times10^6$ (B). Horizontal lines indicate median CFU for each group. Each symbol represents a mouse. Significance levels are based on Mann-Whitney U test (analysis of non-parametric data). IP administered doses: TOB: 30 mg/Kg BW, CIP: 10 mg/Kg BW, H6 P1: 2×6 mg/Kg BW.

As shown in FIG. 8 the *P. aeruginosa* biofilms formed on the implants during 24 hours of insertion where first given either placebo or the H6-335-P1 drug, then subsequently either tobramycin or ciprofloxacin were administered to the mice also as intra-peritoneal injections (for details, see axis labels to FIG. 8).

CFU enumeration of the removed implants showed that combinatorial treatments with the non-antibiotic dispersal drug H6-335-P1 followed by antibiotic treatment had synergistic antimicrobial (lethal) effects. The results indicate that the significant reduction in the biofilm mass resulting from the H6-335-P1 treatments offers improved access to the subsequent administered antibiotics which results in an improved kill of the bacteria.

Combinatorial treatment with meropenem and H6-335-P1 gives similar results (not shown).

Example 10 (Improved Aqueous Solubility of H6-335-P1 (Formulation))

H6-335-P1 has a low solubility in aqueous media (<2 μM). Low aqueous solubility is a well-known problem encountered with formulation development of new chemical entities aiming at drug development. More than 40% of new chemical entities developed in the pharmaceutical industry are practically insoluble in water (Savjani et al., 2012).

H6-335-P1 can be solubilized in DMSO as a stock solution and then subsequently diluted into aqueous media to the desired concentrations. All the above described in vitro experiments including the SAR analysis have been performed this way.

H6-335-P1 can be dissolved in the vehicle cyclodextrin ((2-Hydroxypropyl)-β-cyclodextrin) as a stock and subsequently diluted to the desired concentration in aqueous medium making it suitable for the in vivo animal experiments as shown in FIG. 8.

Figure 9:
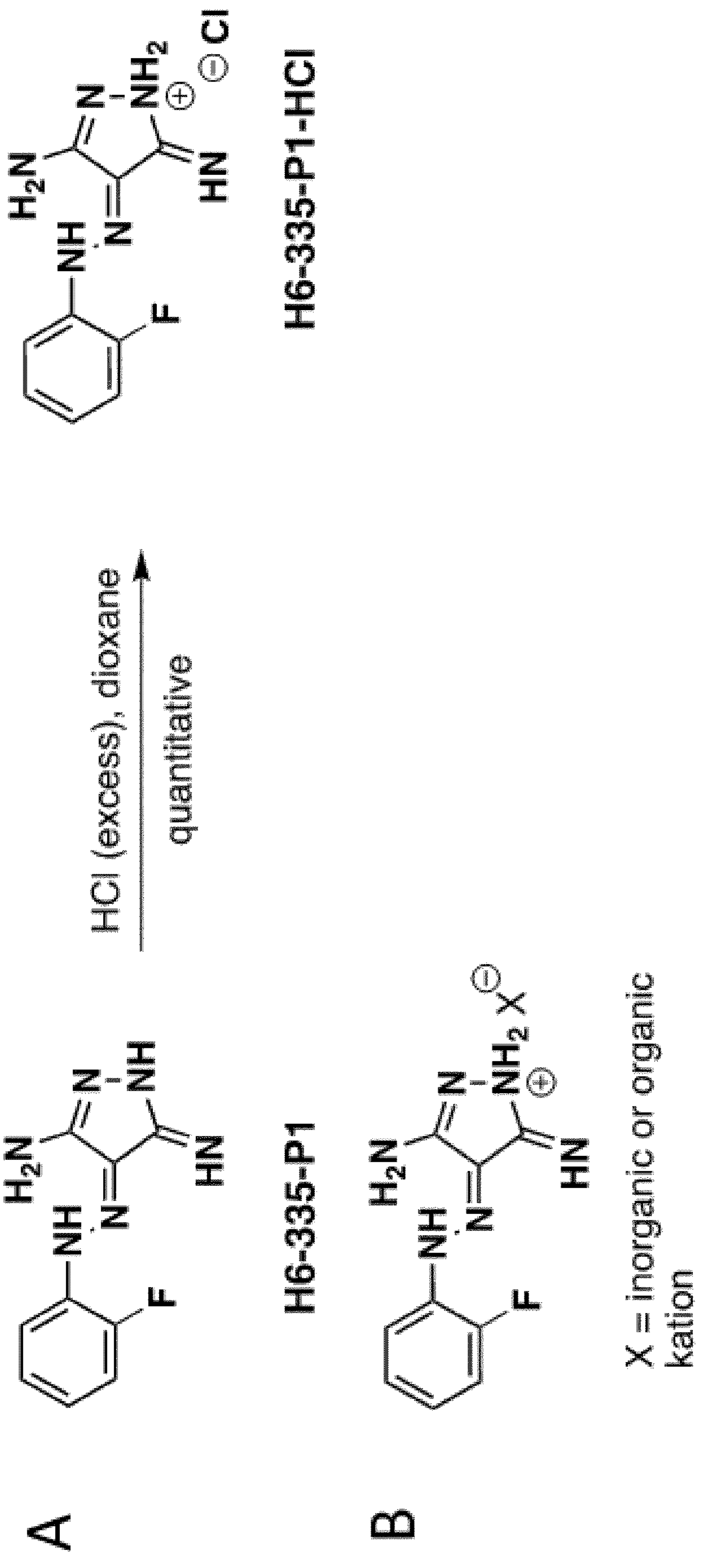
FIGS. 9A and 9B show the synthesis of the water soluble salt H6-335-Pl-HCl.

All SAR tested compounds showed low solubility in aqueous media. To enable solubility of H6-335-P1 directly into an aqueous medium, the inventors formulated a variety of different salts of H6-335-P1, with the HCl salt (H6-335-P1:HCl) being the top candidate, both with respect to biological activity and solubility directly into aqueous media (see FIGS. 9A and 9B and the table 3 below).

TABLE 3

| (different salts of H6-335-P1) | |
|---|---|
| 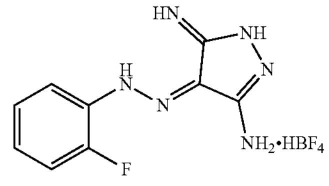 ($HBF_4$ salt of H6-335-P1) | Solubility in DMSO: n/a<br>Solubility in $H_2O$: n/a<br>74% reduction in c-di-GMP content (compound dissolved from DMSO stock)<br>75% reduction in c-di-GMP (compound dissolved directly in $H_2O$) |

TABLE 3-continued

| (different salts of H6-335-P1) | |
|---|---|
| 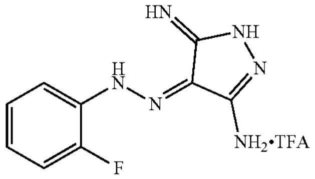<br>(TFA salt of H6-335-P1) | Solubility in DMSO: n/a<br>Solubility in $H_2O$: n/a<br>74% reduction in c-di-GMP content<br>(compound dissolved from DMSO stock)<br>75% reduction in c-di-GMP<br>(compound dissolved directly in $H_2O$) |
| 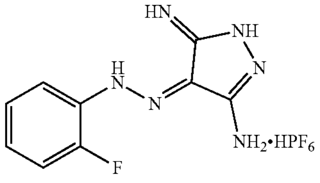<br>($HPF_6$ salt of H6-335-P1) | Solubility in DMSO: n/a<br>Solubility in $H_2O$: n/a<br>77% reduction in c-di-GMP content<br>(compound dissolved from DMSO stock)<br>74% reduction in c-di-GMP<br>(compound dissolved directly in $H_2O$) |
| 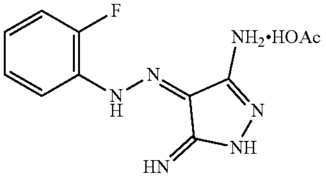<br>(acetic acid salt of H6-335-P1) | Solubility in DMSO: n/a<br>Solubility in $H_2O$: n/a<br>74% reduction in c-di-GMP<br>(compound dissolved directly in $H_2O$)<br>(not tested in DMSO) |
| 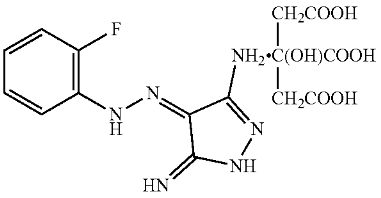<br>(citric acid salt of H6-335-P1) | Solubility in DMSO: n/a<br>Solubility in $H_2O$: 0.03 mM<br>66% reduction in c-di-GMP content<br>(compound dissolved from DMSO stock)<br>64% reduction in c-di-GMP<br>(compound dissolved directly in $H_2O$) |
| 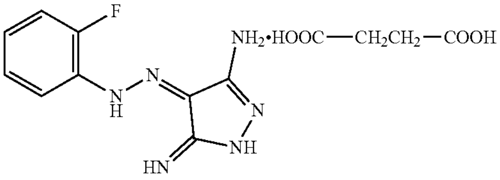<br>(succinic acid salt of H6-335-P1) | Solubility in DMSO: n/a<br>Solubility in $H_2O$: 0.02 mM<br>23% reduction in c-di-GMP content<br>(compound dissolved from DMSO stock)<br>19% reduction in c-di-GMP<br>(compound dissolved directly in $H_2O$) |
| 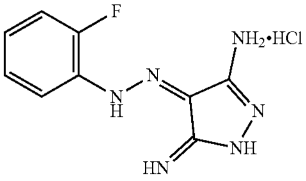<br>(HCl salt of H6-335-P1, H6-335-P1:HCl) | Solubility in DMSO: n/a<br>Solubility in $H_2O$: 3.41 mM<br>71% reduction in c-di-GMP content<br>(compound dissolved from DMSO stock)<br>74% reduction in c-di-GMP<br>(compound dissolved directly in $H_2O$) |
| 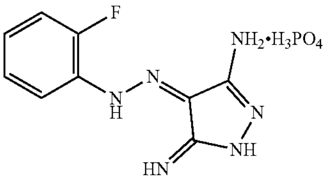<br>($H_3PO_4$ salt of H6-335-P1) | Solubility in DMSO: n/a<br>Solubility in $H_2O$: 5.73 mM<br>64% reduction in c-di-GMP content<br>(compound dissolved from DMSO stock)<br>66% reduction in c-di-GMP<br>(compound dissolved directly in $H_2O$) |

TABLE 3-continued

| (different salts of H6-335-P1) | |
|---|---|
| 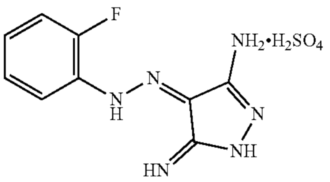 ($H_2SO_4$ salt of H6-335-P1) | Solubility in DMSO: n/a<br>Solubility in $H_2O$: 4.21 mM<br>68% reduction in c-di-GMP content (compound dissolved from DMSO stock)<br>65% reduction in in c-di-GMP (compound dissolved directly in $H_2O$) |

Example 11 (Treatment of Catheter Associated Urinary Tract Infection in Mice (In Vivo))

Figure 10A:
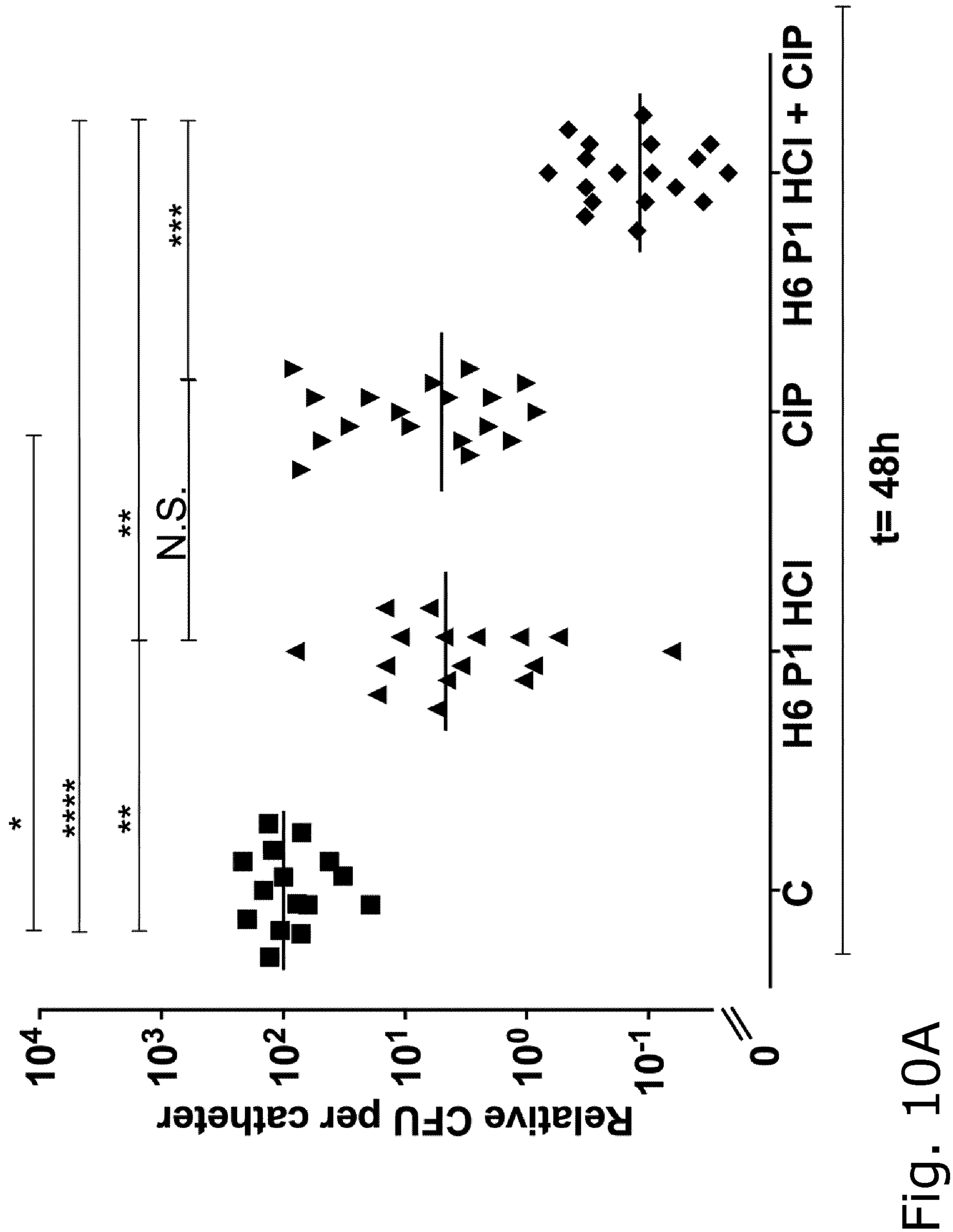
FIG. 10A shows bacterial contents on *P. aeruginosa*-infected urinary tract catheters after treatment with H6-335-P1 and/or ciprofloxacin. Silicone catheters (5 mm long, 0.64 mm OD×0.3 mm ID) incubated with *P. aeruginosa* cultures (OD 1) for 22 hours to allow bacterial adhesion and subsequent coating. Mice then had the catheters inserted in the bladder and biofilm developed on the catheters for 24 hours. At 24 hours and 36 hours post-insertion (PI) the mice were treated with either H6-335-P1-HCl (50 μM~13 μg/g BW) or 0.9% NaCl alone, and at 25 hours and 37 hours PI 1 μg per g BW ciprofloxacin (CIP) or 0.9% NaCl. At 48 hours post-insertion the mice were euthanized, and the bacterial contents as CFU per implant were determined. Two experiments were pooled, and the median CFU per implant for the placebo group was set to 100. Horizontal lines indicate median CFU for each group. Each symbol represents a mouse. IP administered doses: H6 P1: 2×13 mg/Kg BW, CIP: 2×1 mg/Kg BW.

H6-335-P1 anti-biofilm efficacy was also determined on silicone catheters inserted in the bladders of mice (FIG. 10A).

The biofilms were allowed to form on the catheters during 24 hours of insertion in the mouse bladder, after which mice were given either H6-335-P1: HCl or 0.9% NaCl as intraperitoneal injections, at 24 hours and 36 hours post-insertion (PI). In addition, mice were treated with 1 μg per g BW ciprofloxacin (CIP) or 0.9% NaCl, at 25 hours and 37 hours PI. At 48 hours PI the mice were euthanized, and the catheters were removed to determine the bacteria remaining on the catheters, enumerated as CFUs.

Similar to experiments with the implant model, the inventors found that exposure to H6-335-P1 reduced the number of bacteria on the catheters. The results again indicate that the significant reduction in the biofilm mass resulting from the H6-335-P1 treatments offers improved access to the subsequent administered antibiotics which results in an improved kill of the bacteria.

This indicates that the host immune system of the mice facilitates clearing of the bacteria from the catheter after dispersal. Interestingly, the results also indicate that formulation of H6-335-P1 as an HCl salt not only improves the solubility in aqueous media, but also improves the anti-biofilm properties in comparison to H6-335-P1 dissolved and administered with cyclodextrin.

Example 11a (Oral Administration of H6-335-P1: HCl)

Figure 10B:
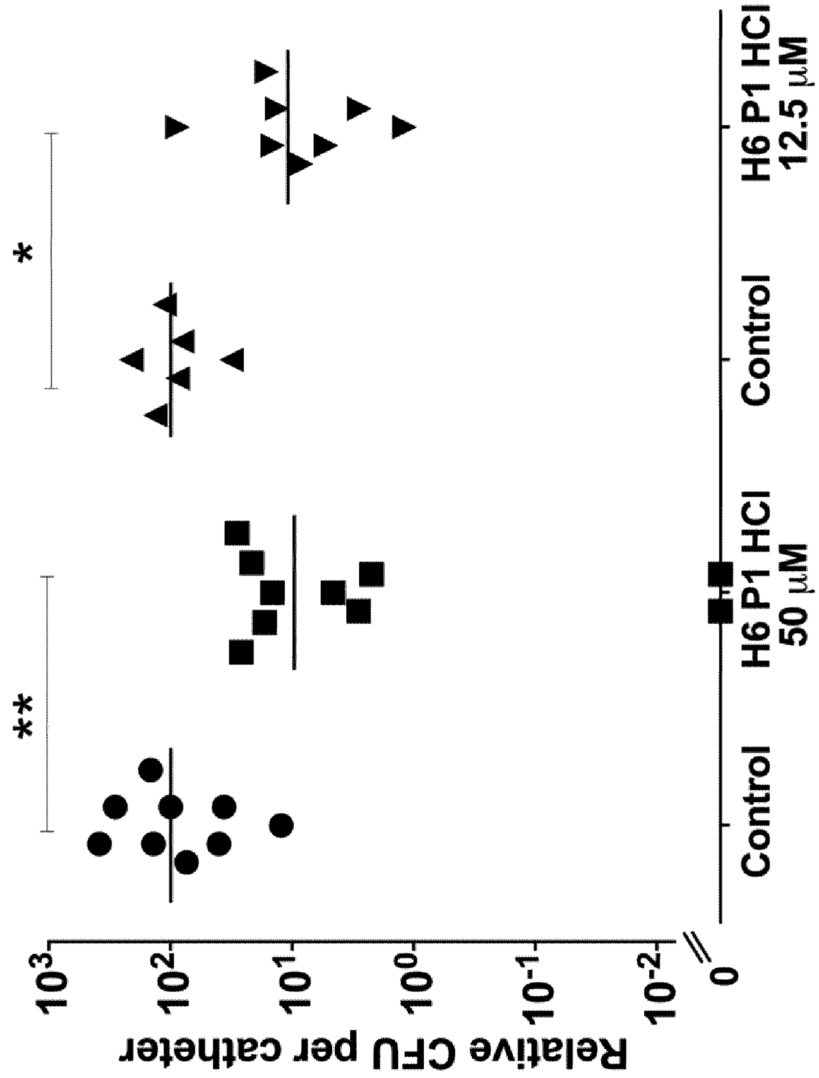
FIG. 10B shows bacterial contents on *P. aeruginosa*-infected urinary tract catheters after oral administration with H6-335-P1 in Nutella or Nutella (control). Silicone catheters (5 mm long, 0.64 mm OD×0.3 mm ID) incubated with *P. aeruginosa* cultures (OD 1) for 22 hours to allow bacterial adhesion and subsequent coating. Mice then had the catheters inserted in the bladder and biofilm developed on the catheters for 24 hours. At 24 hours and 36 hours post-insertion (PI) the mice were given Nutella with H6-335-P1-HCl (12.5 μM or 50 μM corresponding to 3.25 μg/g BW and 13 μg/g BW, respectively) or Nutella alone. At 48 hours post-insertion the mice were euthanized, and the bacterial contents as CFU per implant were determined. Two experiments are shown in the figure. The median CFU per catheter for the control groups were set to 100. The median CFU per catheter for the placebo groups were $3\times10^5$ and $7\times10^4$. Horizontal lines indicate median CFU for each group. Each symbol represents one mouse. Orally administered doses: 2×13 mg/Kg BW, 2×3.3 mg/Kg BW.

To demonstrate oral administration efficacy in vivo, we used a catheter associated urinary tract infection model (FIG. 10B).

The biofilms were allowed to form on the catheters during 24 hours of insertion in the mouse bladder, after which mice were given either Nutella with H6-335-P1:HCl or Nutella (control), at 24 hours and 36 hours post-insertion (PI). At 48 hours PI the mice were euthanized, and the catheters were removed to determine the bacteria remaining on the catheters, enumerated as CFUs. Two different experiments were carried out, one where the mice received 50 μM H6-335-P1: HCl in Nutella (corresponds to 13 mg/Kg BW) or Nutella, and one where the mice received 12.5 μM H6-335-P1: HCl in Nutella (corresponds to 3.3 mg/Kg BW) or Nutella (FIG. 10B)

Similar to the CAUTI experiment with intraperitoneal administration, the inventors found that exposure to H6-335-P1 by oral administration reduced the number of bacteria on the catheters. The results show that oral administration of H6-335-P1 as low as 12.5 μM (~3.25 μg/g BW or 3.3 mg/Kg BW) significantly reduces the biofilm mass on the catheters, and that 13 mg/Kg and 3.3 mg/Kg gives similar results. We found that H6-335-P1:HCl is up-concentrated in the urine, why 12.5 μM is sufficient to obtain the maximal biological activity (data not shown).

Example 12 (Further Means of Identifying the Target of H6-335-P1)

These experiments were carried out to further demonstrate that the c-di-GMP phosphodiesterase BifA is central and the target for H6-335-P1 induced enzymatic activity.

The inventors employed mutational analysis with the aim of identifying a putative target of H6-335-P1. The compound Congo Red (CR) binds to exopolymers whose production is positively regulated by c-di-GMP in *P. aeruginosa* (Friedman, L., and R. Kolter. 2003.

Genes involved in matrix formation in *Pseudomonas aeruginosa* PA14 biofilms. Molecular Microbiology 51:675-690). Thus, the inventors exploited that a *P. aeruginosa* wspF mutant forms dark red colonies when cultivated on CR agar plates, but forms white colonies if cultivated on CR plates supplemented with 100 μM H6-335-P1.

The inventors constructed a Mariner transposon mutant library in the *P. aeruginosa* wspF background and spread the resulting 32.000 transposon mutants onto CR plates supplemented with H6-335-P1. Two days later, visual inspection of the agar plates revealed that the large majority of the transposon mutants gave rise to white colonies as expected, whereas 260 mutants displayed a red colony phenotype in the presence of H6-335-P1. Biofilm inhibition assays performed on all 260 mutants showed that only one of the mutants no longer responded to the presence of H6-335-P1, and formed biofilms similar to the control that was not treated with H6-335-P1 (data not shown). The inventors sequenced and determined the transposon insertion point in the mutant that did not respond to H6-335-P1 as well as in 67 of the other mutants that formed red colonies on plates with H6-335-P1.

In the mutant that did not respond to H6-335-P1 the transposon resided in the coding sequence of the bifA gene. In the 67 other mutants that formed red colonies on agar plates with CR and H6-335-P1, the transposon insertions were found to reside in genes mainly involved in lipopolysaccharide and polysaccharide synthesis, and their regulatory functions (data not shown). Apparently, all these mutations results in the formation of red colonies on agar plates with CR and H6-335-P1, but only the bifA mutation resulted in an inability to respond to H6-335-P1 in biofilm formation assays. These experiments therefore corroborate that BifA is the target of H6-335-P1.

Mariner transposon mutagenesis in the *P. aeruginosa* ΔwspF strain was done using the protocol of Kulasekara (Kulasekara, H. D. 2014. Transposon mutagenesis. Methods Mol Biol 1149:501-519). Briefly, following a 2 hours of biparental mating between *P. aeruginosa* ΔwspF and *E. coli* S17-λpir/pBT20 on LB plates, the conjugation spots were collected and resuspended in 0.9% NaCl. Then 32×200 μl aliquots of the conjugation mixture were spread onto 15 cm wide LB plates supplemented with 1% agar, 20 μg/ml Commassie Blue, 40 μg/ml Congo Red, 60 μg/ml gentamicin and 100 μM H6-335-P1. The plates were subsequently incubated at 37° C. for two days, which resulted in the formation of approximately 32,000 transposon mutant colonies. The chromosomal insertion site of the mariner transposon in selected mutants was identified by sequencing, using the two step arbitrary PCR protocol described by Kulasekara (Kulasekara, H. D. 2014. Transposon mutagenesis. Methods Mol Biol 1149:501-519).

Example 13 (Host Range of H6-335-P1)

To determine the host range of H6-335-P1, the inventors conducted a Blast search for analogs of the *P. aeruginosa* BifA phosphodiesterase protein encoded by gene PA4367 (bifA). The Blast search revealed that the BifA protein is conserved among the pseudomonads, but is not widespread in other bacterial species (data not shown). In support of the Blast result, the inventors found that H6-335-P1 failed to reduce biofilm formation of *Enterococcus facieum, Staphylococcus aureus, Klebsiella pneumoniea, Acinetobacter baumanii, Enterobacter cloacae, Escherichia coli, Burkholderia cenocepacia* and *Stenotrophomonas maltophilia* (data not shown). However as displayed in FIG. 11, other members of the *Pseudomonas* genera such as *Pseudomonas putida* and *Pseudomonas fluorescens* were observed to form significantly less biofilm when challenged with H6-335-P1. As the structural freedom of H6 compounds to maintain biological activity is highly restricted (see the SAR analysis), the results of the Blast search and the biofilm experiments described above indicates that the effects of H6-335-P1 most likely is restricted to pseudomonads.

Figure 11:
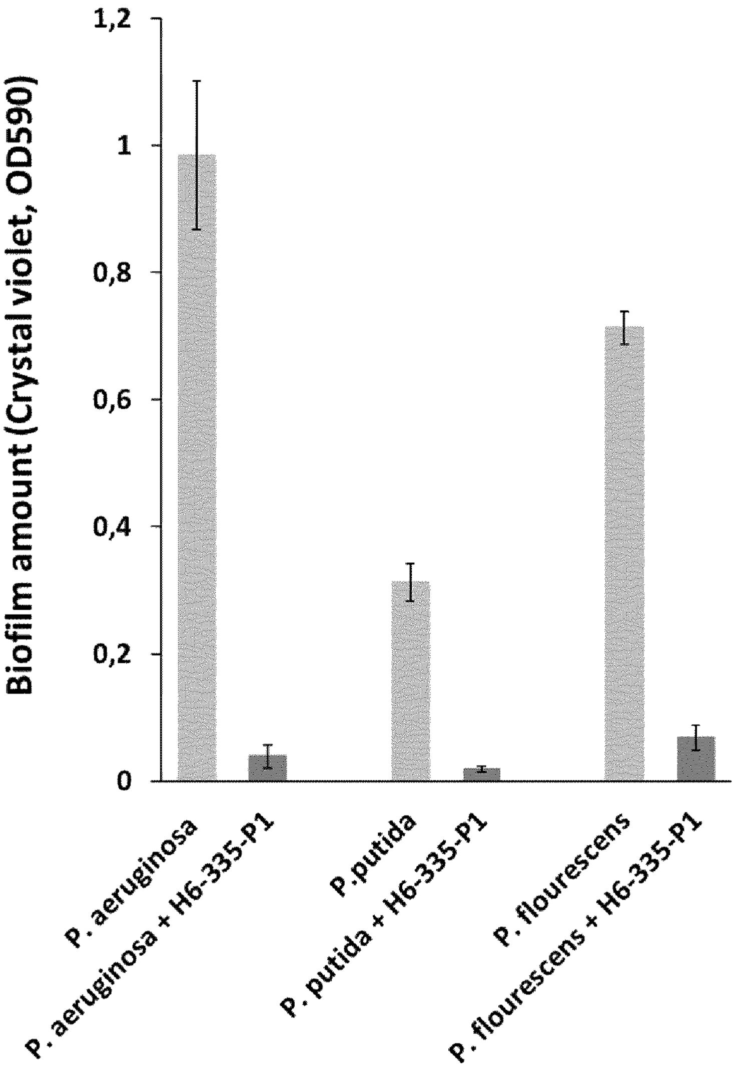
FIG. 11 shows the effect of H6-335-P1 on biofilm development of various *Pseudomonas* species. It is evident that the compound inhibits biofilm formation the three shown species.
Figure 12:
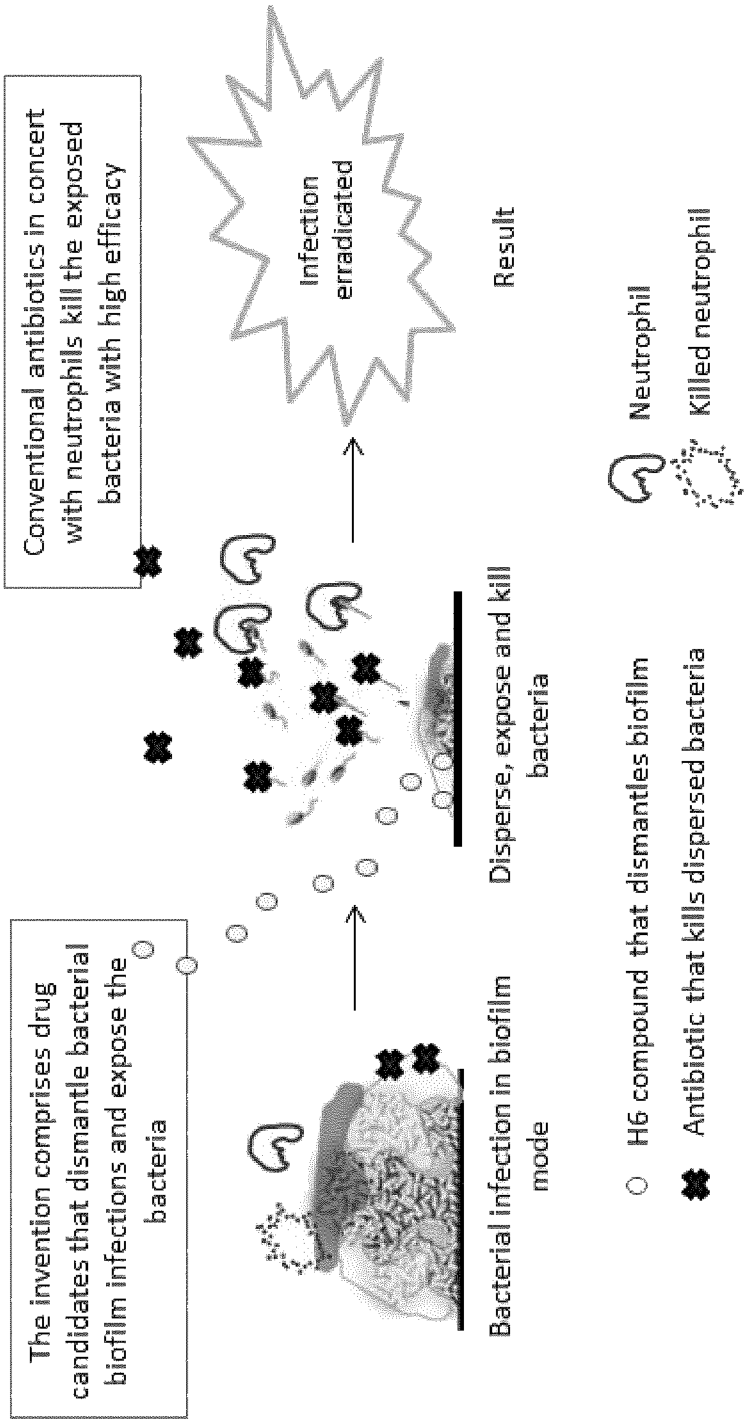
FIG. 12 shows the general pharmaceutical anti-biofilm strategy for treatment of infected patients with the present invention.

Briefly, the experiment presented in FIG. 11 were carried out in 96 well microtiter plates as follows. 20 hours old cultures of either *P. aeruginosa, P. putida* or *P. fluorescens* were diluted 1000 fold into 100 μL aliquots of ABtrace media supplemented with 0.5% Cas amino acids, 0.2% glucose, 1 μM $FeCl_3$, 0.2% DMSO and either 100 μM H6-335-P1 or none H6-335-P1. The resulting microtiter plate were sealed with an air permeable lid and the cultures were incubated at 37° C. on rotary shaker at 160 RPM. Following 8 hours of growth the culture supernatants were discarded and the amount of biofilm present in each well were quantified by the use of crystal violet staining. Finally, the obtained values of crystal violet (biofilm material) were plotted as a function of strain and the presence of 100 μM H6-335-P1 or absence of H6-335-P1. In FIG. 11 means and standard deviations (bars) represents 4 biological replicates (n=4).

REFERENCES

An, S., J. Wu, and L. H. Zhang. 2010. Modulation of *Pseudomonas aeruginosa* biofilm dispersal by a cyclic-Di-GMP phosphodiesterase with a putative hypoxia-sensing domain. Appl Environ Microbiol 76:8160-8173.

Baraquet, C., and Harwood, C. S. (2016). FleQ DNA Binding Consensus Sequence Revealed by Studies of FleQ-Dependent Regulation of Biofilm Gene Expression in *P. aeruginosa*. J Bacteriol 198(1), 178-186. doi: 10.1128/JB.00539-15.

Bernard, C. S., Bordi, C., Termine, E., Filloux, A., and de Bentzmann, S. (2009). Organization and PprB-dependent control of the *Pseudomonas aeruginosa* tad Locus, involved in Flp pilus biology. J Bacteriol 191(6), 1961-1973. doi: 10.1128/JB.01330-08.

Borlee, B. R., Goldman, A. D., Murakami, K., Samudrala, R., Wozniak, D. J., and Parsek, M. R. (2010). *Pseudomonas aeruginosa* uses a cyclic-di-GMP-regulated adhesin to reinforce the biofilm extracellular matrix. Mol Microbiol 75(4), 827-842. doi: 10.1111/j.1365-2958.2009.06991.x.

Bryers, J. D. (2008). Medical biofilms. Biotechnol Bioeng 100(1), 1-18. doi: 10.1002/bit.21838.

Ciofu, O., and Tolker-Nielsen, T. (2019). Tolerance and Resistance of *Pseudomonas aeruginosa* Biofilms to Antimicrobial Agents-How *P. aeruginosa* Can Escape Antibiotics. Front Microbiol 10, 913. doi: 10.3389/fmicb.2019.00913.

Crusz, S. A., Popat, R., Rybtke, M. T., Camara, M., Givskov, M., Tolker-Nielsen, T., et al. (2012). Bursting the bubble on bacterial biofilms: a flow cell methodology. Biofouling 28(8), 835-842. doi: 10.1080/08927014.2012.716044.

Fazli, M., Almblad, H., Rybtke, M. L., Givskov, M., Eberl, L., and Tolker-Nielsen, T. (2014). Regulation of biofilm formation in *Pseudomonas* and *Burkholderia* species. Environ Microbiol 16(7), 1961-1981. doi: 10.1111/1462-2920.12448.

Friedman, L., and R. Kolter. 2003. Genes involved in matrix formation in *Pseudomonas aeruginosa* PA14 biofilms. Molecular Microbiology 51:675-690.

Groizeleau, J., Rybtke, M., Andersen, J. B., Berthelsen, J., Liu, Y., Yang, L., et al. (2016). The anti-cancerous drug doxorubicin decreases the c-di-GMP content in *Pseudomonas aeruginosa* but promotes biofilm formation. Microbiology 162(10), 1797-1807. doi: 10.1099/mic.0.000354.

Hall, C. W., and Mah, T. F. (2017). Molecular mechanisms of biofilm-based antibiotic resistance and tolerance in pathogenic bacteria. FEMS Microbiol Rev 41(3), 276-301. doi: 10.1093/femsre/fux010.

Hickman, J. W., Tifrea, D. F., and Harwood, C. S. (2005). A chemosensory system that regulates biofilm formation through modulation of cyclic diguanylate levels. Proc Natl Acad Sci USA 102(40), 14422-14427. doi: 10.1073/pnas.0507170102.

Jenal, U., Reinders, A., and Lori, C. (2017). Cyclic di-GMP: second messenger extraordinaire. Nat Rev Microbiol 15(5), 271-284. doi: 10.1038/nrmicro.2016.190.

Kuchma, S. L., Brothers, K. M., Merritt, J. H., Liberati, N. T., Ausubel, F. M., and O'Toole, G. A. (2007). BifA, a cyclic-Di-GMP phosphodiesterase, inversely regulates biofilm formation and swarming motility by *Pseudomonas aeruginosa* PA14. J Bacteriol 189(22), 8165-8178. doi: 10.1128/313.00586-07.

Kulasekara, H. D. 2014. Transposon mutagenesis. Methods Mol Biol 1149:501-519.

Kulasekara, H., Lee, V., Brencic, A., Liberati, N., Urbach, J., Miyata, S., et al. (2006). Analysis of *Pseudomonas aeruginosa* diguanylate cyclases and phosphodiesterases reveals a role for bis-(3'-5')-cyclic-GMP in virulence. Proc Natl Acad Sci USA 103(8), 2839-2844. doi: 10.1073/pnas.0511090103.

Pamp, S. J., and Tolker-Nielsen, T. (2007). Multiple roles of biosurfactants in structural biofilm development by *Pseudomonas aeruginosa*. J Bacteriol 189(6), 2531-2539. doi: 10.1128/313.01515-06.

Rybtke, M. T., Borlee, B. R., Murakami, K., Irie, Y., Hentzer, M., Nielsen, T. E., et al. (2012). Fluorescence-based reporter for gauging cyclic di-GMP levels in *Pseudomonas aeruginosa*. Appl Environ Microbiol 78(15), 5060-5069. doi: 10.1128/AEM.00414-12.

Savjani, K. T., Gajjar, A. K., and Savjani, J. K. (2012). Drug solubility: importance and enhancement techniques. ISRN Pharm 2012, 195727. doi: 10.5402/2012/195727.

Starkey, M., Hickman, J. H., Ma, L., Zhang, N., De Long, S., Hinz, A., et al. (2009). *Pseudomonas aeruginosa* rugose small-colony variants have adaptations that likely promote persistence in the cystic fibrosis lung. J Bacteriol 191(11), 3492-3503. doi: 10.1128/313.00119-09.

The invention claimed is:

1. A method of inhibiting or treating a *Pseudomonas* bacterial biofilm infection in a subject comprising:

administering a compound according to chemical formula (1) to a subject that has a *Pseudomonas* bacterial biofilm infection:

Formula (1)

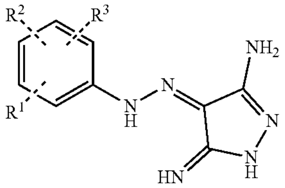

wherein $R^1$, $R^2$, and $R^3$ are hydrogen, hydroxy, or fluoro, and pharmaceutically acceptable salts of the primary or secondary amino groups, wherein the primary or secondary amino groups are protonated and the resulting positive charge is countered by an anion amine group.

2. The method according to claim 1, wherein the anion is selected from the group consisting of organic anions, acetate, trifluoroacetate, aspartate, benzenesulfonate, benzoate, besylate, bicarbonate, bitartrate, camsylate, carbonate, citrate, decanoate, edetate, esylate, fumarate, gluceptate, gluconate, glutamate, glycolate, hexanoate, hydroxynaphthoate, isethionate, lactate, lactobionate, malate, maleate, mandelate, mesylate, methylsulfate, mucate, napsylate, octanoate, oleate, pamoate, pantothenate, polygalactonate, propionate, salicylate, stearate, succinate, tartrate, teoclate, tosylate, inorganic anions, tetrafluoroborate, hexafluorophosphate, bromide, chloride, iodide, nitrate, phosphate, and sulfate.

3. The method according to claim 1, wherein the compound is 4-[(2-fluorophenyl) hydrazinylidene]pyrazole-3,5-diamine (H6-335-P1) having the following formula (2):

Formula (2)

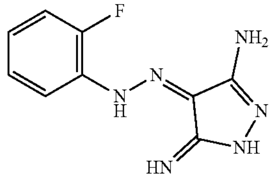

or pharmaceutically acceptable salt of the primary or secondary amino groups, wherein the primary or secondary amino groups are protonated and the resulting positive charge is countered by an anion, wherein the anion is selected from the group consisting of organic anions, acetate, trifluoroacetate, aspartate, benzenesulfonate, benzoate, besylate, bicarbonate, bitartrate, camsylate, carbonate, citrate, decanoate, edetate, esylate, fumarate, gluceptate, gluconate, glutamate, glycolate, hexanoate, hydroxynaphthoate, isethionate, lactate, lactobionate, malate, maleate, mandelate, mesylate, methylsulfate, mucate, napsylate, octanoate, oleate, pamoate, pantothenate, polygalactonate, propionate, salicylate, stearate, succinate, tartrate, teoclate, tosylate, inorganic anions, tetrafluoroborate, hexafluorophosphate, bromide, chloride, iodide, nitrate, phosphate, and sulfate.

4. The method according to claim 1, wherein the infection caused by a biofilm-forming bacteria of the genus *Pseudomonas* is selected from the group consisting of infections in wounds, eyes, urinary tract and respiratory tract.

5. The method according to claim 1, wherein the compound or the pharmaceutically acceptable salt thereof is administered in combination with one or more antibiotic(s).

6. The method according to claim 5, wherein the compound or the pharmaceutically acceptable salt thereof is administered concurrently with or prior to administration of the one or more antibiotic(s).

7. The method according to claim 5, wherein the one or more antibiotic(s) is selected from the group consisting of ciprofloxacin, tobramycin and meropenem.

8. The method according to claim 5, wherein the one or more antibiotic(s) is administered in a controlled release formulation or in a form suitable for topical, oral, intravenous, intramuscular or intraperitoneal administration.

9. The method according to claim 1, wherein said compound, pharmaceutically acceptable salt or tautomer thereof, activates the c-di-GMP degrading activity of BifA phosphodiesterase present in *P. aeruginosa*.

10. A method of dispersing a biofilm formed by a *Pseudomonas* bacteria in an industrial water system comprising:

contacting water in an industrial water system with a compound according to chemical formula (1):

Formula (1)

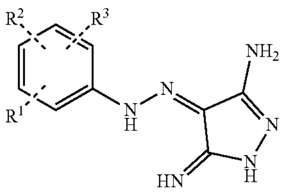

wherein $R^1$, $R^2$, and $R^3$ are independently selected from the group consisting of hydrogen, hydroxy, or fluoro, and salts of the primary or secondary amino groups, wherein the primary or secondary amino groups are protonated and the resulting positive charge is countered by an anion.

11. The method according to claim 10, wherein the compound or a salt thereof is administered to said industrial water system with a detergent and/or a biocide.

* * * * *